US008409859B2

(12) United States Patent
Verfaillie et al.

(10) Patent No.: US 8,409,859 B2
(45) Date of Patent: Apr. 2, 2013

(54) DIFFERENTIATION OF NON-EMBRYONIC STEM CELLS TO CELLS HAVING A PANCREATIC PHENOTYPE

(75) Inventors: Catherine M. Verfaillie, Leuven (BE); Miguel Angel Barajas Velez, Pamplona (ES); Yves Pierre Heremans, Heverlee (BE)

(73) Assignee: Regents of the University of Minnesota, St. Paul, MN (US)

( * ) Notice: Subject to any disclaimer, the term of this patent is extended or adjusted under 35 U.S.C. 154(b) by 1070 days.

(21) Appl. No.: 12/089,868

(22) PCT Filed: Oct. 16, 2006

(86) PCT No.: PCT/US2006/040212
§ 371 (c)(1),
(2), (4) Date: Nov. 5, 2008

(87) PCT Pub. No.: WO2007/047509
PCT Pub. Date: Apr. 26, 2007

(65) Prior Publication Data
US 2009/0092586 A1    Apr. 9, 2009

Related U.S. Application Data

(60) Provisional application No. 60/726,750, filed on Oct. 14, 2005.

(51) Int. Cl.
*C12N 15/00*    (2006.01)
(52) U.S. Cl. .......................... 435/377; 435/384
(58) Field of Classification Search .................. None
See application file for complete search history.

(56) References Cited

U.S. PATENT DOCUMENTS

| | | | |
|---|---|---|---|
| 5,486,359 A | 1/1996 | Caplan et al. | |
| 5,827,735 A | 10/1998 | Young et al. | |
| 6,090,625 A | 7/2000 | Abuljadayel | |
| 6,653,134 B2 | 11/2003 | Prockop et al. | |
| 6,777,231 B1 | 8/2004 | Katz et al. | |
| 7,033,831 B2 | 4/2006 | Fisk et al. | |
| 7,045,148 B2 | 5/2006 | Hariri | |
| 7,056,738 B2 | 6/2006 | Prockop et al. | |
| 7,229,827 B2 | 6/2007 | Kim et al. | |
| 7,311,905 B2 | 12/2007 | Hariri | |
| 2001/0024824 A1 | 9/2001 | Moss et al. | |
| 2001/0033834 A1 | 10/2001 | Wilkison et al. | |
| 2001/0046489 A1 | 11/2001 | Habener et al. | |
| 2002/0061587 A1 | 5/2002 | Anversa | |
| 2002/0164794 A1 | 11/2002 | Wernet | |
| 2003/0003090 A1 | 1/2003 | Prockop et al. | |
| 2003/0032179 A1 | 2/2003 | Hariri | |
| 2003/0059414 A1 | 3/2003 | Ho et al. | |
| 2003/0138948 A1* | 7/2003 | Fisk et al. ............... | 435/366 |
| 2004/0235165 A1 | 11/2004 | Prockop et al. | |
| 2005/0169896 A1 | 8/2005 | Li et al. | |
| 2006/0177925 A1 | 8/2006 | Rosenberg et al. | |

FOREIGN PATENT DOCUMENTS

| | | |
|---|---|---|
| WO | WO 96/23870 | 8/1996 |
| WO | WO 99/16863 | 4/1999 |
| WO | WO 99/35243 | 7/1999 |
| WO | WO 01/04268 | 1/2001 |
| WO | WO 01/08691 | 2/2001 |
| WO | WO 01/11011 | 2/2001 |
| WO | WO 01/21766 | 3/2001 |
| WO | WO 01/21767 | 3/2001 |
| WO | WO 01/23528 | 5/2001 |
| WO | WO 01/39784 | 6/2001 |
| WO | WO 01/62901 | 8/2001 |
| WO | WO 02/08388 | 3/2002 |
| WO | WO 02/34890 | 5/2002 |
| WO | WO 02/074045 | 9/2002 |
| WO | WO 02/079457 | 10/2002 |
| WO | WO 03/050249 | 6/2003 |
| WO | WO 2004/011621 | 2/2004 |

OTHER PUBLICATIONS van Eyll et al. Shh-dependent differentiation of intestinal tissue from embryonic pancreas by activin A Journal of Cell Science, 2004, Vo. 117, pp. 2077-2086.*
Kumar et al. Signals from lateral plate mesoderm instruct endoderm toward apancreatic fate Developmental Biology 259 (2003) 109-122.*
Cambrex specimens, "Poietics Human Mesenchymal Stem Cell Systems," Cambrex BioScience Walkersville, Inc. (2005).
Prockop, D., "Marrow stromal cells as stem cells for nonhematopoietic tissues" Science; 276:71-74 (1997).
Bjornson et al., "Turning brain into blood: a hematopoietic fate adopted by adult neural stem cells in vivo" Science; 283:534-537 (1999).
Reyes et al., "Purification and ex vivo expansion of postnatal human marrow mesodermal progenitor cells" Blood; 98:2615-25 (2001).
Bouwens, L., "Transdifferentiation versus stem cell hypothesis for the regeneration of islet beta-cells in the pancreas" Microscopy Research and Technique; 43:332-336 (1998).
Reyes et al., "Origin of endothelial progenitors in human postnatal bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of glial and neuronal cells from adult bone marrow mesenchymal stem cells" Abstract No. 1676, American Society for Hematology (2001).
Reyes et al., "Skeletal smooth and cardiac muscle differentiation from single adult marrow derived mesodermal progenitor cells" Abstract No. 2610, American Society for Hematology (2001).
Reyes et al., "In vitro and in vivo characterization of neural cells derived from mesenchymal stem cells" Abstract 2126, American Society for Hematology (2001).

(Continued)

*Primary Examiner* — Deborah Crouch
(74) *Attorney, Agent, or Firm* — Tarolli, Sundheim, Covell & Tummino L.L.P.

(57) ABSTRACT

The invention provides methods for differentiating non-embryonic multipotent stem cells along the pancreatic lineage. The present invention further provides non-embryonic multipotent stem cells and progeny derived therefrom to provide pancreatic cells to a subject.

11 Claims, 14 Drawing Sheets

OTHER PUBLICATIONS

Reyes et al., "Endothelial cells generated from human marrow derived mesenchymal stem cells (MSC)" Abstract No. 2276, American Society for Hematology (2001).
Zhao el al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:896-904 (2002).
Jiang et al., "Pluripotency of mesenchymal stem cells derived from adult marrow" Nature; 418:41-49 (2002).
Schwartz, R., "Multipotent adult progenitor cells from bone marrow differentiate into hepatocyte-like cells" J Clin Invest.; 109:1291-1302 (2002).
Zhao et al., "Human bone marrow stem cells exhibit neural phenotypes and ameliorate neurological deficits after grafting into the ischemic brain of rats" Exp Neural; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "investigator Profile" Journal of Hematotherapy and Stem Cell Research; 11:441-444 (2002).
Verfaillie et al., "Stem cells: hype and reality" Hematology (Am Sac Hematol Educ Program): 369-391 (2002).
Verfaille, C., "Optimizing hematopoietic stem cell engraftment: a novel role for thrombopoeitin" J. Clin, Invest.; 110:303-304 (2002).
Liu et al., "Myeloid-lymphoid-initiating cells (ML-IC) are highly enriched in the rhodamine-C-Kit(+) CD33(−)CD38(−) fraction of umbilical cord CD34(+)" Exp. Hematol.; 30:582-589 (2002).
Lewis et al., "Multi-lineage expansion potential of primitive hematopoietic progenitors: superiority of umbilical cord blood compared to mobilized peripheral blood" Exp. Hematol; 28:1087-1095 (2002).
Verfaillie, C.M., "Meeting Report on an NHLBI Workshop on ex vivo expansion of stem cells, Jul. 29, 1999, Washington D.C. National Heart Lung and Blood Institute" Exp. Hematol.; 28:361-364 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fetal liver, cord blood and bone marrow hematopoietic progenitors: implications for anatomical localization and developmental stage specific regulation of hematopoiesis" Exp. Hematol.; 27:302-312 (1999).
Miller et al., "Ex vivo culture of CD34+/Lin-/DR- cells in stroma-derived soluble factors, interleukin-3, and macrophage inflammatory protein-1 alpha maintains not only myeloid but also lymphoid progenitors in a novel switch culture assay" Blood; 15:4516-4522 (1998).
Verfaillie, C., "Stem cells in chronic myelogenous Leukemia" Hematol. Oncol. Clin. North Am.; 11:1079-1114 (1997).
Prosper et al, "Phenotypic and functional characterization of long-term culture-initiating cells present in peripheral blood progenitor collections of normal donors treated with granulocyte colony-stimulating factor" Blood; 15:2033-2042 (1996).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientists herald a versatile adult cell" The New York Times on the Web, Jan. 25, 2002.
Rosford et al., "The octamer motif present in the Rex-1 promoter binds Oct-1 and Oct-3 expressed by EC cells and ES cells" Biochem. Biophys. Res. Comm.; 203:1795-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is regulated via Oct-3/4 and Oct-6 binding to and octamer site and a novel protein, R ox-1, binding to an adjacent site" Mol. Cell Biol.; 18:1866-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Bonnet, "Nonhematopoietic/endothelial SSE-1+ cells define the most primitive progenitors in the adult murine bone marrow mesenchymal compartment" Blood; 109:1298-1306 (2007).
Bertani et al., "Neurogenic potential of human mesenchymal stem cells revisited: analysis by immunostaining, time-lapse video and microarray" J Cell Sci.; 118:3925-36 (2005).
Bodnar et al., "Extension of life-span by introduction of telomerase into normal human cells" Science; 279:349-352 (1998).
Horwitz et al., "Clarification of the nomenclature for MSC: the international society for cellular therapy position paper" Cytotherapy; 7:393-395 (2005).
Lu et al., "Induction of bone marrow stromal cells to neurons: differentiation, transdifferentiation, or artifact" J Neurosci Res; 77:174-91 (2004).
Neuhuber et al., "Reevaluation of in vitro differentiation protocols for bone marrow stromal cells: disruption of actin cytoskeleton induces rapid morphological changes and mimics neuronal phenotype" J Neurosci Res; 77:192-204 (2004).
Simonsen et al., "Telomerase expression extends the proliferative life-span and maintains the osteogenic potential of human bone marrow stromal cells" Nature Biotechnology; 20:592-596 (2002).
Zimmerman et al., "Lack of telomerase activity in human mesenchymal stem cells" Leukemia; 17:1146-1149 (2003).
Izadpanah et al., "Biologic properties of mesenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Moriscot et al., "Human bone marrow mesenchymal stem cell can express insulin and key transcription factors of the endocrine pancreas developmental pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neurol.; 164:247-56 (2000).
Eglitis et al., "Hematopoietic cells differentiate into both microglia and macroglia in the brain of adult mice" Proc. Natl. Acad. Sci. USA; 94:4080-85 (1997).
Kopen et al., "Marrow stromal cells migrate throughout forebrain and cerebellum, and they differentiate into astrocytes after injection into neonatal mouse brains" Proc. Natl. Acad. Sci. USA; 96:10711-16 (1999).
Lagasse et al., "Purified hematopoietic stem cells can differentiate into hepatocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaillie, C.M., Multipotent adult progenitor cells: an update: Novartis Found Symp., 254:55-65 (2005).
Aldhous et al., "Fresh questions on stem cell findings" New Scientist, Mar. 21, 2007.
Brazelton et al, "From marrow to brain: expression of neuronal phenotypes in adult mice" Science; 290:1775-9 (2000).
Clarke et al., "Generalized potential of adult neural stem cells" Science; 288: 1660-3 (2000).
Johansson et al., "Neural stem cells in the adult human brain" Exp. Cell. Res.; 253:733-6 (1999).
Mezey et al., "Turning blood into brain: cells bearing neuronal antigens generated in vivo from bone marrow" Science; 290:1779-82 (2000).

Morshead et al., "Hematopoietic competence is a rare property of neural stem cells that may depend on genetic and epigenetic alterations" Nat. Med.; 8:268-73 (2002).

Petersen et al., "Bone marrow as a potential source of hepatic oval cells" Science; 284:1168-70 (1999).

Scintu et al,, "Differentiation of human bone marrow stem cells into cells with a neural phenotype: diverse effects of two specific treatments" BMC Neurosci.; 7:14 (2006).

U.S. Patent and Trademark Office, Office Action dated Jun. 24, 2005 in related U.S. Appl. No. 10/040,757.

U.S. Patent and Trademark Office, Office Action and 892 dated Jun. 27, 2008 in related U.S. Appl. No. 10/467,963.

U.S. Patent and Trademark Office, Office Action dated Oct. 15, 2009 in related U.S. Appl. No. 10/467,963.

U.S. Patent and Trademark Office, Office Action and 892 dated Apr. 7, 2008 in related U.S. Appl. No. 11/151,689.

U.S. Patent and Trademark Office, Office Action dated Jan. 4, 2006 in related U.S. Appl. No. 11/238,234.

U.S. Patent and Trademark Office, Office Action dated Aug. 29, 2006 in related U.S. Appl. No. 11/238,234.

U.S. Patent and Trademark Office, Office Action and 892 dated Apr. 3, 2007 in related U.S. Appl. No. 11/238,234.

U.S. Patent and Trademark Office, Office Action dated Oct. 7, 2008 in related U.S. Appl. No. 11/238,234.

Communication and 1449, filed Oct. 2, 2007 in related U.S. Appl. No. 11/238,234, and supplemental 1449 submitted on Oct. 4, 2007.

Information Disclosure Statement, Second Communication and PTO/SB/08b, filed Dec. 24, 2008 in related U.S. Appl. No. 11/238,234.

Gmyr et al., "Adult Human Cytokeratin 19-Positive Cells Reexpress Insulin Promoter Factor I in Vitro" Diabetes; 49:1671-1680 (2000).

Verfaillie et al., "The undoing of differentiation by four defined factors: a big step forward towards generating patient specific pluripotent stem cells" J Hepatology; 49:876-878 (2008).

Serafini et al., Pluripotericy in adult stem cells: state of the art Semin Reprod Med; 24:379-388 (2006).

Snykers et al., "Sequential exposure to cytokines reflecting embryogenesis: the key for in vitro differentiation of adult bone marrow stem cells into functional hepatocyte-like cells" Toxicol Sci; 94:330-341 (2006).

Schwartz et al., Defined conditions for development of functional hepatic cells from human embryonic stem cells Stem Cells Dev; 14:643-655 (2005).

Dichmann, Darwin, et al., Expression and Misexpression of Members of the FGF and TGFβ Families of Growth Factors in the Developing Mouse Pancreas, *Developmental Dynamics*, 226: 663-674 (2003).

\* cited by examiner

Oct4 mRNA EXPRESSION MAPC
(RELATIVE TO GAPDH)
| HIGH oct4 (HO) | 0.3241 ± 0.333 |
|---|---|
| LOW oct4 (LO) | 0.0003 ± 0.00001 |
*FIG. 2A*
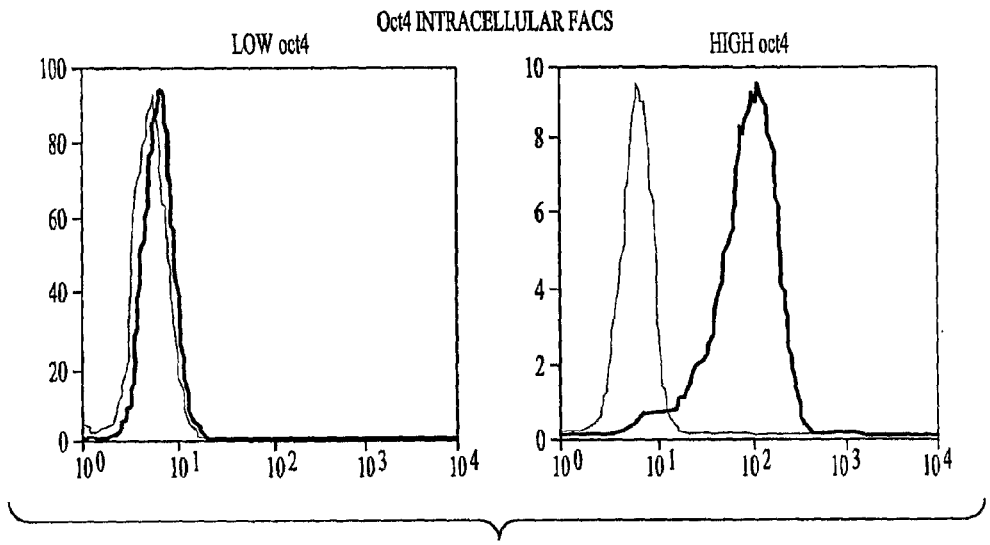
*FIG. 2B*
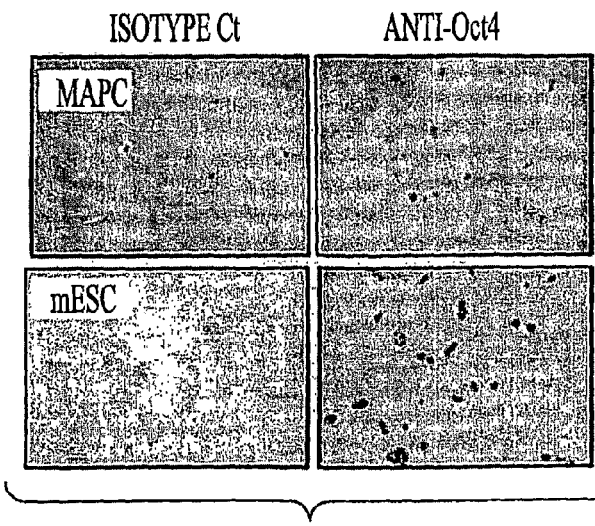
*FIG. 2C*

|  | HIGH Oct 4 mMAPC |
|---|---|
| Oct3/4 | 20-80 |
| Rex1 | 10-100 |
| Nanog | <0.01 |
| Sox2 | <0.001 |
| Fgf4 | <0.1 |
| Fbx15 | 100 |
| FoxD3 | 100 |
| Utf1 | <0.1 |
| Eras | <0.01 |
| Tcl1 | <0.01 |
| Tdgf1 | <0.01 |
| Ecat1 | <0.1 |
| Egs1 | 10-30 |
| GDF3 | <0.01 |
| Dnmt31 | 80.-100 |
| Ecat7 | 80-100 |

*FIG. 2D*

SEQUENCE LISTING

```
<160> NUMBER OF SEQ ID NOS: 102

<210> SEQ ID NO 1
<211> LENGTH: 20
<212> TYPE: DNA
<213> ORGANISM: Artificial Sequence
<220> FEATURE:
<223> OTHER INFORMATION: A synthetic primer

<400> SEQUENCE: 1 ttacccaca cacagtccaa                                                  20

<210> SEQ ID NO 2
<211> LENGTH: 20
<212> TYPE: DNA
<213> ORGANISM: Artificial Sequence
<220> FEATURE:
<223> OTHER INFORMATION: A synthetic primer

<400> SEQUENCE: 2
ccaaaaacac ggcttcagtt                                                 20

<210> SEQ ID NO 3
<211> LENGTH: 20
<212> TYPE: DNA
<213> ORGANISM: Artificial Sequence
<220> FEATURE:
<223> OTHER INFORMATION: A synthetic primer

<400> SEQUENCE: 3
tagggtgcca tttggagttc                                                 20

<210> SEQ ID NO 4
<211> LENGTH: 20
<212> TYPE: DNA
<213> ORGANISM: Artificial Sequence
<220> FEATURE:
<223> OTHER INFORMATION: A synthetic primer

<400> SEQUENCE: 4
acattgccca ggtttgtctc                                                 20

<210> SEQ ID NO 5
```

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 5
cctacctccc attccaggat                                                    20

<210> SEQ ID NO 6
<211> LENGTH: 20
<212> TYPE: DNA
<213> ORGANISM: Artificial Sequence
<220> FEATURE:
<223> OTHER INFORMATION: A synthetic primer

<400> SEQUENCE: 6
gcaccctaag cacagctacc                                                    20

<210> SEQ ID NO 7
<211> LENGTH: 22
<212> TYPE: DNA
<213> ORGANISM: Artificial Sequence
<220> FEATURE:
<223> OTHER INFORMATION: A synthetic primer

<400> SEQUENCE: 7
ccacttgaga atttcatgag ca                                                 22

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
tttacatgac ccagcacacc                                                    20

<210> SEQ ID NO 9
<211> LENGTH: 20
<212> TYPE: DNA
<213> ORGANISM: Artificial Sequence
<220> FEATURE:
<223> OTHER INFORMATION: A synthetic primer

<400> SEQUENCE: 9
aggtggcagc ttgtgaagat                                                    20

<210> SEQ ID NO 10
<211> LENGTH: 20
<212> TYPE: DNA
<213> ORGANISM: Artificial Sequence
<220> FEATURE:
<223> OTHER INFORMATION: A synthetic primer

<400> SEQUENCE: 10
gagtcggctc ctatggtgtc                                                    20

<210> SEQ ID NO 11
<211> LENGTH: 21
<212> TYPE: DNA
<213> ORGANISM: Artificial Sequence
<220> FEATURE:
<223> OTHER INFORMATION: A synthetic primer

<400> SEQUENCE: 11
```

```
agcccattgt tcattcttgt g                                            21

<210> SEQ ID NO 12
<211> LENGTH: 20
<212> TYPE: DNA
<213> ORGANISM: Artificial Sequence
<220> FEATURE:
<223> OTHER INFORMATION: A synthetic primer

<400> SEQUENCE: 12
agaggaaggg tgtgctctga                                              20

<210> SEQ ID NO 13
<211> LENGTH: 22
<212> TYPE: DNA
<213> ORGANISM: Artificial Sequence
<220> FEATURE:
<223> OTHER INFORMATION: A synthetic primer

<400> SEQUENCE: 13
tgagccatta atttttgggt tt                                           22

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
agcagtatct gcctgtgcaa                                              20

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

<400> SEQUENCE: 15
aatgtttcct tgtgcctgct                                              20

<210> SEQ ID NO 16
<211> LENGTH: 20
<212> TYPE: DNA
<213> ORGANISM: Artificial Sequence
<220> FEATURE:
<223> OTHER INFORMATION: A synthetic primer

<400> SEQUENCE: 16
ccaggtccag tgtttcaggt                                              20

<210> SEQ ID NO 17
<211> LENGTH: 20
<212> TYPE: DNA
<213> ORGANISM: Artificial Sequence
<220> FEATURE:
<223> OTHER INFORMATION: A synthetic primer

<400> SEQUENCE: 17
caggcatgat gctgagtgac                                              20

<210> SEQ ID NO 18
<211> LENGTH: 20
<212> TYPE: DNA
<213> ORGANISM: Artificial Sequence
<220> FEATURE:
```

```
<223> OTHER INFORMATION: A synthetic primer

<400> SEQUENCE: 18
cagggacctc atctttggaa                                            20

<210> SEQ ID NO 19
<211> LENGTH: 20
<212> TYPE: DNA
<213> ORGANISM: Artificial Sequence
<220> FEATURE:
<223> OTHER INFORMATION: A synthetic primer

<400> SEQUENCE: 19
tcacaatcct gtggatctgg                                            20

<210> SEQ ID NO 20
<211> LENGTH: 20
<212> TYPE: DNA
<213> ORGANISM: Artificial Sequence
<220> FEATURE:
<223> OTHER INFORMATION: A synthetic primer

<400> SEQUENCE: 20
ccctcagtac ctggaccaaa                                            20

<210> SEQ ID NO 21
<211> LENGTH: 20
<212> TYPE: DNA
<213> ORGANISM: Artificial Sequence
<220> FEATURE:
<223> OTHER INFORMATION: A synthetic primer

<400> SEQUENCE: 21
ccaaggggaa tcagaactca                                            20

<210> SEQ ID NO 22
<211> LENGTH: 20
<212> TYPE: DNA
<213> ORGANISM: Artificial Sequence
<220> FEATURE:
<223> OTHER INFORMATION: A synthetic primer

<400> SEQUENCE: 22
tggagcaggc ccaaatatag                                            20

<210> SEQ ID NO 23
<211> LENGTH: 20
<212> TYPE: DNA
<213> ORGANISM: Artificial Sequence
<220> FEATURE:
<223> OTHER INFORMATION: A synthetic primer

<400> SEQUENCE: 23
tgcaacagct ctcacctacg                                            20

<210> SEQ ID NO 24
<211> LENGTH: 20
<212> TYPE: DNA
<213> ORGANISM: Artificial Sequence
<220> FEATURE:
<223> OTHER INFORMATION: A synthetic primer

<400> SEQUENCE: 24
aagatgggca actcaaatgg                                            20

<210> SEQ ID NO 25
```

-continued

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 25
actgagatgc tgggctgtct                                              20

<210> SEQ ID NO 26
<211> LENGTH: 20
<212> TYPE: DNA
<213> ORGANISM: Artificial Sequence
<220> FEATURE:
<223> OTHER INFORMATION: A synthetic primer

<400> SEQUENCE: 26
gacccttcct gacagtcgtc                                              20

<210> SEQ ID NO 27
<211> LENGTH: 20
<212> TYPE: DNA
<213> ORGANISM: Artificial Sequence
<220> FEATURE:
<223> OTHER INFORMATION: A synthetic primer

<400> SEQUENCE: 27
gagaccttcg tccacctctg                                              20

<210> SEQ ID NO 28
<211> LENGTH: 20
<212> TYPE: DNA
<213> ORGANISM: Artificial Sequence
<220> FEATURE:
<223> OTHER INFORMATION: A synthetic primer

<400> SEQUENCE: 28
cattgacaac ggcgacatac                                              20

<210> SEQ ID NO 29
<211> LENGTH: 20
<212> TYPE: DNA
<213> ORGANISM: Artificial Sequence
<220> FEATURE:
<223> OTHER INFORMATION: A synthetic primer

<400> SEQUENCE: 29
ccctttgaac tgccttgtgt                                              20

<210> SEQ ID NO 30
<211> LENGTH: 20
<212> TYPE: DNA
<213> ORGANISM: Artificial Sequence
<220> FEATURE:
<223> OTHER INFORMATION: A synthetic primer

<400> SEQUENCE: 30
tgcattcatt tggattggaa                                              20

<210> SEQ ID NO 31
<211> LENGTH: 20
<212> TYPE: DNA
<213> ORGANISM: Artificial Sequence
<220> FEATURE:
<223> OTHER INFORMATION: A synthetic primer

<400> SEQUENCE: 31
```

```
tcactgaccc ttccatcctc                                              20

<210> SEQ ID NO 32
<211> LENGTH: 20
<212> TYPE: DNA
<213> ORGANISM: Artificial Sequence
<220> FEATURE:
<223> OTHER INFORMATION: A synthetic primer

<400> SEQUENCE: 32
ggaataccga ggctgatgaa                                              20

<210> SEQ ID NO 33
<211> LENGTH: 21
<212> TYPE: DNA
<213> ORGANISM: Artificial Sequence
<220> FEATURE:
<223> OTHER INFORMATION: A synthetic primer

<400> SEQUENCE: 33
tggaagaagg agagctcaca g                                            21

<210> SEQ ID NO 34
<211> LENGTH: 20
<212> TYPE: DNA
<213> ORGANISM: Artificial Sequence
<220> FEATURE:
<223> OTHER INFORMATION: A synthetic primer

<400> SEQUENCE: 34
cattcaggtg tgaggcaagg                                              20

<210> SEQ ID NO 35
<211> LENGTH: 20
<212> TYPE: DNA
<213> ORGANISM: Artificial Sequence
<220> FEATURE:
<223> OTHER INFORMATION: A synthetic primer

<400> SEQUENCE: 35
gatgccttca tgctgggtat                                              20

<210> SEQ ID NO 36
<211> LENGTH: 20
<212> TYPE: DNA
<213> ORGANISM: Artificial Sequence
<220> FEATURE:
<223> OTHER INFORMATION: A synthetic primer

<400> SEQUENCE: 36
taggtgtaac cagggcaag                                               20

<210> SEQ ID NO 37
<211> LENGTH: 20
<212> TYPE: DNA
<213> ORGANISM: Artificial Sequence
<220> FEATURE:
<223> OTHER INFORMATION: A synthetic primer

<400> SEQUENCE: 37
ccaatcagct tgggctagag                                              20

<210> SEQ ID NO 38
<211> LENGTH: 20
<212> TYPE: DNA
<213> ORGANISM: Artificial Sequence
<220> FEATURE:
```

<223> OTHER INFORMATION: A synthetic primer

<400> SEQUENCE: 38
cctgggaaag gtgtcctgta                                              20

<210> SEQ ID NO 39
<211> LENGTH: 20
<212> TYPE: DNA
<213> ORGANISM: Artificial Sequence
<220> FEATURE:
<223> OTHER INFORMATION: A synthetic primer

<400> SEQUENCE: 39
caaggcaagg gaggtagaca                                              20

<210> SEQ ID NO 40
<211> LENGTH: 20
<212> TYPE: DNA
<213> ORGANISM: Artificial Sequence
<220> FEATURE:
<223> OTHER INFORMATION: A synthetic primer

<400> SEQUENCE: 40
gctcctgatc aacagcatca                                              20

<210> SEQ ID NO 41
<211> LENGTH: 20
<212> TYPE: DNA
<213> ORGANISM: Artificial Sequence
<220> FEATURE:
<223> OTHER INFORMATION: A synthetic primer

<400> SEQUENCE: 41
cacaactcgg agatcagcaa                                              20

<210> SEQ ID NO 42
<211> LENGTH: 20
<212> TYPE: DNA
<213> ORGANISM: Artificial Sequence
<220> FEATURE:
<223> OTHER INFORMATION: A synthetic primer

<400> SEQUENCE: 42
tgtaatccgg gtgttccttc                                              20

<210> SEQ ID NO 43
<211> LENGTH: 20
<212> TYPE: DNA
<213> ORGANISM: Artificial Sequence
<220> FEATURE:
<223> OTHER INFORMATION: A synthetic primer

<400> SEQUENCE: 43
tattccagga gcgatccaac                                              20

<210> SEQ ID NO 44
<211> LENGTH: 20
<212> TYPE: DNA
<213> ORGANISM: Artificial Sequence
<220> FEATURE:
<223> OTHER INFORMATION: A synthetic primer

<400> SEQUENCE: 44
ctcgttccag ttgctcacaa                                              20

<210> SEQ ID NO 45

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 45
aggaacatgg ttgccttcag                                          20

<210> SEQ ID NO 46
<211> LENGTH: 20
<212> TYPE: DNA
<213> ORGANISM: Artificial Sequence
<220> FEATURE:
<223> OTHER INFORMATION: A synthetic primer

<400> SEQUENCE: 46
agtgcttgac aaagcccagt                                          20

<210> SEQ ID NO 47
<211> LENGTH: 20
<212> TYPE: DNA
<213> ORGANISM: Artificial Sequence
<220> FEATURE:
<223> OTHER INFORMATION: A synthetic primer

<400> SEQUENCE: 47
ggaaacattg ggggaacttt                                          20

<210> SEQ ID NO 48
<211> LENGTH: 20
<212> TYPE: DNA
<213> ORGANISM: Artificial Sequence
<220> FEATURE:
<223> OTHER INFORMATION: A synthetic primer

<400> SEQUENCE: 48
gtgtggccca gctatttagg                                          20

<210> SEQ ID NO 49
<211> LENGTH: 20
<212> TYPE: DNA
<213> ORGANISM: Artificial Sequence
<220> FEATURE:
<223> OTHER INFORMATION: A synthetic primer

<400> SEQUENCE: 49
tgccactcag aagactgtgg                                          20

<210> SEQ ID NO 50
<211> LENGTH: 20
<212> TYPE: DNA
<213> ORGANISM: Artificial Sequence
<220> FEATURE:
<223> OTHER INFORMATION: A synthetic primer

<400> SEQUENCE: 50
ggatgcaggg atgatgttct                                          20

<210> SEQ ID NO 51
<211> LENGTH: 20
<212> TYPE: DNA
<213> ORGANISM: Artificial Sequence
<220> FEATURE:
<223> OTHER INFORMATION: A synthetic primer

<400> SEQUENCE: 51
```

```
ttttgtgcag tggttgatga                                                   20

<210> SEQ ID NO 52
<211> LENGTH: 20
<212> TYPE: DNA
<213> ORGANISM: Artificial Sequence
<220> FEATURE:
<223> OTHER INFORMATION: A synthetic primer

<400> SEQUENCE: 52
cagcatgcct ctcaaattca                                                   20

<210> SEQ ID NO 53
<211> LENGTH: 20
<212> TYPE: DNA
<213> ORGANISM: Artificial Sequence
<220> FEATURE:
<223> OTHER INFORMATION: A synthetic primer

<400> SEQUENCE: 53
gtggagccca gttgttgact                                                   20

<210> SEQ ID NO 54
<211> LENGTH: 20
<212> TYPE: DNA
<213> ORGANISM: Artificial Sequence
<220> FEATURE:
<223> OTHER INFORMATION: A synthetic primer

<400> SEQUENCE: 54
ggctcatcac cttcttcagg                                                   20

<210> SEQ ID NO 55
<211> LENGTH: 20
<212> TYPE: DNA
<213> ORGANISM: Artificial Sequence
<220> FEATURE:
<223> OTHER INFORMATION: A synthetic primer

<400> SEQUENCE: 55
accctcacca gcatgtcttc                                                   20

<210> SEQ ID NO 56
<211> LENGTH: 20
<212> TYPE: DNA
<213> ORGANISM: Artificial Sequence
<220> FEATURE:
<223> OTHER INFORMATION: A synthetic primer

<400> SEQUENCE: 56
gtcaggtcgc tggacttctc                                                   20

<210> SEQ ID NO 57
<211> LENGTH: 20
<212> TYPE: DNA
<213> ORGANISM: Artificial Sequence
<220> FEATURE:
<223> OTHER INFORMATION: A synthetic primer

<400> SEQUENCE: 57
cctgatgcaa gaacacatgg                                                   20

<210> SEQ ID NO 58
<211> LENGTH: 20
<212> TYPE: DNA
<213> ORGANISM: Artificial Sequence
<220> FEATURE:
```

<223> OTHER INFORMATION: A synthetic primer

<400> SEQUENCE: 58
tgatggctgt ggagtctcag                                        20

<210> SEQ ID NO 59
<211> LENGTH: 20
<212> TYPE: DNA
<213> ORGANISM: Artificial Sequence
<220> FEATURE:
<223> OTHER INFORMATION: A synthetic primer

<400> SEQUENCE: 59
ctgtgaaact cccccaggta                                        20

<210> SEQ ID NO 60
<211> LENGTH: 20
<212> TYPE: DNA
<213> ORGANISM: Artificial Sequence
<220> FEATURE:
<223> OTHER INFORMATION: A synthetic primer

<400> SEQUENCE: 60
tcatcccgca taagtgtgaa                                        20

<210> SEQ ID NO 61
<211> LENGTH: 20
<212> TYPE: DNA
<213> ORGANISM: Artificial Sequence
<220> FEATURE:
<223> OTHER INFORMATION: A synthetic primer

<400> SEQUENCE: 61
cacctttgtg gtcctcacct                                        20

<210> SEQ ID NO 62
<211> LENGTH: 20
<212> TYPE: DNA
<213> ORGANISM: Artificial Sequence
<220> FEATURE:
<223> OTHER INFORMATION: A synthetic primer

<400> SEQUENCE: 62
gacgggactt gggtgtgtag                                        20

<210> SEQ ID NO 63
<211> LENGTH: 20
<212> TYPE: DNA
<213> ORGANISM: Artificial Sequence
<220> FEATURE:
<223> OTHER INFORMATION: A synthetic primer

<400> SEQUENCE: 63
gaagtggagg acccacaagt                                        20

<210> SEQ ID NO 64
<211> LENGTH: 20
<212> TYPE: DNA
<213> ORGANISM: Artificial Sequence
<220> FEATURE:
<223> OTHER INFORMATION: A synthetic primer

<400> SEQUENCE: 64
cagtgccaag gtctgaaggt                                        20

<210> SEQ ID NO 65

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 65
gggacgggaa aacctactgt                                              20

<210> SEQ ID NO 66
<211> LENGTH: 20
<212> TYPE: DNA
<213> ORGANISM: Artificial Sequence
<220> FEATURE:
<223> OTHER INFORMATION: A synthetic primer

<400> SEQUENCE: 66
cacgaagtcg ttcttgctga                                              20

<210> SEQ ID NO 67
<211> LENGTH: 20
<212> TYPE: DNA
<213> ORGANISM: Artificial Sequence
<220> FEATURE:
<223> OTHER INFORMATION: A synthetic primer

<400> SEQUENCE: 67
cccaaagcaa acaaccactt                                              20

<210> SEQ ID NO 68
<211> LENGTH: 20
<212> TYPE: DNA
<213> ORGANISM: Artificial Sequence
<220> FEATURE:
<223> OTHER INFORMATION: A synthetic primer

<400> SEQUENCE: 68
gtaccccatc ctcctggaat                                              20

<210> SEQ ID NO 69
<211> LENGTH: 20
<212> TYPE: DNA
<213> ORGANISM: Artificial Sequence
<220> FEATURE:
<223> OTHER INFORMATION: A synthetic primer

<400> SEQUENCE: 69
gagtgggtgg gcgtactcta                                              20

<210> SEQ ID NO 70
<211> LENGTH: 20
<212> TYPE: DNA
<213> ORGANISM: Artificial Sequence
<220> FEATURE:
<223> OTHER INFORMATION: A synthetic primer

<400> SEQUENCE: 70
ttggaactga gcacttcgtg                                              20

<210> SEQ ID NO 71
<211> LENGTH: 20
<212> TYPE: DNA
<213> ORGANISM: Artificial Sequence
<220> FEATURE:
<223> OTHER INFORMATION: A synthetic primer

<400> SEQUENCE: 71
```
acttggcagg accagagaga                          20

<210> SEQ ID NO 72
<211> LENGTH: 20
<212> TYPE: DNA
<213> ORGANISM: Artificial Sequence
<220> FEATURE:
<223> OTHER INFORMATION: A synthetic primer

<400> SEQUENCE: 72
ggaaccagac cttgacctga                          20

<210> SEQ ID NO 73
<211> LENGTH: 20
<212> TYPE: DNA
<213> ORGANISM: Artificial Sequence
<220> FEATURE:
<223> OTHER INFORMATION: A synthetic primer

<400> SEQUENCE: 73
aggcccagaa ggtcatcatc                          20

<210> SEQ ID NO 74
<211> LENGTH: 20
<212> TYPE: DNA
<213> ORGANISM: Artificial Sequence
<220> FEATURE:
<223> OTHER INFORMATION: A synthetic primer

<400> SEQUENCE: 74
gaggagggag accgtagtcc                          20

<210> SEQ ID NO 75
<211> LENGTH: 20
<212> TYPE: DNA
<213> ORGANISM: Artificial Sequence
<220> FEATURE:
<223> OTHER INFORMATION: A synthetic primer

<400> SEQUENCE: 75
aggacaaggc tcccagtgta                          20

<210> SEQ ID NO 76
<211> LENGTH: 20
<212> TYPE: DNA
<213> ORGANISM: Artificial Sequence
<220> FEATURE:
<223> OTHER INFORMATION: A synthetic primer

<400> SEQUENCE: 76
taggaagagc tggagccaaa                          20

<210> SEQ ID NO 77
<211> LENGTH: 20
<212> TYPE: DNA
<213> ORGANISM: Artificial Sequence
<220> FEATURE:
<223> OTHER INFORMATION: A synthetic primer

<400> SEQUENCE: 77
tcccagggat ctgagaattg                          20

<210> SEQ ID NO 78
<211> LENGTH: 20
<212> TYPE: DNA
<213> ORGANISM: Artificial Sequence
<220> FEATURE:

<223> OTHER INFORMATION: A synthetic primer

<400> SEQUENCE: 78
cacaacggtt tgaaatgacg                                               20

<210> SEQ ID NO 79
<211> LENGTH: 20
<212> TYPE: DNA
<213> ORGANISM: Artificial Sequence
<220> FEATURE:
<223> OTHER INFORMATION: A synthetic primer

<400> SEQUENCE: 79
tctgcctctg ggactctttc                                               20

<210> SEQ ID NO 80
<211> LENGTH: 20
<212> TYPE: DNA
<213> ORGANISM: Artificial Sequence
<220> FEATURE:
<223> OTHER INFORMATION: A synthetic primer

<400> SEQUENCE: 80
gggaccgctc aagtttgtaa                                               20

<210> SEQ ID NO 81
<211> LENGTH: 20
<212> TYPE: DNA
<213> ORGANISM: Artificial Sequence
<220> FEATURE:
<223> OTHER INFORMATION: A synthetic primer

<400> SEQUENCE: 81
ccacccaagt ggataggaga                                               20

<210> SEQ ID NO 82
<211> LENGTH: 21
<212> TYPE: DNA
<213> ORGANISM: Artificial Sequence
<220> FEATURE:
<223> OTHER INFORMATION: A synthetic primer

<400> SEQUENCE: 82
cagcagaagg taggtgtctg g                                             21

<210> SEQ ID NO 83
<211> LENGTH: 20
<212> TYPE: DNA
<213> ORGANISM: Artificial Sequence
<220> FEATURE:
<223> OTHER INFORMATION: A synthetic primer

<400> SEQUENCE: 83
cccagactcc gtcagtttct                                               20

<210> SEQ ID NO 84
<211> LENGTH: 20
<212> TYPE: DNA
<213> ORGANISM: Artificial Sequence
<220> FEATURE:
<223> OTHER INFORMATION: A synthetic primer

<400> SEQUENCE: 84
gttgggctca gacagcagtt                                               20

<210> SEQ ID NO 85

```
<211> LENGTH: 20
<212> TYPE: DNA
<213> ORGANISM: Artificial Sequence
<220> FEATURE:
<223> OTHER INFORMATION: A synthetic primer

<400> SEQUENCE: 85
tgatcgtgtg ttgccatttt                                                     20

<210> SEQ ID NO 86
<211> LENGTH: 20
<212> TYPE: DNA
<213> ORGANISM: Artificial Sequence
<220> FEATURE:
<223> OTHER INFORMATION: A synthetic primer

<400> SEQUENCE: 86
aacaataccg aagggcacag                                                     20

<210> SEQ ID NO 87
<211> LENGTH: 20
<212> TYPE: DNA
<213> ORGANISM: Artificial Sequence
<220> FEATURE:
<223> OTHER INFORMATION: A synthetic primer

<400> SEQUENCE: 87
atccacattc ggaacaggac                                                     20

<210> SEQ ID NO 88
<211> LENGTH: 20
<212> TYPE: DNA
<213> ORGANISM: Artificial Sequence
<220> FEATURE:
<223> OTHER INFORMATION: A synthetic primer

<400> SEQUENCE: 88
caaggttccg gtgatcttgt                                                     20

<210> SEQ ID NO 89
<211> LENGTH: 20
<212> TYPE: DNA
<213> ORGANISM: Artificial Sequence
<220> FEATURE:
<223> OTHER INFORMATION: A synthetic primer

<400> SEQUENCE: 89
ccaagctcag cacacaaaaa                                                     20

<210> SEQ ID NO 90
<211> LENGTH: 20
<212> TYPE: DNA
<213> ORGANISM: Artificial Sequence
<220> FEATURE:
<223> OTHER INFORMATION: A synthetic primer

<400> SEQUENCE: 90
ccaaccactc tgggaactgt                                                     20

<210> SEQ ID NO 91
<211> LENGTH: 21
<212> TYPE: DNA
<213> ORGANISM: Artificial Sequence
<220> FEATURE:
<223> OTHER INFORMATION: A synthetic primer

<400> SEQUENCE: 91
```
cccaccggat ggctaggtat t                                              21

<210> SEQ ID NO 92
<211> LENGTH: 21
<212> TYPE: DNA
<213> ORGANISM: Artificial Sequence
<220> FEATURE:
<223> OTHER INFORMATION: A synthetic primer

<400> SEQUENCE: 92
gaggcggatc tgtttgaggt t                                              21

<210> SEQ ID NO 93
<211> LENGTH: 20
<212> TYPE: DNA
<213> ORGANISM: Artificial Sequence
<220> FEATURE:
<223> OTHER INFORMATION: A synthetic primer

<400> SEQUENCE: 93
ggccaacgaa ttggattcta                                                20

<210> SEQ ID NO 94
<211> LENGTH: 20
<212> TYPE: DNA
<213> ORGANISM: Artificial Sequence
<220> FEATURE:
<223> OTHER INFORMATION: A synthetic primer

<400> SEQUENCE: 94
gtttactggc accacgtcct                                                20

<210> SEQ ID NO 95
<211> LENGTH: 39
<212> TYPE: DNA
<213> ORGANISM: Artificial Sequence
<220> FEATURE:
<223> OTHER INFORMATION: A synthetic primer

<400> SEQUENCE: 95
atacaaagct tccaccatga acggcgagga gcagtacta                           39

<210> SEQ ID NO 96
<211> LENGTH: 37
<212> TYPE: DNA
<213> ORGANISM: Artificial Sequence
<220> FEATURE:
<223> OTHER INFORMATION: A synthetic primer

<400> SEQUENCE: 96
atacactcga gtcatcgtgg ttcctgcggc cgccgag                             37

<210> SEQ ID NO 97
<211> LENGTH: 39
<212> TYPE: DNA
<213> ORGANISM: Artificial Sequence
<220> FEATURE:
<223> OTHER INFORMATION: A synthetic primer

<400> SEQUENCE: 97
atacaaagct tccaccatga atagtgagga gcagtacta                           39

<210> SEQ ID NO 98
<211> LENGTH: 39
<212> TYPE: DNA
<213> ORGANISM: Artificial Sequence
<220> FEATURE:

```
<223> OTHER INFORMATION: A synthetic primer

<400> SEQUENCE: 98
atacactcga gtcaccgggg ttcctgcggt cgcagtggc                              39

<210> SEQ ID NO 99
<211> LENGTH: 39
<212> TYPE: DNA
<213> ORGANISM: Artificial Sequence
<220> FEATURE:
<223> OTHER INFORMATION: A synthetic primer

<400> SEQUENCE: 99
atacaaagct tccaccatga cgcctcaacc ctcgggtgc                              39

<210> SEQ ID NO 100
<211> LENGTH: 39
<212> TYPE: DNA
<213> ORGANISM: Artificial Sequence
<220> FEATURE:
<223> OTHER INFORMATION: A synthetic primer

<400> SEQUENCE: 100
atacactcga gtcacagaaa atctgagaaa gccagactg                              39

<210> SEQ ID NO 101
<211> LENGTH: 39
<212> TYPE: DNA
<213> ORGANISM: Artificial Sequence
<220> FEATURE:
<223> OTHER INFORMATION: A synthetic primer

<400> SEQUENCE: 101
atacaaagct tccaccatgg cgcctcatcc cttggatgc                              39

<210> SEQ ID NO 102
<211> LENGTH: 39
<212> TYPE: DNA
<213> ORGANISM: Artificial Sequence
<220> FEATURE:
<223> OTHER INFORMATION: A synthetic primer

<400> SEQUENCE: 102
atacactcga gtcacaagaa gtctgagaac accagggtg                              39
```

DIFFERENTIATION OF NON-EMBRYONIC STEM CELLS TO CELLS HAVING A PANCREATIC PHENOTYPE

RELATED APPLICATION

This application claims priority from U.S. Provisional Application Ser. No. 60/726,750 filed Oct. 14, 2005.

STATEMENT OF GOVERNMENT RIGHTS

This invention was made with the assistance of government support under United States Grant No. U19 DK61244 from the National Institutes of Health. The government may have certain rights to the invention.

FIELD OF THE INVENTION

This invention relates to the field of non-embryonic multipotent stem cells, specifically to the use of non-embryonic multipotent stem cells to provide pancreatic cells and methods for producing and using them.

BACKGROUND OF THE INVENTION

Pancreas

The pancreas is an elongated, tapered organ which lies to the rear of the upper left hand side of the abdominal cavity. It has been anatomically described as containing three main sections including a head (widest end—located near the duodenum), a body, and a tail (tapered end—located near the spleen). This organ houses two main tissue types: exocrine tissue, comprised of both acinar and ductal cells; and endocrine tissue, containing cells which produce hormones (i.e., insulin) for delivery into the bloodstream. The exocrine pancreas, comprising about 95% of the pancreatic mass, is an acinar gland containing clusters of pyramidal secretory cells (referred to as acini) that produce digestive enzymes (i.e., amylase, lipase, phospholipase, trypsin, chymotrypsin, aminopeptidase, elastase and various other proteins). These enzymes are delivered to the digestive system by tubes constructed of cuboidal ductal cells, which also produce bicarbonate for digestive purposes. Between the secretory acini and ductal tubes is located a connecting cell component referred to as centroacinar cells.

The endocrine pancreas, comprising only about 1-2% of the pancreatic mass, contains clusters of hormone-producing cells referred to as islets of Langerhans (the islet cells are responsible for the maintenance of blood glucose levels by secreting insulin). These clusters are made up of at least seven cell types, including, but not limited to, insulin-producing β-cells, glucagon-producing α-cells, somatostatin-producing δ-cells, and PP-cells which produce pancreatic polypeptide (Edlund, H., 2002). In addition, a subpopulation of endocrine cells referred to as ϵ-cells recently has been described (Heller, R. S., et al., 2005). These cells were discovered based on their production of ghrelin, an appetite stimulating peptide known to be secreted by enteroendocrine cells of the digestive tract.

Transcriptional Cascade Underlying Endocrine Pancreas and β-Cell Differentiation Endoderm specification, foregut and midgut endoderm specification and subsequently pancreas specification are regulated by a complement of transcription factors (FIG. 1). Specifically, initial endoderm specification in the mouse involves expression of Sox17 (Kanai-Azuma, M. et al., 2002), as well as Gata-5 and Gata-6 (Weber, H. et al., 2000; Bossard, P., and Zaret, K. S. 1998) and Mixer/Mix.3 (Henry, G. L., and Melton, D. A. 1998). Subsequently, the hepatocyte nuclear factor, Hnf3β/Foxa2, is needed for the development of prospective foregut and midgut endoderm (Ang, S. L., et al., 1993). Other transcription factors then commit the foregut and midgut endoderm to liver, thyroid, lung, gastric, duodenal and pancreas endoderm.

In the mouse, pancreas is derived in part from the ventral and dorsal foregut endoderm, which subsequently fuse to form the mature organ. Commitment to the pancreas is associated with expression of the transcription factors Hlxb9 and Pdx-1. Deletion of Hlxb9 (Hentsch, B. et al., 1996) or Pdx-1 (Offield, M. F. et al., 1996) leads to dorsal or complete pancreas agenesis, respectively, even though a dorsal pancreas bud can be detected in Pdx-1 deficient embryos. Ventral pancreas formation is relatively normal in Hlxb9 deficient embryos, whereas dorsal pancreas specification is deficient.

These phenotypes suggest that initial specification is different between dorsal and ventral pancreas. As a pancreatic bud is still formed, despite the elimination of either transcription factor, other signals may be present before expression of Hlxb9 or Pdx-1 for pancreatic commitment. Further commitment to exocrine versus endocrine pancreas is associated with expression of Ptf1a/p48 (Ahlgren, U. et al., 1998) and Ngn3 (Gradwohl, G. et al., 2000), respectively. Of note, Ptf1a/p48 appears to also be needed earlier, i.e., during specification of the ventral pancreatic bud (Kawaguchi, Y. et al., 2002). Like Pdx-1, which is needed to specify pancreatic endoderm, Ngn3 is needed to specify pancreatic endoderm to the endocrine lineage, and it is believed that endocrine cells are derived from Ngn3 expressing cells. Ngn3 is also expressed in the central nervous systems (CNS), and deletion of this transcription factor not only affects endocrine pancreas development, but also nervous system development. Further commitment to β-cells in vivo is associated with expression of Pax4 (Sosa-Pineda, B. et al., 1997), Pax6 (Sander, M. et al., 1997), Nkx2.2 (Sussel, L. et al., 1998; accession number NM_002509 for human mRNA sequence) and Nkx6.1 (Sander, M. et al., 2000).

Extracellular Signals Underlying Endocrine Pancreas and β-Cell Differentiation

During development endoderm is specified by a combination of factors, including members of the TGFβ and Wnt family. Wnt3 is expressed in the primitive streak and developing mesoderm, and Wnt3 null mice do not form mesoderm or endoderm (Liu, P. et al., 1999). Nodal is expressed in the epiblast and in the anterior regions of the primitive streak (Zhou, X. et al., 1993), and like Wnt3 null embryos, Nodal null embryos also fail to develop mesoderm and endoderm. Using Xenopus animal cap assays, it was also shown that activin-A, another member of the TGF family, induces both mesoderm and endoderm specification in a dose dependent fashion, with high concentrations of activin-A inducing dorsal mesoderm and endoderm and low concentrations inducing ventral mesoderm (McDowell, N. et al., 1997).

Subsequent pancreas commitment and endocrine pancreas commitment is also regulated by members of the TGFβ and Wnt family, as well as by members of the FGF and hedgehog families. Compared with initial endoderm specification, which requires among other signals Wnt3, Wnts may inhibit pancreatic endoderm specification. Indeed, expression of Wnt1 or Wnt5a under the control of the Pdx-1 promoter alters the foregut region, which now resembles a posterior extension of the stomach rather than normally comprising the proximal duodenum, and is associated with reduction or complete agenesis of the pancreas. Consistent with this observation, several Wnt signaling inhibitors can be detected in the mouse embryonic pancreas, including sFRP-1, -2, -3 and -4 as well as Dkks (Heller, R. S. et al., 2002). Pancreas commitment from the ventral as well as dorsal forgut endoderm is inhibited by sonic hedgehog (SHH) (Hebrok, M. et al., 2000). Elimination of the SHH receptor, patched (Ptc), causes more widespread differentiation to pancreatic epithelium. It is thought that activin-A (Maldonado, T. S. et al., 2000) and/or FGF2 (Hardikar, A. A. et al., 2003) signals from the notochord act to repress SHH expression in pre-pancreatic endoderm.

Pancreas versus liver specification in the ventral gut endoderm is at least in part determined by FGF2 produced by the adjacent cardiac mesoderm (Jung, J. et al., 1999), which suppresses pancreas specification, whereas low doses of FGF2 may be important for pancreas differentiation from dorsal foregut endoderm (Hardikar, A. A. et al., 2003). In addition, pancreas specification and differentiation is regulated by Notch signaling (Jensen, J. et al., 2000). Elimination of Notch pathway components, such as Dll-1 or Hes-1, leads to accelerated differentiation to pancreas epithelium.

Endocrine versus exocrine pancreas differentiation is regulated by endoderm-mesoderm interactions (Gittes, G. K. et al., 1996), in part mediated by cell-extracellular matrix (ECM) interactions and by members of the BMP family of growth factors, including activin and TGFβ. Endodermal-mesenchymal interactions have a dual role in endocrine pancreas differentiation. These interactions are key between E9.5 and 10.5 for inducing pancreas commitment, whereas interactions between pancreas committed endoderm and laminin, produced by the mesenchyme subsequently steers differentiation into an exocrine phenotype (Sanvito, F. et al., 1994). In addition, TGFβ members, such as BMP2, produced by the mesenchyme, may prevent endocrine specification while favoring exocrine pancreas differentiation in vivo. FGFs produced by mesenchymal cells, such as FGF10, also play a role. FGF10 appears to play a role in proliferation of Pdx-1$^+$ pancreatic progenitors (Bhushan, A. et al., 2001).

Diabetes

Diabetes mellitus is a medical condition characterized by variable yet persistent high blood-glucose levels (hyperglycemia). Diabetes is a serious devastating illness that is reaching epidemic proportions in both industrialized and developing countries. In 1985, there were approximately 30 million people with diabetes worldwide, which increased 135 million in 1995 and is expected to increase further by close to 50% by 2050. Diabetes is the fifth leading cause of death in the United States. According to the American Diabetes Association, the economic cost of diabetes in the U.S. in 2002 was $132 billion, including $92 billion of direct costs. This figure is expected to reach in excess of $190 billion by 2020.

Generally, diabetes mellitus can be subdivided into two distinct types: Type 1 diabetes and Type 2 diabetes. Type 1 diabetes is characterized by little or no circulating insulin and it most commonly appears in childhood or early adolescence. It is caused by the destruction of the insulin-producing beta cells of the pancreatic islets. To survive, people with Type 1 diabetes must take multiple insulin injections daily and test their blood sugar multiple times per day. However, the multiple daily injections of insulin do not adequately mimic the body's minute-to-minute production of insulin and precise control of glucose metabolism. Blood sugar levels are usually higher than normal, causing complications that include blindness, renal failure, non-healing peripheral vascular ulcers, the premature development of heart disease or stroke, gangrene and amputation, nerve damage, impotence and it decreases the sufferer's overall life expectancy by one to two decades.

Type 2 diabetes usually appears in middle age or later and particularly affects those who are overweight. In Type 2 diabetes, the body's cells that normally require insulin lose their sensitivity and fail to respond to insulin normally. This insulin resistance may be overcome for many years by extra insulin production by the pancreatic beta cells. Eventually, however, the beta cells are gradually exhausted because they have to produce large amounts of excess insulin due to the elevated blood glucose levels. Ultimately, the overworked beta cells die and insulin secretion fails, bringing with it a concomitant rise in blood glucose to sufficient levels that it can only be controlled by exogenous insulin injections. High blood pressure and abnormal cholesterol levels usually accompany Type 2 diabetes. These conditions, together with high blood sugar, increase the risk of heart attack, stroke, and circulatory blockages in the legs leading to amputation.

There is a third type of diabetes in which diabetes is caused by a genetic defect, such as Maturity Onset Diabetes of the Young (MODY). MODY is due to a genetic error in the insulin-producing cells that restricts its ability to process the glucose that enters this cell via a special glucose receptor. Beta cells in patients with MODY cannot produce insulin correctly in response to glucose, resulting in hyperglycemia and require treatment that eventually also requires insulin injections.

The currently available medical treatments for insulin-dependent diabetes are limited to insulin administration, pancreas transplantation (either with whole pancreas or pancreas segments) and pancreatic islet transplantation. Insulin therapy is by far more prevalent than pancreas transplantation and pancreatic islet transplantation. However, controlling blood sugar is not simple. Despite rigorous attention to maintaining a healthy diet, exercise regimen, and always injecting the proper amount of insulin, many other factors can adversely affect a person's blood-sugar control including: stress, hormonal changes, periods of growth, illness or infection and fatigue. People with diabetes must constantly be prepared for life threatening hypoglycemic (low blood sugar) and hyperglycemic (high blood sugar) reactions.

In contrast to insulin administration, whole pancreas transplantation or transplantation of segments of the pancreas is known to have cured diabetes in patients. However, due to the requirement for life-long immunosuppressive therapy, the transplantation is usually performed only when kidney transplantation is required, making pancreas-only transplantations relatively infrequent operations. Although pancreas transplants are very successful in helping people with insulin-dependent diabetes improve their blood sugar to the point they no longer need insulin injections and reduce long-term complications, there are a number of drawbacks to whole pancreas transplants. Most importantly, getting a pancreas transplant involves a major operation and requires the use of life-long immunosuppressant drugs to prevent the body's immune system from destroying the pancreas that is a foreign graft. Without these drugs, the pancreas is destroyed in a matter of days. The risks in taking these immunosuppressive drugs is the increased incidence of infections and tumors that can both be life threatening.

Pancreatic islet transplants are much simpler and safer procedures than whole pancreas transplants and can achieve the same effect by replacing beta cells. However, the shortage of islet cells available for transplantation remains an unsolved problem in islet cell transplantation. Since islets form only about 2% of the entire pancreas, isolating them from the rest of the pancreas that does not produce insulin takes approximately 6 hours. Although an automated isolation method has made it possible to isolate enough islets from one pancreas to transplant into one patient, as opposed to the 5 or 6 organs previously needed to carry out one transplant, the demand for islets still exceeds the currently available supply of organs harvested from cadavers. Additionally, long term resolution of diabetic symptoms is often not achieved.

An alternative to insulin injections, pancreas transplantation and pancreatic islet transplantation would fulfill a great public health need.

Stem Cells

The embryonic stem (ES) cell has unlimited self-renewal and can differentiate into all tissue types. ES cells are derived from the inner cell mass of the blastocyst or primordial germ cells from a post-implantation embryo (embryonic germ cells or EG cells). ES (and EG) cells can be identified by positive staining with antibodies to SSEA 1 (mouse) and SSEA 4 (human). At the molecular level, ES and EG cells express a number of transcription factors specific for these undifferentiated cells. These include Oct-4 and rex-1. Rex expression depends on Oct-4. Also found are LIF-R (in mouse) and the transcription factors sox-2 and rox-1. Rox-1 and sox-2 are also expressed in non-ES cells. Another hallmark of ES cells is the presence of telomerase, which provides these cells with an unlimited self-renewal potential in vitro.

The ability to generate functional islet cells from a long-term expandable stem cell population would provide a source of β-cells for transplantation in patients with diabetes. One such population under consideration is embryonic stem (ES) cells. When embryonic stem cells are allowed to form embryoid bodies in vitro, rare cells with β-cell characteristics can be detected amongst the endodermal cell types. Recent studies have demonstrated that relative specific differentiation of mouse and human ES cells to hepatic or pancreatic endoderm may be possible. Treatment with high concentrations of activin has resulted in the specification of ES cells to endoderm (Kubo, A. et al., 2004). A number of studies have also suggested that insulin-positive cells can be obtained from ES cells using a number of different strategies (Lumelsky, N. et al., 2001; Hori, Y. et al., 2002; Soria, B. et al., 2000; Kahan, B. W. et al., 2003). However, some of these studies did not address whether insulin that was detected was insulin-1 or insulin-2, the latter also found in neural cells and extra-embryonic endoderm (Sipione S., et al., 2004). An additional complication is that most studies cultured ES cells in insulin containing medium, and several groups have now shown that insulin may be absorbed by cells from the medium (Vaca P. et al., 2005; Rajagopal J. et al., 2003; Hansson M. et al., 2004). An additional problem, to be overcome for ES cell-derived β-like cells to be used in the clinic, is the ability of undifferentiated ES cells, even when present in low numbers, to cause teratoma formation (Bjorklund et al., 2002).

As diabetes reaches an epidemic status worldwide, a need for novel and curative therapies is evident. With the advent of islet transplantation as a potential therapy for type-1 diabetes, the paucity of donor pancreata has become a limiting factor. Thus, there is a need for an abundant, clinically relevant, cell source for use as an alternative to insulin injections, pancreas transplantation and pancreatic islet transplantation.

"Multipotent adult progenitor cells" (MAPCs) are non-embryonic (non-ES), non-germ and non-embryonic germ (non-EG) cells that can differentiate into one or more ectodermal, endodermal and mesodermal cells types. MAPCs can be positive for telomerase, Oct-3A (Oct-3/4) or a combination thereof. Telomerase or Oct-3/4 have been recognized as genes that are primary products for the undifferentiated state. Telomerase is needed for self renewal without replicative senescence. MAPCs derived from human, mouse, rat or other mammals appear to be the only normal, non-malignant, somatic cell (i.e., non-germ cell) known to date to express telomerase activity even in late passage cells. The telomeres are not sequentially reduced in length in MAPCs. MAPCs are karyotypically normal. MAPCs may also express SSEA-4 and nanog.

The Oct-4 gene (Oct-3 in humans) is transcribed into at least two splice variants in humans, Oct-3A and Oct-3B. The Oct-3B splice variant is found in many differentiated cells, whereas the Oct-3A splice variant (also previously designated Oct 3/4) is reported to be specific for the undifferentiated embryonic stem cell (Shimozaki et al. 2003). Oct-4 (Oct-3 in humans) is a transcription factor expressed in the pregastrulation embryo, early cleavage stage embryo, cells of the inner cell mass of the blastocyst, and embryonic carcinoma (EC) cells (Nichols J., et al 1998), and is down-regulated when cells are induced to differentiate. Expression of Oct-4 plays an important role in determining early steps in embryogenesis and differentiation. Oct-4, in combination with Rox-1, causes transcriptional activation of the Zn-finger protein Rex-1, also required for maintaining ES in an undifferentiated state (Rosfjord and Rizzino A. 1997; Ben-Shushan E, et al. 1998). In addition, sox-2, expressed in ES/EC, but also in other more differentiated cells, is needed together with Oct-4 to retain the undifferentiated state of ES/EC (Uwanogho D et al. 1995). Maintenance of murine ES cells and primordial germ cells requires LIF.

MAPCs have the ability to regenerate all primitive germ layers (endodermal, mesodermal and ectodermal) in vitro and in vivo. In this context they are equivalent to embryonic stem cells and distinct from mesenchymal stem cells, which are also isolated from bone marrow. The biological potency of MAPCs has been proven in various animal models, including mouse, rat, and xenogeneic engraftment of human stem cells in rats or NOD/SCID mice (Reyes, M. and C. M. Verfaillie 2001; Jiang, Y. et al. 2002). Clonal potency of this cell population has been shown. Single genetically marked MAPCs were injected into mouse blastocysts, blastocysts implanted, and embryos developed to term (Jiang, Y. et al. 2002). Postnatal analysis in chimeric animals showed reconstitution of all tissues and organs, including liver. Dual staining experiments demonstrated that gene-marked MAPCs contributed to a significant percentage of apparently functional cardiomyocytes in these animals. These animals did not show any heart abnormalities or irregularities in either the embryological or adult state. No abnormalities or organ dysfunction were observed in any of these animals.

MAPCs are capable of extensive culture without loss of differentiation potential and show efficient, long term, engraftment and differentiation along multiple developmental lineages in NOD-SCID mice, without evidence of teratoma formation (Reyes, M. and C. M. Verfaillie 2001). This includes endothelial lineage differentiation (Verfaillie, 2002; Jahagirdar, et al. 2001).

SUMMARY OF THE INVENTION

One embodiment provides compositions and methods for providing insulin-expressing cells and their progenitors from non-embryonic stem, non-germ, non-embryonic germ cells that can differentiate into at least two of ectodermal, endodermal and mesodermal cell types. For example, when non-embryonic stem, non-germ, non-embryonic germ cells that can differentiate into at least two of ectodermal, endodermal and mesodermal cell types are exposed to Activin-A and a SHH inhibitor, cells with increased expression of Pdx-1 are produced. When these cells with increased Pdx-1 expression are exposed to EGF or HGF (or both), cells with increased expression of Ngn3 are produced. When these cells with increased Ngn3 expression are exposed to nicotinamde, exendin or both, cells with increased expression of insulin are produced. Accordingly, the invention is directed towards the following compositions and methods.

One embodiment provides a composition comprising a first agent, wherein the first agent is Activin-A, a second agent, wherein the second agent inhibits sonic hedgehog and non-embryonic stem, non-germ, non-embryonic germ cells that differentiate into at least two of ectodermal, endodermal and mesodermal cell types. The composition may also comprise BMP4.

Another embodiment provides a composition comprising EGF or HGF and cells having increased expression of Pdx-1, wherein the cells having increased expression of Pdx-1 are prepared by contacting non-embryonic stem, non-germ, non-embryonic germ cells that can differentiate into at least two of ectodermal, endodermal and mesodermal cell types with a first agent, wherein the first agent is Activin A, a second agent, wherein the second agent inhibits sonic hedgehog (SHH) activity, and, optionally BMP4, to yield cells having increased expression of Pdx-1.

Another embodiment provides a composition comprising one or both of nicotinamide or exendin4 and cells having increased expression of Ngn3, wherein the cells having increased expression of Ngn3 are prepared by a) contacting non-embryonic stem, non-germ, non-embryonic germ cells that can differentiate into at least two of ectodermal, endodermal and mesodermal cell types with a first agent, wherein the first agent is Activin A, a second agent, wherein the second agent inhibits sonic hedgehog (SHH) activity, and optionally BMP4, to yield cells having increased expression of Pdx-1 and b) contacting the cells having increased Pdx-1 expression with EGF or HGF to yield cells having increased expression of Ngn3. In one embodiment, the composition further comprises one or both of GDF11 or betacellulin.

Another embodiment provides a composition comprising cell culture medium or a pharmaceutically acceptable carrier and cells expressing insulin or having increased expression of insulin prepared by a) contacting non-embryonic stem, non-germ, non-embryonic germ cells that can differentiate into at least two of ectodermal, endodermal and mesodermal cell types with a first agent, wherein the first agent is Activin A, a second agent, wherein the second agent inhibits sonic hedgehog (SHH) activity, and optionally BMP4, to yield cells having increased expression of Pdx-1, b) contacting the cells having increased Pdx-1 expression with EGF or HGF to yield cells having increased expression of Ngn3 and c) contacting the cells having increased Ngn3 expression with one or both of nicotinamide or exendin4 to yield cells expressing insulin. In one embodiment, the cells having increased expression of Ngn3 are contacted with one or more of GDF11 or betacellulin.

In one embodiment, the composition comprises cell culture medium or a pharmaceutically acceptable carrier (e.g., a pharmaceutically acceptable medium). For example, one embodiment provides a composition comprising cells having increased expression of Pdx-1 or increased expression of Ngn3 and cell culture medium or a pharmaceutically acceptable carrier (e.g., a pharmaceutically acceptable medium). In one embodiment, the second agent is cyclopamine or an anti-SHH antibody.

One embodiment provides a method comprising contacting non-embryonic stem, non-germ, non-embryonic germ cells that can differentiate into at least two of ectodermal, endodermal and mesodermal cell types with a first agent, wherein the first agent is Activin A and a second agent, wherein the second agent inhibits sonic hedgehog (SHH) activity to yield cells having increased expression of Pdx-1. In one embodiment, the non-embryonic stem, non-germ, non-embryonic germ cells are also contacted with BMP4.

In one embodiment, the cells having increased Pdx-1 expression are contacted with EGF or HGF to yield cells having increased expression of Ngn3. In another embodiment, the cells having increased Ngn3 expression also have increased expression of NeuroD.

In one embodiment, the cells having increased expression of Ngn3 are contacted with one or both of nicotinamide or exendin4 to yield cells expressing insulin. In one embodiment, the expression of insulin is increased over the amount expressed by the Ngn3 expressing cells. In one embodiment, the cells having increased expression of Ngn3 are contacted with one or both of GDF11 or betacellulin.

One embodiment provides a method to differentiate non-embryonic stem, non-germ, non-embryonic germ cells that can differentiate into at least two of ectodermal, endodermal and mesodermal cell types comprising the steps of: a) contacting the non-embryonic stem, non-germ and non-embryonic germ cells with a first agent, wherein the first agent is Activin A (for about 1 to about 9 or more days, including about 3 or about 6 days), b) contacting the cells obtained from step a) with Activin-A and a second agent, wherein the second agent inhibits sonic hedgehog activity (for about 1 to about 9 or more days, including about 3 or about 6 days); c) contacting the cells obtained from step b) with EGF or HGF (for about 1 to about 9 or more days, including about 6 days); and d) contacting the cells obtained from step c) with one or both of nicotinamide or exendin4 (for about 1 to about 9 days or more, including about 6 days) to yield cells expressing insulin. In one embodiment, step a), step b) or both further comprise contacting the cells with BMP4. In another embodiment, step d) further comprises contacting the cells with one or both of GDF11 or betacellulin. In one embodiment, the second agent is cyclopamine or an anti-SHH antibody.

In one embodiment, the contacting is carried out in vitro (e.g., in culture). In one embodiment, the contacting is sequential. In one embodiment, the contacting is simultaneous. In one embodiment, the cells expressing insulin or having increased expression of insulin secrete insulin (e.g., insulin-1), c-peptide or a combination thereof.

In one embodiment, the non-embryonic stem, non-germ, non-embryonic germ cells are mammalian cells (e.g., human cells). In another embodiment, the non-embryonic stem, non-germ, non-embryonic germ cells (or their differentiated progeny) are transduced with a pancreatic transcription factor. In one embodiment, the pancreatic transcription factor comprises Ngn3, NeuroD, Pdx-1, Pax4, Ptf1a/p48, Pax6, Nk6.1, Nkx2.2 or a combination thereof. In another embodiment, the pancreatic transcription factor comprises Pdx-1, Ngn3 or a combination thereof.

One embodiment provides a method to provide pancreatic cells to a subject in need thereof comprising: a) contacting non-embryonic stem, non-germ, non-embryonic germ cells that can differentiate into at least two of ectodermal, endodermal and mesodermal cell types with a first agent, wherein the first agent is Activin A and a second agent, wherein the second agent inhibits sonic hedgehog (SHH) activity to yield cells having increased expression of Pdx-1; and b) administering the cells having increased expression of Pdx-1 so as to provide pancreatic cells in the subject. In one embodiment, the non-embryonic stem, non-germ, non-embryonic germ cells are also contacted with BMP4.

In another embodiment, the cells having increased expression of Pdx-1 are contacted with EGF or HGF to yield cells having increased expression of Ngn3 prior to administration to the subject.

In another embodiment, the cells having increased expression Ngn3 are contacted with one or both of nicotinamide or exendin4 to yield cells expressing insulin or having increased expression of insulin, prior to administration to the subject. In one embodiment, the cells having increased expression Ngn3 are contacted with one or both of GFD11 or betacellulin.

Another embodiment provides a method to provide insulin expressing cells to a subject in need thereof comprising: a) contacting non-embryonic stem, non-germ, non-embryonic germ cells that can differentiate into at least two of ectodermal, endodermal and mesodermal cell types with a first agent, wherein the first agent is Activin A; b) contacting the cells obtained from step a) with Activin-A and a second agent, wherein the second agent inhibits sonic hedgehog activity; c) contacting the cells obtained from step b) with EGF or HGF; d) contacting the cells obtained from step c) with one or both of nicotinamide or exendin4 so as to yield cells expressing insulin or having increased expression of insulin; and e) administering the cells expressing insulin or having increased expression of insulin to the subject. In one embodiment, step a), step b) or both further comprise BMP-4. In another embodiment, step d) further comprises one or both of GDF11 or betacellulin.

In one embodiment, the subject is a mammal (e.g., a human). In another embodiment, the subject has a pancreatic disorder or injury. In one embodiment, the disorder comprises diabetes, obesity, pancreatic atresia, pancreas inflammation, alpha1-antitrypsin deficiency, hereditary pancreatitis, pancreatic cancer, pancreatic enzyme deficiency or hyperinsulinism. In one embodiment, the diabetes is Type I or Type II diabetes. In another embodiment, the injury is a result of physical trauma, chemical, radiation, aging, disease or combination thereof.

One embodiment provides the use of cells prepared by the methods described herein to prepare a medicament to treat a pancreatic disorder or injury. In one embodiment, the medicament further comprises a physiologically acceptable carrier or cell culture medium.

BRIEF DESCRIPTION OF THE DRAWINGS

FIG. 2 depicts the phenotype of low-$O_2$ mouse MAPCs. mMAPCs were derived and maintained at 5% $O_2$. (A) Some clones have Oct-4 mRNA expression at levels between 5 and 40% of embryonic stem cells (which is >1,000 fold higher than in MAPCs isolated under normoxic (20% $O_2$) conditions). (B) This is confirmed by FACS for Oct-4 protein and by intracellular staining for Oct-4. Compared to ES cells, MAPCs express Oct-4, Rex-1, Fbx15, FoxD3, Egs1, Dnmt31 and Ecat7 at ES levels, but not Nanog, Sox-2, Fgf4, Utf1, Eras, Ecat1 and GDF3. Low-$O_2$ derived mouse MAPCs are Sca1, Thy1, CD34, CD31, MHC-class I and II, CD44 negative, but cKit positive. Although mouse MAPCs express Oct-4 mRNA at levels similar to ESCs, they do not form embryoid bodies or teratomas ($5 \times 10^6$ MAPCs grafted under the skin of 5 nude mice). When MAPCs isolated under normoxic conditions are subsequently switched to 5% $O_2$ conditions, no changes in transcriptional or cell surface phenotype are seen, suggesting that the isolation under low $O_2$ may select for a more primitive cell population and that the phenotype is not inducible in vitro.

DETAILED DESCRIPTION OF THE INVENTION

Definitions

Figure 1:
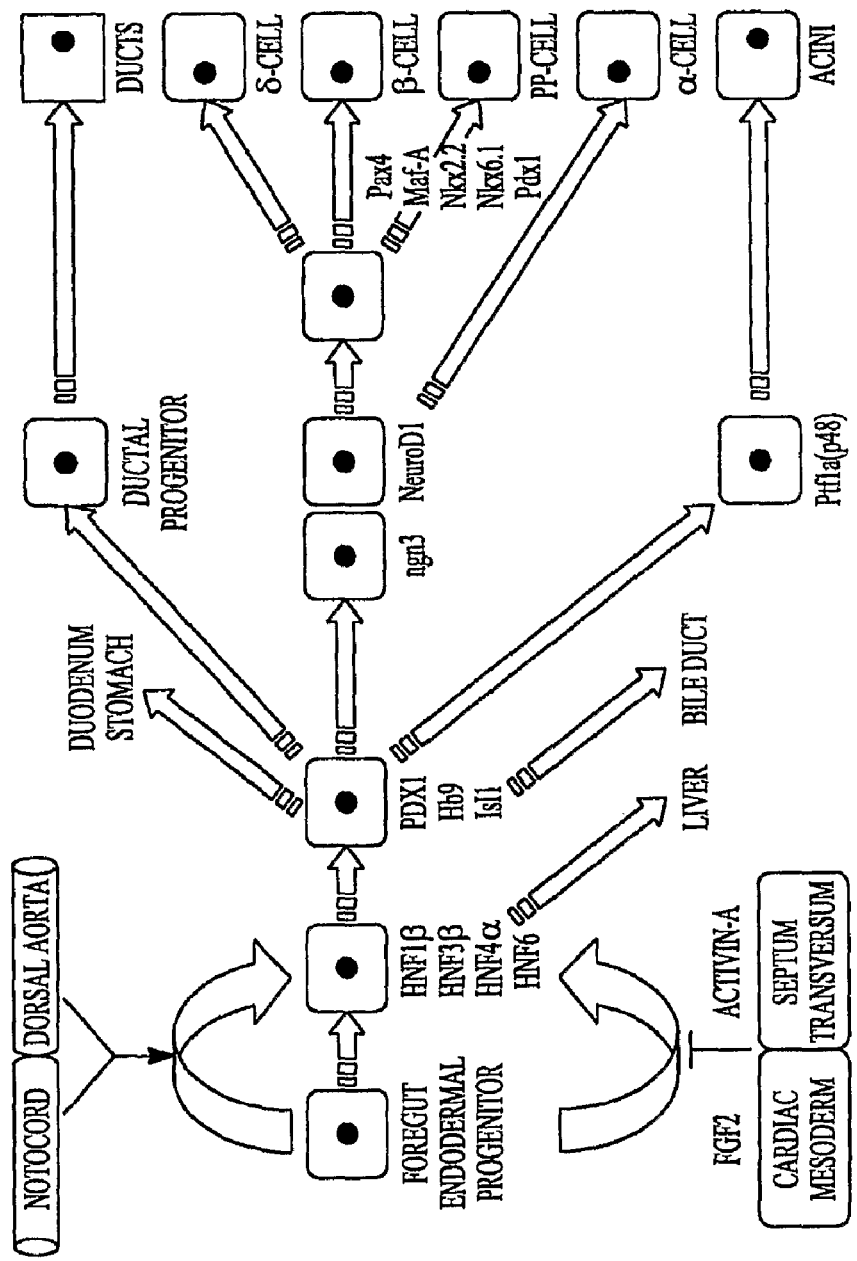
FIG. 1 depicts the regulation of endoderm specification, foregut and midgut endoderm specification and subsequently pancreas specification by a complement of specific transcription factors.

As used herein, the terms below are defined by the following meanings:

"MAPC" is an acronym for "multipotent adult progenitor cell." It is used herein to refer to a non-embryonic stem (non-ES), non-germ, non-embryonic germ (non-EG) cell that can give rise to (differentiate into) cell types of more than one embryonic lineage. It can form cell lineages of at least two germ layers (i.e., endoderm, mesoderm and ectoderm) upon differentiation. The term "adult," with respect to MAPC is non-restrictive. It refers to a non-embryonic somatic cell.

"Multipotent" refers to the ability to give rise to cell types of more than one embryonic lineage. "Multipotent," with respect to MAPC, is non-restrictive. MAPCs can form cell lineages of all three primitive germ layers (i.e., endoderm, mesoderm and ectoderm). The term "progenitor" as used in the acronym "MAPC" does not limit these cells to a particular lineage.

"Expansion" refers to the propagation of cells without differentiation.

"Progenitor cells" are cells produced during differentiation of a stem cell that have some, but not all, of the characteristics of their terminally-differentiated progeny. Defined progenitor cells, such as "pancreatic progenitor cells," are committed to a lineage, but not to a specific or terminally-differentiated cell type.

"Self-renewal" refers to the ability to produce replicate daughter cells having differentiation potential that is identical to those from which they arose. A similar term used in this context is "proliferation."

"Increased expression" of a marker (e.g., Pdx-1, Ngn3, NeuroD or insulin 1) refers to an increase (in mRNA and/or protein) relative to the parent cell (a cell prior to the recited treatment (e.g., contacting with Activin-A) and/or treatments) on an average per cell basis (for example, if the parent cell does not express a marker and the progeny does, there is an increase in expression; or if the progeny expresses more of the marker compared to the parent cell there is also an increase in expression). For example, increased expression of a marker (e.g., Pdx-1) can be an increase in expression of up to about 1.01 fold, about 1.015 fold, about 1.02 fold, about 1.025 fold, about 1.03 fold, about 1.035 fold, about 1.04 fold, about 1.045 fold, about 1.05 fold, about 1.055 fold, about 1.06 fold, about 1.065 fold, about 1.07 fold, about 1.075 fold, about 1.08 fold, about 1.85 fold, about 1.9 fold, about 1.95 fold, about 2 fold (e.g., 2×), about 3 fold, about 4 fold, about 5 fold, about 6 fold, about 7 fold, about 8 fold, about 9 fold, about 10 fold, about 15 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 600 fold, about 700 fold, about 800 fold, about 900 fold, about 1,000 fold, about 2,000 fold, about 3,000 fold, about 4,000 fold, about 5,000 fold, about 6,000 fold, about 7,000 fold, about 8,000 fold, about 9,000 fold, about 10,000 fold, about 15,000 fold, about 20,000 fold, about 25,000 fold, about 30,000 fold, about 35,0000 fold, about 40,000 fold, about 50,000 fold, about 60,000 fold, about 65,000 fold, about 70,000 fold, about 75,000 fold, about 80,000 fold, about 85,000 fold, about 90,000 fold, about 100,000 fold or greater as compared to the parent cell (on an average per cell basis).

An effective amount of an agent (e.g., Activin-A, an agent that inhibits SHH, EGF, HGF, nicotinamide, exendin4, GDF11 or betacellulin) is an amount effective to differentiate the cells as recited, when applied alone or in combination with one or more other agents.

"Engraft" or "engraftment" refers to the process of cellular contact and incorporation into an existing tissue or site of interest. In one embodiment, greater than about 5%, greater than about 10%, greater than about 15%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95% or about 100% of administered MAPCs or progeny derived therefrom engraft in the pancreas or other tissues.

Persistence refers to the ability of cells to resist rejection and remain or increase in number over time (e.g., days, weeks, months, years) in vivo. Thus, by persisting, the MAPC or progeny can populate the pancreas or other tissues or remain in vivo, such as in barrier devices or other encapsulated forms.

"Immunologic tolerance" refers to the survival (in amount and/or length of time) of foreign (e.g., allogeneic or xenogeneic) tissues, organs or cells in recipient subjects. This survival is often a result of the inhibition of a graft recipient's ability to mount an immune response that would otherwise occur in response to the introduction of foreign cells. Immune tolerance can encompass durable immunosuppression of days, weeks, months or years. Included in the definition of immunologic tolerance is NK-mediated immunologic tolerance. This term also encompasses instances where the graft is tolerant of the host.

The term "isolated" refers to a cell or cells which are not associated with one or more cells or one or more cellular components that are associated with the cell or cells in vivo. An "enriched population" refers to a relative increase in numbers of the cell of interest, such as MAPCs, relative to one or more other cell types, such as non-MAPC cell types, in vivo or in primary culture.

"Cytokines" refer to cellular factors that induce or enhance cellular movement, such as homing of MAPCs or other stem cells, progenitor cells or differentiated cells. Cytokines may also stimulate such cells to divide or differentiate.

A "subject" or cell source can be a vertebrate, including a mammal, such as a human. Mammals include, but are not limited to, humans, farm animals, sport animals and companion animals. In included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird.

As used herein, "treat," "treating" or "treatment" includes treating, reversing, preventing, ameliorating, or inhibiting an injury or disease-related condition or a symptom of an injury or disease-related condition.

An "effective amount" generally means an amount which provides the desired effect. For example, an effective dose is an amount sufficient to effect a beneficial or desired result, including a clinical result. The dose can be administered in one or more administrations and can include any preselected amount of cells. The precise determination of what would be considered an effective dose may be based on factors individual to each subject, including size, age, injury or disease being treated and amount of time since the injury occurred or the disease began. One skilled in the art, particularly a physician, would be able to determine the number of cells that would constitute an effective dose. Doses can vary depending on the mode of administration, e.g., local or systemic; free or encapsulated. The effect can be engraftment or other clinical endpoints, such as reversal or treatment of diabetes. Other effects can include providing beta cells, recruiting endogenous cells, effecting angiogenesis, and/or providing pancreatic progenitors.

"Co-administer" can include sequential, simultaneous and/or separate administration of two or more agents.

To provide pancreatic cells in a subject, several routes are possible. In one embodiment MAPCs can be administered and allowed to provide pancreatic cells in vivo. This can occur, as described herein, by differentiation of the MAPCs themselves or by other means, such as by recruitment of endogenous cells. Alternatively, more mature cells can be administered, these cells having been differentiated ex vivo from MAPC. Such cells include progeny at all stages of differentiation, including pancreatic progenitor cells that can give rise to mature pancreatic cell types, committed progenitor cells that cannot form every one of those types, and further differentiated types, which can include beta-cells.

The terms "comprises", "comprising", and the like can have the meaning ascribed to them in U.S. Patent Law and can mean "includes", "including" and the like. As used herein, "including" or "includes" or the like means including, without limitation.

MAPCs

MAPCs are non-embryonic (non-ES), non-germ and non-embryonic germ (non-EG) cells that can differentiate into ectodermal, endodermal and mesodermal cells types. MAPCs can be positive for telomerase. They can also be positive for Oct-3A (Oct-3/4). MAPCs can differentiate in vivo where they can form pancreatic cells, such as beta-cells. Alternatively, MAPCs can be differentiated ex vivo into progeny cells with pancreatic phenotypes. MAPCs or their differentiated progeny can be administered to a subject.

Human MAPCs from bone marrow are described in U.S. Pat. No. 7,015,037 (PCT/US00/21387 (published as WO 01/11011)) and U.S. patent application Ser. No. 10/467,963 (PCT/US02/04652 (published as WO 02/064748)), the contents of which are incorporated herein by reference for their description of MAPCs. MAPCs have been identified in other mammals. Murine MAPCs, for example, are also described in U.S. Pat. No. 7,015,037 and U.S. patent application Ser. No. 10/467,963, the contents of which are incorporated herein by reference for their description of murine MAPCs. Rat MAPCs are also described in Ser. No. 10/467,963, the contents of which are incorporated herein by reference for their description of rat MAPCs. Swine MAPCs are described in Patent Application No. PCT/US2005/038979, the contents of which are incorporated herein by reference for their description of swine MAPCs. Cynomologous monkey MAPCs are described in Clavel et al. (2005) the contents of which are incorporated herein by reference for their description of cynomologous monkey MAPCs.

Isolation and Growth

Methods of MAPC isolation for humans and mouse are described in U.S. Pat. No. 7,015,037 (PCT/US00/21387 (published as WO 01/11011)) and for rat in U.S. patent application Ser. No. 10/467,963 (PCT/US02/04652 (published as WO 02/064748)), and these methods, along with the characterization of MAPCs disclosed therein, are incorporated herein by reference.

MAPCs were initially isolated from bone marrow, but were subsequently established from other tissues, including brain and muscle (Jiang, Y., et al., 2002). Thus, MAPCs can be isolated from multiple sources, including, but not limited to, bone marrow, placenta, umbilical cord and cord blood, muscle, brain, liver, spinal cord, blood or skin. For example, MAPCs can be derived from bone marrow aspirates, which can be obtained by standard means available to those of skill in the art (see, for example, Muschler, G. F., et al., 1997; Batinic, D., et al., 1990). It is therefore now possible for one of skill in the art to obtain bone marrow aspirates, brain or liver biopsies and other organs, and isolate the cells using positive or negative selection techniques available to those of skill in the art, relying upon the genes that are expressed (or not expressed) in these cells (e.g., by functional or morphological assays, such as those disclosed in the above-referenced applications, which have been incorporated herein by reference for teaching such assays).

MAPCs from Human Bone Marrow as Described in U.S. Pat. No. 7,015,037

Bone marrow mononuclear cells were derived from bone marrow aspirates, which were obtained by standard means available to those of skill in the art (see, for example, Muschler, G. F. et al. 1997; Batinic, D. et al. 1990). Multipotent adult stem cells are present within the bone marrow (or other organs such as liver or brain), but do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of $CD45^+$ and $Gly-A^+$ cells, and the remaining approximately 0.1% of marrow mononuclear cells were then recovered. Cells can also be plated in fibronectin-coated wells and cultured as described below for 2-4 weeks to deplete the cell population of $CD45^+$ and $Gly-A^+$ cells.

Alternatively, positive selection can be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by, for example, Schwartz, et al., in U.S. Pat. No. 5,759,793 (magnetic separation), Basch et al. 1983 (immunoaffinity chromatography), and Wysocki and Sato 1978 (fluorescence-activated cell sorting).

Recovered $CD45^-/GlyA^-$ cells were plated onto culture dishes coated with about 5-115 ng/ml (about 7-10 ng/ml can be used) serum fibronectin or other appropriate matrix coating. Cells were maintained in Dulbecco's Minimal Essential Medium (DMEM) or other appropriate cell culture medium, supplemented with about 1-50 ng/ml (about 5-15 ng/ml can be used) platelet-derived growth factor-BB (PDGF-BB), about 1-50 ng/ml (about 5-15 ng/ml can be used) epidermal growth factor (EGF), about 1-50 ng/ml (about 5-15 ng/ml can be used) insulin-like growth factor (IGF), or about 100-10,000 IU (about 1,000 IU can be used) LIF, with about $10^{-10}$ to about $10^{-8}$ M dexamethasone or other appropriate steroid, about 2-10 µg/ml linoleic acid, and about 0.05-0.15 µM ascorbic acid. Other appropriate media include, for example, MCDB, MEM, IMDM and RPMI. Cells can either be maintained without serum, in the presence of about 1-2% fetal calf serum, or, for example, in about 1-2% human AB serum or autologous serum.

When re-seeded at about $2 \times 10^3$ cells/cm$^2$ about every 3 days, >40 cell doublings were routinely obtained, and some populations underwent >70 cell doublings. Cell doubling time was about 36-48 h for the initial 20-30 cell doublings. Afterwards cell-doubling time was extended to as much as 60-72 h.

Telomere length of MAPCs from 5 donors (age about 2 years to about 55 years) cultured at re-seeding densities of about $2 \times 10^3$ cells/cm$^2$ for about 23-26 cell doublings was between about 11-13 KB. This was about 3-5 KB longer than telomere length of blood lymphocytes obtained from the same donors. Telomere length of cells from 2 donors evaluated after about 23 and about 25 cell doublings, respectively, and again after about 35 cells doublings, was unchanged. The karyotype of these MAPCs was normal.

Phenotype of Human MAPCs under Conditions Described in U.S. Pat. No. 7,015,037

Immunophenotypic analysis by FACS of human MAPCs obtained after about 22-25 cell doublings showed that the cells do not express CD31, CD34, CD36, CD38, CD45, CD50, CD62E and -P, HLA-DR, Muc18, STRO-1, cKit, Tie/Tek; and express low levels of CD44, HLA-class I and β-micro globulin, and express CD10, CD13, CD49b, CD49e, CDw90, F1k1 (N>10).

Once cells underwent >40 doublings in cultures re-seeded at about $2 \times 10^3$ cells/cm$^2$, the phenotype became more homogenous and no cell expressed HLA class-I or CD44 (n=6). When cells were grown at higher confluence, they expressed high levels of Muc18, CD44, HLA class I and β-microglobulin, which is similar to the phenotype described for MSC(N=8) (Pittenger, 1999).

Immunohistochemistry showed that human MAPCs grown at about $2 \times 10^3$ cells/cm$^2$ seeding density express EGF-R, TGF-R1 and -2, BMP-R1A, PDGF-R1A and -B, and that a small subpopulation (between about 1 and about 10%) of MAPCs stain with anti-SSEA4 antibodies (Kannagi, R 1983).

Using Clontech cDNA arrays the expressed gene profile of human MAPCs cultured at seeding densities of about $2 \times 10^3$ cells/cm$^2$ for about 22 and about 26 cell doublings was determined:

A. MAPCs did not express CD31, CD36, CD62E, CD62P, CD44-H, cKit, Tie, receptors for IL1, IL3, IL6, IL11, G CSF, GM-CSF, Epo, F1t3-L, or CNTF, and low levels of HLA-class-I, CD44-E and Muc-18 mRNA.

B. MAPCs expressed mRNA for the cytokines BMP1, BMP5, VEGF, HGF, KGF, MCP1; the cytokine receptors F1k1, EGF-R, PDGF-R1β; gp130, LIF-R, activin-R1 and -R2, TGFR-2, BMP-R1A; the adhesion receptors CD49c, CD49d, CD29; and CD10.

C. MAPCs expressed mRNA for hTRT and TRF1; the POU domain transcription factor Oct-4, sox-2 (required with Oct-4 to maintain undifferentiated state of ES/EC, Uwanogho D. 1995), sox 11 (neural development), sox 9 (chondrogenesis) (Lefebvre V. 1998); homeodeomain transcription factors: Hoxa4 and -a5 (cervical and thoracic skeleton specification; organogenesis of respiratory tract) (Packer, A. I. 2000), Hox-a9 (myelopoiesis) (Lawrence, H. 1997), D1x4 (specification of forebrain and peripheral structures of head) (Akimenko, M. A. 1994), MSX1 (embryonic mesoderm, adult heart and muscle, chondro- and osteogenesis) (Foerst-Potts, L. 1997), PDX1 (pancreas) (Offield, M. F. 1996).

D. Presence of Oct-4, LIF-R, and hTRT mRNA was confirmed by RT-PCR.

E. In addition, RT-PCR showed that Rex-1 mRNA and Rox-1 mRNA were expressed in MAPCs.

MAPCs were also demonstrated to be CD105 and CD106 negative.

Oct-4, Rex-1 and Rox-1 were expressed in MAPCs derived from human and murine marrow and from murine liver and brain. Human MAPCs expressed LIF-R and stained positive with SSEA-4. Finally, Oct-4, LIF-R, Rex-1 and Rox-1 mRNA levels were found to increase in human MAPCs cultured beyond 30 cell doublings, which resulted in phenotypically more homogenous cells. In contrast, MAPCs cultured at high density lost expression of these markers. This was associated with senescence before about 40 cell doublings and loss of differentiation to cells other than chondroblasts, osteoblasts and adipocytes.

Culturing MAPCs as Described in U.S. Pat. No. 7,015,037

MAPCs isolated as described herein can be cultured using methods disclosed herein and in U.S. Pat. No. 7,015,037, which is incorporated by reference for these methods.

Briefly, for the culture of MAPCs, culture in low-serum or serum-free medium was preferred to maintain the cells in the undifferentiated state. Medium used to culture the cells, as described herein, was supplemented as described in Table 1. Human MAPCs do not require LIF.

TABLE 1

| | |
|---|---|
| Insulin | about 10-50 μg/ml (about 10 μg/ml)* |
| Transferrin | about 0-10 μg/ml (about 5.5 μg/ml) |
| Selenium | about 2-10 ng/ml (about 5 ng/ml) |
| Bovine serum albumin (BSA) | about 0.1-5 μg/ml (about 0.5 μg/ml) |
| Linoleic acid | about 2-10 μg/ml (about 4.7 μg/ml) |
| Dexamethasone | about 0.005-0.15 μM (about 0.01 μM) |
| L-ascorbic acid 2-phosphate | about 0.1 mM |
| Low-glucose DMEM (DMEM-LG) | about 40-60% (about 60%) |
| MCDB-201 | about 40-60% (about 40%) |
| Fetal calf serum | about 0-2% |
| Platelet-derived growth | about 5-15 ng/ml (about 10 ng/ml) |
| Epidermal growth factor | about 5-15 ng/ml (about 10 ng/ml) |
| Insulin like growth factor | about 5-15 ng/ml (about 10 ng/ml) |
| Leukemia inhibitory factor | about 10-10,000IU (about 1,000 IU) |

*Preferred concentrations are shown in parentheses.

Addition of about 10 ng/mL LIF to human MAPCs did not affect short-term cell growth (same cell doubling time till 25 cell doublings, level of Oct 4 (Oct 3/4) expression). In contrast to what was seen with human cells, when fresh murine marrow mononuclear cells, depleted on day 0 of CD45$^+$ cells, were plated in MAPC culture, no growth was seen. When murine marrow mononuclear cells were plated, and cultured cells 14 days later depleted of CD45$^+$ cells, cells with the morphology and phenotype similar to that of human MAPCs appeared. This suggested that factors secreted by hematopoietic cells were needed to support initial growth of murine MAPCs. When cultured with PDGF-BB and EFG alone, cell doubling was slow (>6 days) and cultures could not be maintained beyond about 10 cell doublings. Addition of about 10 ng/mL LIF significantly enhanced cell growth.

Once established in culture, cells can be frozen and stored as frozen stocks, using DMEM with about 40% FCS and about 10% DMSO. Other methods for preparing frozen stocks for cultured cells are also available to those of skill in the art.

Thus, MAPCs can be maintained and expanded in culture medium that is available to the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®. Many media are also available as a low-glucose formulation, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements, and bovine embryonic fluid. It is understood that sera can be heat-inactivated at about 55-65° C. if deemed necessary to inactivate components of the complement cascade.

Additional supplements can also be used advantageously to supply the cells with the trace elements for optimal growth and expansion. Such supplements include insulin, transferrin, sodium selenium and combinations thereof. These components can be included in a salt solution such as, but not limited to Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine and L-valine. It is well within the skill of one in the art to determine the proper concentrations of these supplements.

Antibiotics are also typically used in cell culture to mitigate bacterial, mycoplasmal and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin and zeocin. Antibiotic and antimycotic additives can be of some concern, depending on the type of work being performed. One possible situation that can arise is an antibiotic-containing media wherein bacteria are still present in the culture, but the action of the antibiotic performs a bacteriostatic rather than bacteriocidal mechanism. Also, antibiotics can interfere with the metabolism of some cell types.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others.

Also contemplated is the use of feeder cell layers. Feeder cells are used to support the growth of fastidious cultured cells, including stem cells. Feeder cells are normal cells that have been inactivated by γ-irradiation. In culture, the feeder layer serves as a basal layer for other cells and supplies cellular factors without further growth or division of their own (Lim, J. W. and Bodnar, A., 2002). Examples of feeder layer cells are typically human diploid lung cells, mouse embryonic fibroblasts, Swiss mouse embryonic fibroblasts, but can be any post-mitotic cell that is capable of supplying cellular components and factors that are advantageous in allowing optimal growth, viability and expansion of stem cells. In many cases, feeder cell layers are not necessary to keep the ES cells in an undifferentiated, proliferative state, as leukemia inhibitory factor (LIF) has anti-differentiation properties. Therefore, supplementation with LIF can be used to maintain MAPC in some species in an undifferentiated state.

Cells in culture can be maintained either in suspension or attached to a solid support, such as extracellular matrix components and synthetic or biopolymers. Stem cells often require additional factors that encourage their attachment to a solid support, such as type I, type II and type IV collagen, concanavalin A, chondroitin sulfate, fibronectin, "superfibronectin" and fibronectin-like polymers, gelatin, laminin, poly-D and poly-L-lysine, thrombospondin and vitronectin.

The maintenance conditions of stem cells can also contain cellular factors that allow stem cells, such as MAPCs, to remain in an undifferentiated form. It is advantageous under conditions where the cell must remain in an undifferentiated state of self-renewal for the medium to contain epidermal growth factor (EGF), platelet derived growth factor (PDGF), leukemia inhibitory factor (LIF; in selected species), and combinations thereof. It is apparent to those skilled in the art that supplements that allow the cell to self-renew but not differentiate should be removed from the culture medium prior to differentiation.

Stem cell lines and other cells can benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing are selected based on the type of lineage one skilled in the art wishes to induce, and it is within the capabilities of the skilled artisan to select the appropriate cells for co-culture.

Differentiation of MAPCs to Pancreatic Cells

MAPCs and pancreatic progenitor cells differentiated from MAPCs are useful as a source of pancreatic cells. The maturation, proliferation and differentiation of MAPCs may be effected through culturing MAPCs with appropriate factors including, but not limited to, activin-A (or other members TGFβ family), BMP4 (or other members of the BMP family), an agent that inhibits sonic hedgehog activity (including, but not limited to, cyclopamine and anti-SHH antibody), EGF or HGF (or other mitogenic proteins), nicotinamide (and possibly nicotinic acid), exendin (including, but not limited to, exendin 4 and exenatide (a 39-amino acid peptide which closely resembles exendin-4), GDF11 (or other members of the bone morphogenetic protein/transforming growth factor beta (BMP/TGFbeta) superfamily), betacellulin, or with stromal cells or other cells which secrete factors responsible for stem cell regeneration, commitment and differentiation.

An agent that inhibits sonic hedgehog (SHH) activity (e.g., signaling) includes any agent (e.g., a peptide, protein, including antibodies, small molecule, drug, chemical, or nucleic acid, such as DNA or RNA) which inhibits the function or expression of sonic hedgehog (including, but not limited to, providing signal(s) in the patterning of the early embryo, such as patterning of the ventral neural tube, the anterior-posterior limb axis, and the ventral somites). Such agents include, but are not limited to, an anti-sonic hedgehog antibody, cyclopamine (CPA), analogs thereof, such as cyclopamine-4-ene-3-one or other steroidal alkaloids. As used herein, "inhibit" refers to a reduction (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100%) in the activity of sonic hedgehog as compared to the activity of SHH in the absence of an agent that inhibits SHH activity.

As described in Example 2 herein below, MAPCs were differentiated into pancreatic progenitor cells and beta-cells in vitro. Briefly, MAPCs were cultured in medium containing Activin-A (about 0.5 ng/mL to about 200 ng/mL, such as about 50 ng/mL to about 100 ng/mL), BMP-4 (about 10 ng/mL to about 100 ng/mL, such as about 20 ng/mL to about 30 ng/mL or about 50 ng/mL) for about 3 days, followed by about six days of culture in Activin A, BMP-4 and cyclopamine (e.g., about 5 to about 50 µM, including about 10 µM) or an anti-SHH antibody (about 10 µg/mL) for about six days. The cells obtained therefrom were next cultured in medium containing EGF (e.g., about 5 to about 100 ng/mL, including about 50 ng/mL) or HGF (e.g., about 5 to about 100 ng/mL, including about 50 ng/mL) for about 6 days. The cells obtained therefrom were then cultured in medium containing nicotinamide (about 5 µM to about 50 µM, including about 10 µM) or exendin4 (e.g., about 5 nM to about 50 nM, including about 10 nM), GFD11 (e.g., about 10 ng/mL to about 100 ng/mL, including about 50 ng/mL), and betacellulin (e.g., about 10 ng/mL to about 100 ng/mL, including about 50 ng/mL) for about six days.

Additional factors to enhance the initial commitment of MAPCs to pancreatic endoderm (Pdx-1 positive cells on day 9) can include factors known to play a role in endoderm commitment, such as members of the Wnt family, TGF-β family, and FGF family. Wnt-3 plays a role in endoderm specification. (Heller et al., 2002), as Wnt3$^{-/-}$ mice do not form endoderm or mesoderm (Heller et al., 2002). Pancreatic, but not hepatic, endoderm specification is regulated by members of the Wnt family. Compared with initial endoderm specification, which may depend on Wnt-3, Wnts may inhibit pancreatic endoderm specification. Dickkopf related protein 1 (Dkk-1), a member of the Dkk protein family of secreted proteins, antagonizes the canonical Wnt pathway by direct high-affinity binding to the Wnt coreceptor LRP5/6 and inhibiting interaction of LRP5/6 with the Wnt-Frizzled complex (Nusse 2001). Thus, addition of Dkk-1 or an inhibitor of β-catenin (e.g., a GSK3 inhibitor such as GSKSp inhibitor IX) (Willert et al., 1998) can increase the frequency of Pdx-1 positive progenitors generated from MAPCs.

Nodal also plays a role in endoderm specification, as Nodal$^{-/-}$ mice do not form endoderm or mesoderm. BMP-4, and other TGF family members, induces mesoderm rather than endoderm specification, as BMP-4$^{-/-}$ embryos die early in gestation without forming any organized mesoderm (Winnier et al., 1995). In vitro studies in which ES cell differentiation to endoderm is evaluated, demonstrated that Activin-A at high concentrations specifies cells to endoderm but not mesoderm. In subsequent steps needed for pancreatic endoderm specification (Kubo et al., 2004; D'Amour et al., 2005), Activin-A (Maldonado et al., 2000) alone or combined with bFGF (Hardikar et al., 2003) inhibits SHH expression, which prevents pancreatic endoderm specification.

FGF-8 may play a role in initial endoderm specification. Similarly, FGF-4 has been identified, at least in chicken, to play a role in endoderm specification (Wells et al., 2000). The role of FGF-2 in pancreas vs. liver specification is more complex. As indicated above FGF-2 inhibits SHH production (Hardikar et al., 2003; Jung et al., 1999), which should lead to pancreas specification. Thus, FGF-8, FGF4, FGF-2 or combination thereof can be used in the method to differentiate MAPCs (also in combination with other factors mentioned herein).

Pancreas commitment from the ventral as well as dorsal foregut endoderm is inhibited by sonic hedgehog (SHH) (Hebrok et al., 2000). Activin-A (Maldonado et al., 2000) and/or FGF-2 (Hardikar et al., 2003) signals from the notochord act to repress SHH expression in pre-pancreatic endoderm. Alternatively, or in addition, SHH can be blocked with cyclopamine, or specific anti-SHH antibodies.

Pancreas specification and differentiation is regulated by Notch signaling at multiple steps (Hardikar et al., 2003). Specifically, Notch signaling prevents commitment to pancreas, to endocrine pancreas and maturation of endocrine Ngn3 pancreatic progenitors. Thus, inhibitors of Notch signaling can be using in the methods to differentiate MAPCs.

Although some experiments indicted that the combination of activin-A and BMP4 was superior to activin-A alone, to induce Pdx-1 expression, BMP4 may be responsible for the mesodermal cells that are also present in culture. Thus, BMP4 many not be necessary, may be substituted with BMP2 or BMP7, or may be used at lower concentrations or with BMP-4 for only a few days followed by Activin-A alone. Additionally, Activin-A combined with Wnt-3 for the initial three days of differentiation may further enhance endoderm differentiation. As Wnts may inhibit pancreatic endoderm differentiation, addition of Wnt-3 followed by Dkk-1 may induce greater numbers of Pdx-1 positive cells by day 9. This can be confirmed by adding a GSK3 inhibitor that blocks the canonical Wnt pathway. The efficacy of Dkk-1 or GSK3 inhibitor can be demonstrated by measuring levels of phosphorylated β-catenin. Subsequently, the role of different FGFs (FGF-8, FGF-4, and FGF-2), by addition of graded doses of FGF-8 and/or FGF-2 and graded doses of FGF-4 and/or an inhibitor of FGF-2 (e.g., SU5402) can be determined. Additionally, inhibiting Notch signaling, for example, by using an inhibitor of γ-secretase (compound E, Calbiochem) can affect pancreatic endoderm (Pdx-1$^+$ cell) induction. The efficacy of the γ-secretase can be assessed by evaluating expression of Hes1 and Herp.

In one embodiment, the cells are transfected with a pancreatic transcription factor, including, but not limited to, Ngn3, NeuroD, Pdx-1, Pax4, Ptf1a/p48, Pax6, Nkx6.1, Nkx2.2 or a combination thereof, for example, by DNA, RNA or viral transfection or by protein transduction. Expression of these transcription factors can induce pancreatic differentiation of MAPCs. Additionally, the endogenous factor can be activated or increased in the cell by methods know in the art (e.g., homolgous recombination (e.g., U.S. Pat. No. 5,641, 670), non-homologus recombination (e.g., U.S. Pat. No. 6,602,686; RAGE (Random Activation of Gene Expression) technology; Athersys, Inc. (Cleveland, Ohio)), or other endogenous expression techniques available to the art worker (the above mentioned patents are incorporated by reference for teaching of methods of endogenous gene activation). In addition to the factors/genes described herein, variants, homologs or orthologs of the factors/genes, which have the same biological function/acitivty, can be used or assayed for in methods of the invention. For example, variants, homolog or orthologs of use in the present invention may be homologous or have sequence identity (nucleotide or amino acid sequence) with factors/genes involved pancreagenesis, including those factors/genes provided herein. Assays and programs to determine if a factor/gene is homolgous is are known in the art.

Methods of identifying and subsequently separating differentiated cells from their undifferentiated counterparts can be carried out by methods well known in the art and described herein. Cells that have been induced to differentiate can be identified by selectively culturing cells under conditions whereby differentiated cells outnumber undifferentiated cells. Similarly, differentiated cells can be identified by morphological changes and characteristics that are not present on their undifferentiated counterparts, such as cell size, the number of cellular processes, the complexity of intracellular organelle distribution, and the production of insulin or C-peptide and the secretion of insulin or C-peptide in response to glucose.

Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different (increased or decreased expression of mRNA or protein) from undifferentiated cells, such as insulin-1, insulin-2, glucagon, somatostatin, NeuroD1, Pdx-1, Ngn3, Nkx6.1, Nkx2.2. Reverse-transcription polymerase chain reaction (RT-PCR) can be used to monitor such changes in gene expression during differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. A preferred embodiment of the invention envisions the use of FACS to identify and separate cells based on cell-surface antigen expression.

Additional Culture Methods

The density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2,000 cells/cm$^2$. The density can vary between species. Additionally, optimal density can vary depending on culture conditions and source of cells. It is within the skill of the ordinary artisan to determine the optimal density for a given set of culture conditions and cells.

Also, in specific embodiments the atmospheric oxygen concentration for isolating, culturing, expanding and/or differentiation of cells includes oxygen concentrations between about 0.1% to about 10% oxygen. In other embodiments, the atmospheric oxygen concentration includes oxygen concentrations between about 1% to about 9%. In other embodiments, the atmospheric oxygen concentration includes oxygen concentrations between about 1.5% to about 8%. In additional embodiments, the atmospheric oxygen concentrations include oxygen concentrations between about 2% to about 7% oxygen.

The above ranges are exemplary ranges of atmospheric oxygen concentrations to be used in the culture of non-ES, non-EG, non-germ cells that are Oct3/4 positive and can differentiate into ectodermal, endodermal, and mesodermal cell types and it should be understood that those of skill in the art will be able to employ oxygen concentrations falling within any of these ranges. Thus, one of skill in the art could set the oxygen culture concentrations at about 0.1%, 0.5%, 0.5%, 2%, 2.5%, 3%, 3.5%, 4%, 4.5%, 5%, 5.5%, 6%, 6.5%, 7%, 7.5%, 8%, 8.5%, 9%, 9.5%, 10%, or any other oxygen concentration between any of these percentages. In one embodiment, the oxygen concentration is about 2% to about 7%, such about 5%, which more closely approximates physiological oxygen concentrations (Guyton and Hall, in *Textbook of Medical Physiology*, W.B. Saunders Co., Philadelphia, pp. 513-523 (1996)). The oxygen concentration can be varied within a given range during the culturing period. The remainder of the atmospheric gases are conventional, inert gases, e.g., nitrogen, argon and the like, as well as carbon dioxide. Additionally, the cells of the invention are cultured in about 5% to about 6% $CO_2$.

Isolating and culturing MAPCs at 5% $O_2$ was shown to result in fewer cytogenetic abnormalities. Additionally, it resulted in a slight change in the phenotype of MAPCs. When rodent MAPCs are isolated and maintained at 5% $O_2$, Oct-4 transcript levels approach those of embryonic stem (ES) cells (50-80%), and >90% of cells express nuclear Oct-4 protein by immunohistochemistry. 5%-$O_2$ derived rodent MAPCs also express Rex-1 at levels approaching that of ES cells. Although mouse MAPCs expressed Oct-4 mRNA at levels similar to ES cells, they did not form embryoid bodies or teratomas ($5 \times 10^6$ MAPCs grafted under the skin of 5 nude mice).

MAPCs can also be cultured in the presence of a GSK3 inhibitor (e.g., a 6-bromoindirubin compound, including but not limited to, 6-bromoindirubin-3'-oxime (also known as BIO); incorporated herein by reference are U.S. Provisional Patent Application Nos. 60/703,823 (filed Jul. 29, 2005) and 60/704,169 (filed Jul. 29, 2005) and PCT applications PCT/US2006/029736 (filed Jul. 31, 2006) and PCT/US2006/029547 (filed Jul. 31, 2006) for the disclosure of culturing cells in the present of a GSK3 inhibitor).

Use of MAPCs and Progeny Therefrom

The pancreatic progenitor or beta-cells of the invention and/or the MAPCs can be used to repopulate a pancreas by either direct introduction into the area of damage or by systemic administration, which allows the cells to home to the area of damage. Accordingly, the invention provides methods of treating a subject in need of pancreatic cells comprising administering to a subject an effective amount of the pancreatic progenitor cells of the invention or MAPCs.

For the purposes described herein, either autologous, allogeneic or xenogeneic cells can be administered to a patient, either in undifferentiated, terminally differentiated or in a partially differentiated form, genetically altered or unaltered, by direct introduction to a site of interest, e.g., on or around the surface of an acceptable matrix, or systemically, in combination with a pharmaceutically acceptable carrier so as to repair, replace or promote the growth of existing and/or new pancreatic cells.

Generally, the invention provides methods to treat a pancreatic disorder. The term "pancreatic disorder" or "pancreatic disease" refers to a state where pancreatic function is impaired. Examples of "pancreatic disorders" or "pancreatic diseases" that can be treated with the compositions and methods of the invention include, but are not limited to, diabetes (including Type 1, Type 2, MODY and other genetic causes of diabetes), obesity, pancreatic atresia, pancreas inflammation, alpha1-antitrypsin deficiency, acute, chronic or hereditary pancreatitis, pancreatic cancer (including endocrine tumors of the pancreas), pancreas malfunction due to cystic fibrosis or Shwachman Diamond syndrome, pancreatic insufficiency or pancreatic enzyme deficiency, pancreatic cysts, hyperinsulinism, pancreatic digestive diseases, genetic disorders of the exocrine pancreas and pancreatic injury, including, but not limited to, injury as a result of physical trauma (including, but not limited to, surgery), chemical, radiological, aging, and/or disease.

Administration of MAPCs or Their Differentiated Progeny

MAPCs, or their differentiated progeny, can be administered to a subject by a variety of methods available to the art, including but not limited to localized injection, catheter administration, systemic injection, intraperitoneal injection, parenteral administration, intra-arterial injection, intravenous injection, transvascular injection, intramuscular injection, surgical injection into a tissue of interest (e.g., injection into the pancreas) or via direct application to tissue surfaces (e.g., during surgery or on a wound).

MAPCs can be administered either peripherally or locally through the circulatory system. "Homing" of stem cells would concentrate the implanted cells in an environment favorable to their growth and function. Pre-treatment of a patient with cytokine(s) to promote homing is another alternative contemplated in the methods of the present invention. Certain cytokines (e.g., cellular factors that induce or enhance cellular movement, such as homing of MAPCs or other stem cells, progenitor cells or differentiated cells) can enhance the migration of MAPCs or their progeny. Cytokines include, but are not limited to, stromal cell derived factor-1 (SDF-1), stem cell factor (SCF), angiopoietin-1, placenta-derived-growth factor (PlGF) and granulocyte-colony stimulating factor (G-CSF). Cytokines also include any which promote the expression of endothelial adhesion molecules, such as ICAMs, VCAMs and others, which facilitate the homing process.

Viability of newly forming tissues can be enhanced by angiogenesis. Factors promoting angiogenesis include, but are not limited to, VEGF, aFGF, angiogenin, angiotensin-1 and -2, betacellulin, bFGF, Factor X and Xa, HB-EGF, PDGF, angiomodulin, angiotropin, angiopoetin-1, prostaglandin E1 and E2, steroids, heparin, 1-butyryl-glycerol and nicotinic amide.

Factors that decrease apoptosis can also promote the formation of new tissue, such as pancreatic tissues. Factors that decrease apoptosis include but are not limited to β-blockers, angiotensin-converting enzyme inhibitors (ACE inhibitors), AKT, HIF, carvedilol, angiotensin II type 1 receptor antagonists, caspase inhibitors, cariporide and eniporide.

Exogenous factors (e.g., cytokines, differentiation factors (e.g., cellular factors, such as growth factors or angiogenic factors that induce lineage commitment), angiogenesis factors and anti-apoptosis factors) can be administered prior to, after or concomitantly with MAPCs or their differentiated progeny. For example, a form of concomitant administration would comprise combining a factor of interest in the MAPC suspension media prior to administration. Administrations are variable and may include an initial administration followed by subsequent administrations.

A method to potentially increase cell survival is to incorporate MAPCs or progeny into a biopolymer or synthetic polymer. Depending on the patient's condition, the site of injection might prove inhospitable for cell seeding and growth because of scarring or other impediments. Examples of biopolymer include, but are not limited to, fibronectin, fibrin, fibrinogen, thrombin, collagen and proteoglycans. This can be constructed with or without included cytokines, differentiation factors, angiogenesis factors or anti-apoptosis factors. Additionally, these can be in suspension. Another alternative is a three-dimensional gel with cells entrapped within the interstices of the cell biopolymer admixture. Again cytokines, differentiation factors, angiogenesis factors, anti-apoptosis factors or a combination thereof can be included within the gel. These can be deployed by injection via various routes described herein.

The cells can also be encapsulated with a capsule that is permeable to nutrients and oxygen while allowing appropriate cellular products (for example, insulin in the case of islet cells) to be released into the bloodstream or to adjacent tissues. In one embodiment, the capsular material is restrictive enough to exclude immune cells and antibodies that could reject and destroy the implant. Such encapsulation can be achieved using, for example, polymers (Chang, 2000). Such polymeric encapsulation systems include, but are not limited to, alginate (e.g., alginate bead), polysaccharide hydrogels, chitosan, calcium or barium alginate, a layered matrix of alginate and polylysine, a photopolymerizable poly(ethylene glycol) (PEG) polymer (Novocell, Inc.), a polyanionic material termed Biodritin (U.S. Pat. No. 6,281,341), polyacrylates, a photopolymerizable poly(ethylene glycol) polymer, and polymers such as hydroxyethyl methacrylate methyl methacrylate.

Another approach to encapsulate cells involves the use of photolithography techniques adapted from the semiconductor industry to encapsulate living cells in silicon capsules that have pores only a few nanometers wide (Desai 2002).

Also, suitable immune-compatible polycations, including but not limited to, poly-1-lysine (PLL) polycation or poly-1-ornithine or poly(methylene-co-guanidine) hydrochloride, may be used to encapsulate cells.

Additionally, cells can be encapsulated with biocompatible semipermeable membranes to surround encapsulated cells, sometimes within a capillary device, to create a miniature artificial organ, such as one that would include functional pancreas or liver cells (e.g., a liver or pancreatic artificial device). This is often called macroencapsulation. The membrane lets glucose, oxygen, and insulin pass in and out of the blood stream, and preferably keeps out the antibodies and T cells of the immune system, which may destroy the cells (e.g., islets). Such membranes can be used in a perfusion device, a capsule that is grafted to an artery where it males direct contact with the body's circulating blood; in this way, the device can draw nutrients from the blood and release insulin to circulate throughout the body. Another method provides for coating a small group of islet cells (macroencapsulation) or individual islet cells (microencapsulation) and implanting them inside the abdominal cavity. In these devices nutrients and insulin would be exchanged by way of the body fluids permeating the tissues in which they are implanted.

The quantity of cells to be administered will vary for the subject being treated. In a preferred embodiment, between about $10^4$ to about $10^8$, more preferably about $10^5$ to about $10^7$ and most preferably, about $3\times10^7$ stem cells and optionally, about 50 to about 500 µg/kg per day of a cytokine can be administered to a human subject. However, the precise determination of what would be considered an effective dose may be based on factors individual to each patient, including their size, age, disease or injury, amount of damage, amount of time since the damage occurred and factors associated with the mode of delivery (direct injection—lower doses, intravenous—higher doses). Dosages can be readily ascertained by those skilled in the art from this disclosure and the knowledge in the art.

An issue regarding the use of stem cells or their progeny is the purity of the enriched or isolated cell population. Bone marrow cells, for example, comprise mixed populations of cells, which can be purified to a degree sufficient to produce a desired effect. Those skilled in the art can readily determine the percentage of MAPCs or progeny in a population using various well-known methods, such as fluorescence activated cell sorting (FACS). Preferable ranges of purity in populations comprising MAPCs, or their differentiated progeny, are about 50-55%, about 55-60%, and about 65-70%. More preferably the purity is about 70-75%, about 75-80%, about 80-85%; and most preferably the purity is about 85-90%, about 90-95%, and about 95-100%. However, populations with lower purity can also be useful, such as about 25-30%, about 30-35%, about 35-40%, about 40-45% and about 45-50%. Purity of MAPCs or their progeny can be determined according to the gene expression profile within a population. Dosages can be readily adjusted by those skilled in the art (e.g., a decrease in purity may require an increase in dosage).

The skilled artisan can readily determine the amount of cells and optional additives, vehicles, or carrier in compositions to be administered in methods of the invention. Typically, additives (in addition to the active stem cell(s) or cytokine(s)) are present in an amount of about 0.001 to about 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine therefore: toxicity, such as by determining the lethal dose (LD) and $LD_{50}$ in a suitable animal model e.g., a rodent, such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. Additionally, the time for sequential administrations can be ascertained without undue experimentation.

When administering a therapeutic composition of the present invention, it can generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used should be compatible with the cells.

Sterile injectable solutions can be prepared by incorporating the cells utilized in practicing the present invention in the required amount of the appropriate solvent with various amounts of the other ingredients, as desired.

In one embodiment, MAPCs, or differentiated progeny thereof, can be administered initially, and thereafter maintained by further administration of MAPCs or differentiated progeny thereof. For instance, MAPCs can be administered by one method of injection, and thereafter further administered by a different or the same type of method.

It is noted that human subjects are treated generally longer than canines or other experimental animals, such that treatment has a length proportional to the length of the disease process and effectiveness. The doses may be single doses or multiple doses over a period of several days. Thus, one of skill in the art can scale up from animal experiments, e.g., rats, mice, canines and the like, to humans, by techniques from this disclosure and documents cited herein and the knowledge in the art, without undue experimentation. The treatment generally has a length proportional to the length of the disease process and treatment effectiveness and the subject being treated.

Examples of compositions comprising MAPCs, or differentiated progeny thereof, include liquid preparations for administration, including suspensions, and, preparations for direct or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations, without undue experimentation.

Compositions are conveniently provided as liquid preparations, e.g., isotonic aqueous solutions, suspensions, emulsions or viscous compositions, which may be buffered to a selected pH. Liquid preparations are normally easier to prepare than gels, other viscous compositions and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (preferably purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions, if desired, can be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected and the desired viscosity. Viscous compositions are normally prepared from solutions by the addition of such thickening agents.

A pharmaceutically acceptable preservative or cell stabilizer can be employed to increase the life of the compositions. Preferably, if preservatives are necessary, it is well within the purview of the skilled artisan to select compositions that will not affect the viability or efficacy of the MAPCs or progeny as described in the present invention.

Those skilled in the art will recognize that the components of the compositions should be selected to be chemically inert. This will present no problem to those skilled in chemical and pharmaceutical principles, or problems can be readily avoided by reference to standard texts or simple experiments (not involving undue experimentation), from this disclosure and the documents cited herein.

Compositions can be administered in dosages and by techniques available to those skilled in the medical and veterinary arts taking into consideration such factors as the age, sex, weight and condition of the particular patient, and the composition form used for administration (e.g., solid vs. liquid). Dosages for humans or other animals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, can be ascertained by the skilled artisan, from this disclosure, the documents cited herein, and the knowledge in the art.

Approaches for Transplantation to Prevent Immune Rejection

In some embodiments, it may be desired that the MAPCs (or differentiated progeny) be treated or otherwise altered prior to transplantation/administration in order to reduce the risk of stimulating host immunological response against the transplanted cells. Any method known in the art to reduce the risk of stimulating host immunological response may be employed. The following provides a few such examples.

1. Universal donor cells: MAPCs can be manipulated to serve as universal donor cells. Although undifferentiated MAPCs do not express MHC-I or -II antigens, some differentiated progeny may express one or both of these antigens. MAPCs can be modified to serve as universal donor cells by eliminating MHC-I or MHC-II antigens, and potentially introducing the MHC-antigens from the prospective recipient so that the cells do not become easy targets for NK-mediated killing, or become susceptible to unlimited viral replication or malignant transformation. Elimination of MHC-antigens can be accomplished, for example, by homologous recombination or by introduction of point-mutations in the promoter region or by introduction of a point mutation in the initial exon of the antigen to introduce a stop-codon, such as with chimeroplasts. Transfer of the host MHC-antigen(s) can be achieved by retroviral, lentiviral, adeno associated virus or other viral transduction or by transfection of the target cells with the MHC-antigen cDNAs.

2. Intrauterine transplant to circumvent immune recognition: MAPCs can be used in an intrauterine transplantation setting to correct genetic abnormalities, or to introduce cells that will be tolerated by the host prior to immune system development. This can be used to make human cells in large quantities in animals or it can be used to correct human embryo genetic defects by transplanting cells that make the correct protein or enzyme.

3. Hematopoietic Chimerism and Tolerance Induction

Benefit can be achieved through use of a stem cell, capable of reconstituting the immune system, which did not carry risk of graft-versus-host response. The graft-versus-host reaction is due to contaminating T cells inherent in the bone marrow graft. Although purification of hematopoietic stem cells from bone marrow is routine, their successful engraftment in the patient requires accompaniment by accessory T cells. Thus, a critical balance must be achieved between the beneficial engraftment value of T cells and the detrimental effect of graft-versus-host response.

MAPCs and ES cells represent a stem cell population which can be delivered without risk of graft-versus-host reactivity, as they can be expanded free of hematopoietic cell types, including T cells. This greatly reduces clinical risk. The transient elimination of NK cell activity during the acute phase of cell delivery increases the frequency of primitive stem cell engraftment and hematopoietic reconstitution to a clinically useful threshold without risk of long term immunosuppression.

As MAPC or ES engraft and contribute to hematopoiesis, the newly formed T cells undergo thymic and peripheral self versus non-self education consistent with host T cells as described above. Co-exposure of newly created naïve T cells of donor and host origin results in reciprocal depletion of reactive cells; hence tolerance to T cells expressing allogeneic antigens derived from a MAPC or ES donor can be achieved. A patient can thus be rendered tolerant to the cellular and molecular components of the MAPC or ES donor immune system, and would accept a cell, tissue or organ graft without rejection.

4. Natural Killer (NK) Cell Function:

Any means, such as an agent, which inhibits NK cell function, including depleting NK cells from a population of cells, may also be administered to prevent immune rejection, increase engraftment or increase immune tolerance. Such an agent includes an anti-NK cell antibody, irradiation or any other method which can inhibit NK cell function. NK function inhibition is further described in PCT Application No. PCT/US2005/015740, filed May 5, 2005, which application is incorporated herein by reference for teaching methods of inhibiting NK cells to aid in stem cell persistence in vivo.

In one embodiment of the invention at least one means for inhibiting NK cell function, including inhibition of NK cell-mediated cytotoxicity, is administered. NK cell function can be negated by NK depletion using either genetic (recipients deficient in NK cells) or epigenetic (in vivo depletion/inactivation with, for example, an anti-NK antibody) means. Any material capable of inhibiting NK cell function can be used (e.g., multimeric compounds that bind to P-Selectin Glycoprotein 1 (PSGL-1) on the surface of T cells or NK cells (U.S. Pat. Pub. No. 2004/0116333) or modulation of SH2-containing inositol phophatase (SHIP) expression or function (U.S. Pat. Pub. No. 2002/0165192)). Any means/agent including, but not limited to, chemical (e.g., a chemical compound, including, but not limited to, a pharmaceutical, drug, small molecule), protein (e.g., anti-NK cell antibody), peptide, microorganism, biologic, nucleic acid (including genes coding for recombinant proteins, or antibodies), or genetic construct (e.g., vectors, such as expression vectors, including but not limited to expression vectors which lead to expression of an antagonist against NK cell activity) can be used to inhibit NK cell function.

There are several antibodies available in the art which inhibit NK cell function, including, but not limited to, anti-human thymocyte globulin (ATG; U.S. Pat. No. 6,296,846), TM-β1 (anti-IL-2 receptor β chain Ab), anti-asialo-GM1 (immunogen is the glycolipid GA1), anti-NK1.1 antibodies or monoclonal anti-NK-cell antibodies (5E6; Pharmingen, Piscataway, N.J.). Additionally, antibodies directed against, for example, a natural cytotoxicity receptor (NCR), including, for example, NKp46, or an antibodies directed against a leukocyte-associated Ig like receptor family, including, for example, LAIR-1, or antibodies directed against a member of the killer cell immunoglobulin-like receptor (KIR) family, including, for example, KIR2DL1, KIR2DL2 or KR2DL3 are available to the art worker or can be made by methods available to an art worker and are useful in the present invention.

Additionally, a means, such as an agent which can cross-link LAIR-1 molecules on NK cells may be used to inhibit NK cell function. Also, irradiation (lethal, sub-lethal, and/or localized irradiation) may be used to inhibit NK cell function.

In one embodiment, the means for inhibiting NK cell function is an antibody which is reactive with Natural Killer cells. Additionally, a means for inhibiting NK cell function can include agents that modulate the immune system, such as those developed for immunosuppression. It should be noted that any of these means/agents can be used alone or in combination.

Thus, there is also provided herein a method to increase immunologic tolerance in a subject to MAPCs and other cells comprising administering a population of the MAPCs and an effective amount of an agent for inhibiting Natural Killer cell function to the subject, so that immunologic tolerance to the MAPCs increases compared to the method without administration of the inhibiting agent.

5. Gene Therapy:

MAPCs can be extracted and isolated from the body, grown in culture in the undifferentiated state or induced to differentiate in culture, and genetically altered using a variety of techniques, especially viral transduction. Uptake and expression of genetic material is demonstrable, and expression of foreign DNA is stable throughout development. Retroviral and other vectors for inserting foreign DNA into stem cells are available to those of skill in the art. (Mochizuki, H. et al. 1998; Robbins, P. et al. 1997; Bierhuizen, M. et al. 1997; Douglas, J. et al. 1999; Zhang, G. et al. 1996). Once transduced using a retroviral vector, enhanced green fluorescent protein (eGFP) expression persists in terminally differentiated muscle cells, endothelium and c-Kit positive cells derived from isolated MAPCs, demonstrating that expression of retroviral vectors introduced into MAPC persists throughout differentiation. Terminal differentiation was induced from cultures initiated with about 10 eGFP$^+$ cells previously transduced by retroviral vector and sorted a few weeks into the initial MAPC culture period.

Monitoring of Subject After Administration of MAPCs or Progeny Therefrom

Following transplantation, the growth or differentiation of the administered MAPCs or progeny or the therapeutic effect of the MAPCs or progeny may be monitored. For example, blood glucose, serum glucose and/or serum insulin may be monitored.

Following administration, the immunological tolerance of the subject to the MAPCs or progeny may be tested by various methods known in the art to assess the subject's immunological tolerance to MAPCs. In cases where the subject's tolerance of MAPCs is suboptimal (e.g., the subject's immune system is rejecting the exogenous MAPCs), therapeutic adjunct immunosuppressive treatment, which is known in the art, of the subject may be performed.

Genetically-Modified MAPCs or Differentiated Progeny Derived Therefrom

MAPCs or differentiated progeny derived therefrom can be genetically altered ex vivo, eliminating one of the most significant barriers for gene therapy. For example, a subject's bone marrow aspirate is obtained, and from the aspirate MAPCs are isolated. The MAPCs are then genetically altered to express one or more desired gene products (e.g., pancreatic genes, including, but not limited to, insulin, glucagon, somatostatin or any of the various genes which code for digestive enzymes produced by the pancreas). The MAPCs can then be screened or selected ex vivo to identify those cells which have been successfully altered, and these cells can be introduced into the subject or can be differentiated and introduced into the subject, either locally or systemically. Alternately, MAPCs can be differentiated and then the differentiated cells can be genetically altered prior to administration. In either case, the cells provide a stably-transfected source of cells that can express a desired gene product. Especially where the patient's own tissue, such as bone marrow, is the source of the MAPCs, this method provides an immunologically safe method for producing cells for transplant.

Methods for Genetically Altering MAPCs or Differentiated Progeny

Cells isolated by the methods described herein, or their differentiated progeny, can be genetically modified by introducing DNA or RNA into the cell by a variety of methods available to those of skill in the art. These methods are generally grouped into four major categories: (1) viral transfer, including the use of DNA or RNA viral vectors, such as retroviruses, including lentiviruses (Mochizuki, H., et al., 1998; Martin, F., et al. 1999; Robbins, et al. 1997; Salmons, B. and Gunzburg, W. H., 1993; Sutton, R., et al., 1998; Kafri, T., et al., 1999; Dull, T., et al., 1998), Simian virus 40 (SV40), adenovirus (see, for example, Davidson, B. L., et al., 1993; Wagner, E., et al., 1992; Wold, W., *Adenovirus Methods and Protocols*, Humana Methods in Molecular Medicine (1998), Blackwell Science, Ltd.; Molin, M., et al., 1998; Douglas, J., et al., 1999; Hofmann, C., et al., 1999; Schwarzenberger, P., et al., 1997), alpha virus, including Sindbis virus (U.S. Pat. No. 5,843,723; Xiong, C., et al., 1989; Bredenbeek, P. J., et al., 1993; Frolov, I., et al., 1996), herpes virus (Laquerre, S., et al., 1998) and bovine papillomavirus, for example; (2) chemical transfer, including calcium phosphate transfection and DEAE dextran transfection methods; (3) membrane fusion transfer, using DNA-loaded membranous vesicles such as liposomes (Loeffler, J. and Behr, J., 1993), red blood cell ghosts and protoplasts, for example; and (4) physical transfer techniques, such as microinjection, microprojectile J. Wolff in "Gene Therapeutics" (1994) at page 195. (see J. Wolff in "Gene Therapeutics" (1994) at page 195; Johnston, S. A., et al., 1993; Williams, R. S., et al., 1991; Yang, N. S., et al., 1990), electroporation, nucleofection or direct "naked" DNA transfer.

Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids or PNAs), or by ribozyme technology, for example. Insertion of one or more pre-selected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure relating to methods of non-homologous recombination.

The desired gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA, as described by Sebestyen, et al. (1998), to direct the DNA to the nucleus for more efficient expression.

The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) in specific cell compartments (including, but not limited to, the cell membrane).

Any of transfection or transduction technique can also be applied to introduce a transcriptional regulatory sequence into MAPCs or progeny to activate a desired endogenous gene. This can be done by both homologous (e.g., U.S. Pat. No. 5,641,670) or non-homologous (e.g., U.S. Pat. No. 6,602,686) recombination. These patents are incorporated by reference for teaching of methods of endogenous gene activation.

Successful transfection or transduction of target cells can be demonstrated using genetic markers, in a technique that is known to those of skill in the art. The green fluorescent protein of *Aequorea Victoria*, for example, has been shown to be an effective marker for identifying and tracking genetically modified hematopoietic cells (Persons, D., et al., 1998). Alternative selectable markers include the β-Gal gene, the truncated nerve growth factor receptor, drug selectable markers (including but not limited to NEO, MTX, hygromycin).

Protein Transduction

Proteins can be transferred directly to cells when they are linked to a protein transduction domain (PTD), small cationic peptide domains that can freely and rapidly cross cell membranes. Several PTDs such as poly-arginine (poly-arginine-mediated protein transduction) and HIV-derived Tat have been identified that allow a fused protein to efficiently cross cell membranes. A distinct advantage of protein transduction is that the transduced proteins are present in the cells only transiently, a feature which depends on the intrinsic turnover of the expressed protein. In addition, intracellular concentration of the transduced protein can be controlled by varying the amount of protein added.

Identification of Pancreatic Progenitors from MAPCs

To allow identification of intermediary progenitors from MAPCs as well as insulin-1 positive cells, MAPC cell lines from transgenic mice can be engineered to express markers, such as fluorochromes, under the control of a pancreatic promoter, such as the Pdx-1, Ngn3, Pax4 and Insulin promoters and different crosses can be generated (e.g., MAPCs from the bone marrow (BM) of mice with PDX1-GFP, Ngn3-YFP, Pax4-RFP and MIP-GFP, as well as Nkx6.1-GFP and PDX-1xNgn3 mice can be isolated). Clonal populations can be isolated and tested for their pluripotency, phenotype, cytogenetics, and differentiation to β-cell like cells (evaluating expression of Pdx1, Ngn3, NeuroD1, Pax4, Nkx6.1 and insulin over time). These cell lines will allow one to follow differentiation as well as select intermediary progenitors from differentiation cultures.

EXAMPLES

The following examples are provided in order to demonstrate and further illustrate certain embodiments and aspects of the present invention and are not to be construed as limiting the scope thereof.

Example 1

In Vivo Differentiation of MAPCs to β-Cells

Murine MAPC cell lines were established from eGFP transgenic C57B1/6 Thy1.1 mice bone marrow cells as described in Jiang, Y. et al. (2002). MAPCs were cultured in 60% DMEM-LG (Gibco BRL), 40% MCDB-201 (Sigma) with 1×SITE (Sigma), 1× lenolenic acid-bovine serum albumin (LA-BSA) (Sigma), 0.1 mM ascorbic acid 2-phosphate (Sigma), 1× Chemically Defined Lipid Concentrate (Gibco), 0.05 µM Dexamethasone, 0.1 mM beta-mercaptoethanol (Sigma), 100 U penicillin (Gibco), 1000 U streptomycin (Gibco), 1000 U/mL LIF (Chemicon), 10 ng/mL mEGF (Sigma), 10 ng/mL hPDGF-BB (R&D systems), 2% fetal calf serum (FCS) (Hyclone Laboratories) on human 10 ng/cm$^2$ fibronectin (Sigma)-coated dish (Nunc) at about 5% $CO_2$ and about 5% $O_2$. Plating cell density was about 100 cells/cm$^2$ and cells were split every two days.

About 0.03-1×10$^6$ 5% $O_2$ cultured eGFP C57B1/6 low-$O_2$ MAPCs were transplanted via tail vein injection in 6-8 week old NOD-SCID mice (n=28) following irradiation at 275 cGy. Intraperitoneal injection of anti-asialo-GM1 antibody (Wako) (20 µl of the stock solution diluted in 380 µl of PBS1x) was given on day −1, +10 and +20 to decrease NK activity.

Hematopoietic reconstitution was assessed in peripheral blood (PB) at periodic intervals after infusion (5-20 weeks), after which animals were sacrificed. In all animals that were sacrificed, blood, BM, and spleen were evaluated for presence of eGFP hematopoietic cells, and small bowel, pancreas, liver, lung, skin, skeletal muscle and brain were harvested to determine contribution of MAPC-derived cells to non-hematopoietic lineages.

Figure 10A:
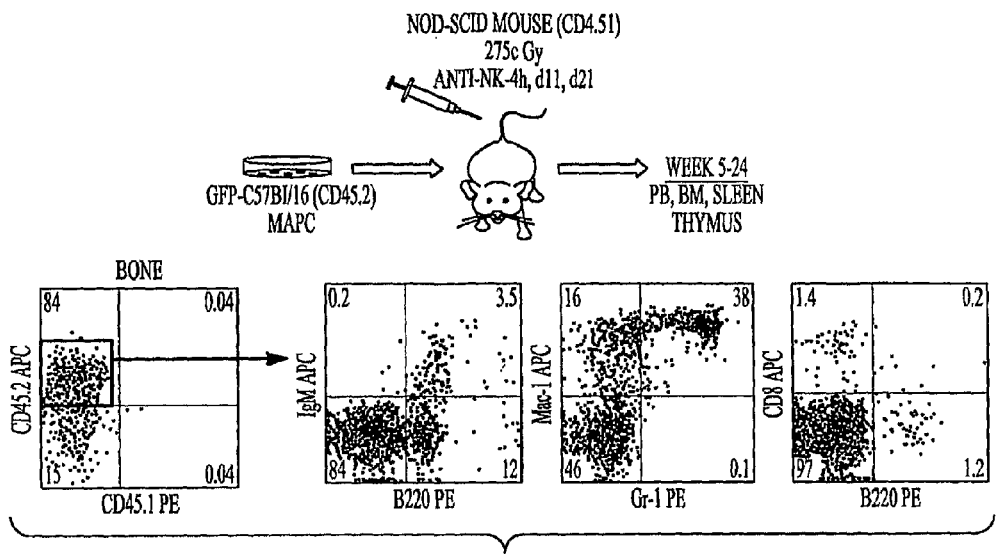
FIG. 10 depicts hematopoietic reconstitution from MAPCs. Six week-old NOD-SCID mice received 1 million Tg-GFP MAPCs IV following 275 cGy irradiation, and under cover of anti-asialo-GM1 injection (d-1, d11, 21). After 16 weeks, the animals were sacrificed. PB, BM and spleen hematopoietic cells were analyzed by FACS for presence of donor cells, and their lineage differentiation. Representative example of 1/21 engrafted mice.
Figure 10B:
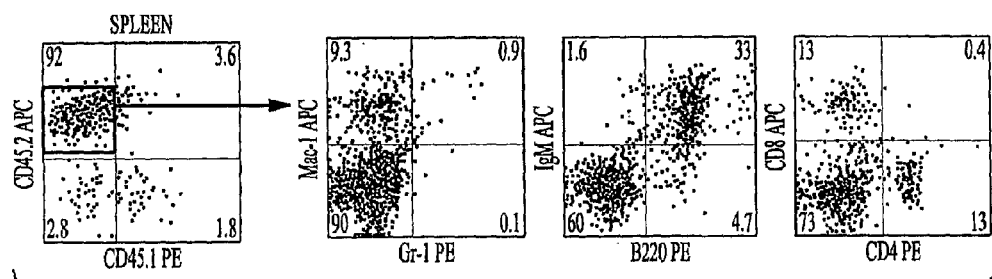
Figure 10C:
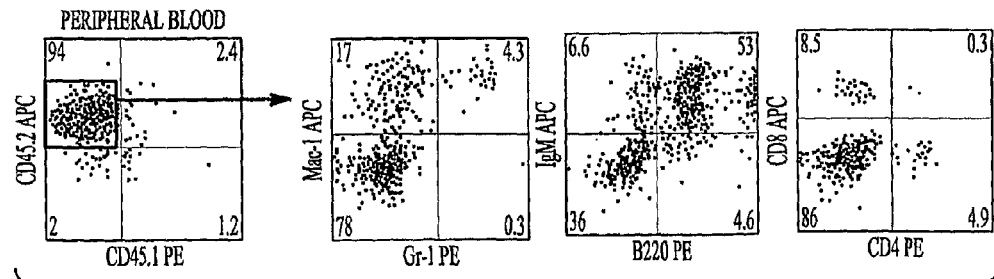

As described in FIG. 10, 21/28 animals had signs of MAPC-derived hematopoiesis. The 7 animals that did not show engraftment were transplanted with MAPCs with low levels of Oct-4 (<1% mESCs), whereas all other animals received MAPCs with Oct-4 mRNA levels between 30 and 80% of mESCs. Analysis of lymphohematopoietic tissues demonstrated multilineage engraftment (FIG. 10). FACS analysis of PB, BM, spleen, and thymus shows multilineage engraftment, including all myeloid cells, T-cells, β⁻cells and NK-cells. eGFP sorted splenic CD4/CD8 T cells were capable of reacting to Balb/C derived cells in an mixed lymphocyte reaction culture and to stimulation by anti-CD3+ anti-CD 28 mAbs (not shown). In addition ~1% of the GFP$^+$ cells expressed Sca1+cKit or Thy1+cKit, suggesting generation of hematopoietic stem cells (HSCs) from MAPC, consistent with the fact that eGFP$^+$ CFU-Mix and BFU-E could be cultured and the ability of BM from the primary recipients to reconstitute the hematopoietic system of lethally irradiated secondary recipients.

Other organs, such as lung, pancreas, heart, liver and small bowel, were also analyzed for the presence of MAPC-derived progeny. High-level contribution was seen in the gut, with differentiation into cells with morphological and phenotypical characteristics of gut epithelium. Interestingly, engraftment is seen in all but the lower 3-4 cells in the crypt, consistent with engraftment in the gut stem cell compartment. This was seen in 2/12 animals, both of which had become very ill at about w5-6, but improved by administration of an antibiotic. These two animals were sacrificed on w13. In the other 10 animals, no engraftment in the gut epithelium was seen. For other organs, low-level engraftment, mainly in the mesenchymal compartment was seen. In the heart, 200-300 GFP$^+$ cardiac Troponin$^+$ cells were detected.

Immunofluorescence for insulin and GFP and immunohistochemistry for GFP on pancreas after transplantation of MAPCs was carried out. First, immunohistochemistry for GFP on pancreas was carried out as follows. Pancreata were fixed for 24 hours at 4° C. in 10% neutral buffered formalin in PBS. After two washes with PBS, samples were paraffin-embedded. 6 micron sections were cut and placed on Super-Frost Plus slides. After standard dewaxing and rehydration, sections were washed three times for 5 minutes each with distilled water. Antigen retrieval was done by steaming for 20 minutes in 0.01 M citrate buffer pH 6.0 (Invitrogen) in a house-hold rice cooker, followed by a 20 minute cool-down period. After a quick rinse in distilled water, sections were permeabilized for 5 minutes with PBS+0.05% Tween-20. Endogenous peroxidase was blocked by sequential 5 minute incubations with 1.8% $H_2O_2$ in distilled water and 2.5% periodic acid (Sigma) in water, separated by a 5 minute wash with running tap water. After a 5 minute wash with running tap water, slides were incubated for 2 minutes with 0.02% sodium borohydride (Sigma) in distilled water. After a 5-minute wash with running tap water, endogenous biotin was blocked by sequential 15 minute incubations with avidin and biotin (Biotin Blocking System, DakoCytomation), separated by a 5 minute wash in PBS+0.05% Tween-20. After incubation with biotin, sections were washed for 5 minutes with PBS+0.05% Tween-20. Non-specific binding sites were blocked by incubation for 30 minutes with 0.4% fish skin gelatin in PBS. Blocking buffer was removed and primary antibody, diluted in PBS+0.05% Tween-20+1% BSA was added to the sections and incubated overnight at 4° C. Rabbit anti-GFP was from Abcam (ab6556) and used at 0.67 µg/ml. The following morning, slides were washed three times for 5 minutes each with PBS+0.05% Tween-20. Biotinylated anti-rabbit F(ab')$_2$ antibody, diluted 1:1500 in PBS+0.05% Tween-20 was added to the sections and incubated for 30 minutes. Slides were washed three times for 5 minutes each with PBS+0.05% Tween-20. The Vectastain ABC peroxidase complex (Vector Laboratories), prepared according to manufacturer's instructions, was added to the sections and incubated for 30 minutes. Slides were washed three times for 5 minutes each with PBS+0.05% Tween-20. Color was developed using DAB+ (DakoCytomation), according to manufacturer's instructions. After standard hematoxylin counterstaining, dehydration and mounting, pictures were taken using a Nikon Coolpix 4500 digital camera, mounted on a Zeiss Axioskop 2.

GFP$^+$ islets were observed in two animals in a single staining experiment.

Next, immunofluorescence for insulin and GFP on pancreas after transplantation of MAPCs was carried out as follows. Pancreata were fixed for 24 hours at 4° C. in 10% neutral buffered formalin in PBS. After two washes with PBS, samples were paraffin-embedded. 6 micron sections were cut and placed on SuperFrost Plus slides. After standard dewaxing and rehydration, sections were washed three times for 5 minutes each with distilled water. Antigen retrieval was done by steaming for 20 minutes in 0.01 M citrate buffer pH 6.0 (Invitrogen) in a house-hold rice cooker, followed by a 20 minute cool-down period. After a quick rinse in distilled water, sections were permeabilized for 5 minutes with PBS+ 0.05% Tween-20. Non-specific binding sites were blocked by incubation for 30 minutes with 0.4% fish skin gelatin in PBS. Blocking buffer was removed and primary antibody, diluted in PBS+0.05% Tween-20+1% BSA was added to the sections and incubated overnight at 4° C. Guinea pig anti-insulin was from DakoCytomation (A0564) and used at 21.25 µg/ml. Rabbit anti-GFP was from Abcam (ab6556) and used at 21 g/ml. The following morning, slides were washed three times for 5 minutes each with PBS+0.05% Tween-20. Sections were incubated for 30 minutes with Cyanine-2 labeled anti-guinea pig and cyanine-3 labeled anti-rabbit F(ab')$_2$ antibodies (Jackson Immunoresearch), diluted respectively 1:125 and 1:450 in PBS containing TO-PRO-3-iodide (Invitrogen) at 1:1000. After three washes for 5 minutes each in PBS+ 0.05% Tween-20, slides were mounted using ProLong Gold (Invitrogen). Confocal laser scanning pictures were taken on BioRad Radiance 2100, mounted on a Zeiss Axioskop 2.

Figure 11:
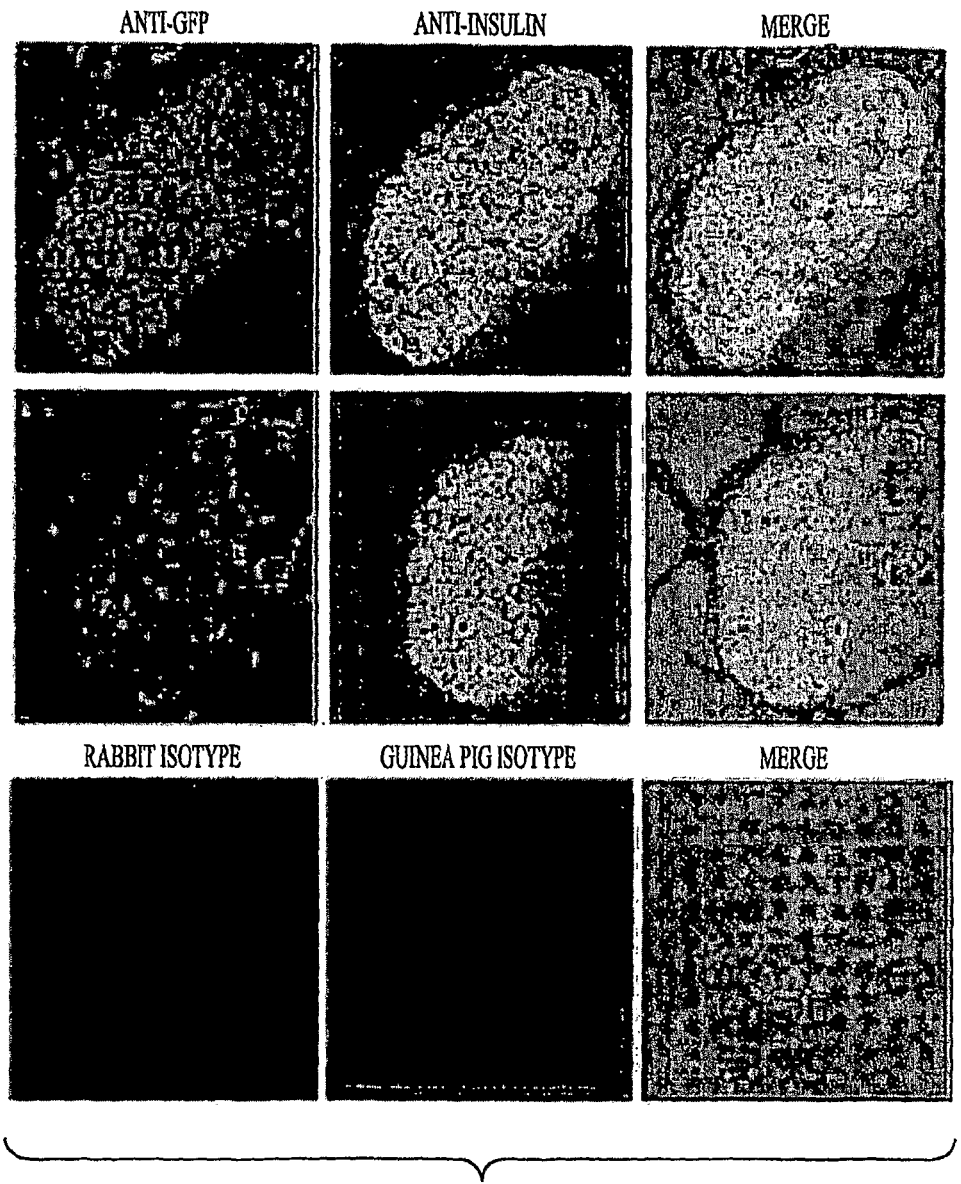
FIG. 11 depicts GFP$^+$ Insulin$^+$ donor islets in GFP MAPC grafted NOD-SCID mice. A 6 week-old NOD-SCID mouse received 1 million Tg-GFP MAPCs IV following 275 cGy irradiation, and under cover of anti-asialo-GM1 injection (d-1, d11, 21). After 12 weeks, the animal was sacrificed. 70% of the PB, BM and spleen hematopoietic cells were GFP$^+$. 7% GFP$^-$ T cells were also present. The pancreas of the animal was analyzed by anti-GFP-Abs combined with anti-insulin Abs. Shown is a GFP$^+$ islet and a GFP$^-$ islet from the same pancreas. (Example of 1 of 2 identical animals.)

In at least two NOD-SCID mice in which undifferentiated GFP$^+$ MAPCs were grafted, GFP$^+$/insulin$^+$ islets were detected in the pancreas (FIG. 11).

Example 2

In Vitro Differentiation of Rodent MAPCs to

β-Cell Progenitors and β-Cells

Commitment of MAPCs Towards an Endocrine Pancreas Lineage

Using low-$O_2$, high Oct-4 (FIG. 2; in one embodiment, high Oct-4 is about 5 to about 25% of that found in rat embryonic stem cell or universal mRNA, while low Oct-4 is generally about 4 orders of magnitude less) expressing mouse MAPCs and rat MAPCs (isolated and cultured as described herein), it was determined that transcription factors known to play a role in endoderm→pancreas→endocrine pancreas→β-cell commitment and differentiation can be activated in the correct sequence yielding a final cell population that expresses insulin-1 mRNA. For example, MAPCs were induced to express the transcriptional program of β-cells, with sequential expression of the transcription factors (TFs) Hnf3β, Hnf6, Pdx-1, Ngn3, NeuroD1, Pax4, Nkx61, as wells as insulin-1, insulin-2, glucagon and somatostatin mRNA when cultured with Activin-A and BMP4 d0-9, anti-SHH d3-d9, EGF d9-15; nicotinamide (or exendin 4), β-cellulin and GDF11 dl 5-21.

The expansion and differentiation media (supplemented with factors described herein below) for the rodent MAPCs are described in Table 2.

TABLE 2

| Components | Expansion media | Differentiation media |
| --- | --- | --- |
| DMEM-LG (Gibco) | 300 mL | 300 mL |
| MCDB (Sigma) | 200 mL (40%) | 200 mL (40%) |
| FCS (Hyclone) | 10 mL (2%) | 10 mL (2%) |
| ITS + 1 (Sigma) | 5 mL | 5 mL |
| L-Ascorbic Acid (Sigma) | 5 mL (0.1 mM) | 5 mL (0.1 mM) |
| Pen/Strep (Gibco) | 5 mL | 5 mL |
| Dexamethasone (Sigma) | 100 µL (0.05 µM) | |
| β-Mercaptoethanol (Gibco) | 500 µL (0.1 mM) | 500 µL (0.1 mM) |
| hPDGF (R&D) | 500 µL (10 ng/mL) | |
| hEGF (Sigma) | 500 µL (10 ng/mL) | |
| mLIF (Chemicon) | 50 µL (1000 U/mL) | |

Additionally, culture dishes/flasks were coated at room temperature for one hour with 10 ng/mL of fibronectin (FN).

Cytokine Mediated Differentiation

Cytokine mediated differentiation was achieved after a multifactorial analysis of the effect of different cytokines and extracellular matrix (ECM) components known to play a role in endoderm, foregut, pancreas and endocrine pancreas specification and differentiation. Using Q-RT-PCR, it was determined that undifferentiated rat MAPCs do not express significant levels of transcripts for Pdx-1, Ngn3, NeuroD1, Nkx6.1, Ins-1 and Ins-2 (less than 35 cycles), low levels of transcripts for Hnf1, Hnf3β(between 30 and 35 cycles), and detectable levels of transcripts for Nkx2.2 and Glut2 (<30 cycles).

For Q-RT-PCR reactions described herein, the primer sequences are presented in Tables 3-5 and the following protocols were used: RNA was extracted from the cells with the aid of the RNeasy Mini Kit (Qiagen; Valencia Calif.), followed by a DNase Treatment with DNA-Free™ (Ambion, Austin, Tex.). The RNA was reverse transcribed with TaqMan (Applied Biosystems, Foster City, Calif.; Step 1 (Incubation): 25° C., 10 min; Step 2 (RT): 48° C., 30 min; Step 3 (RT Inactivation): 95° C., 10 min). A reaction mixture is presented in Table 6.

TABLE 3

| Target | Set | Sequence | SEQ ID NO: | Accession | Description |
|---|---|---|---|---|---|
| hACVR1B v1 | F1 | TTACCCCACACACAGTCCAA | 1 | | |
| | R1 | CCAAAAACACGGCTTCAGTT | 2 | NM_004302 | activin A receptor, type IB variant 1 |
| hACVR1B v2 | F1 | TAGGGTGCCATTTGGAGTTC | 3 | | |
| | R1 | ACATTGCCCAGGTTTGTCTC | 4 | NM_020327 | activin A receptor, type IB variant 2 |
| hACVR1B v3 | F1 | CCTACCTCCCATTCCAGGAT | 5 | | |
| | R1 | GCACCCTAAGCACAGCTACC | 6 | NM_020328 | activin A receptor, type IB variant 3 |
| hADAM9 | F1 | CCACTTGAGAATTTCATGAGCA | 7 | | |
| | R1 | TTTACATGACCCAGCACACC | 8 | NM_003816.1 | a disintegrin and metalloproteinase domain 9 |
| hALCAM | F1 | AGGTGGCAGCTTGTGAAGAT | 9 | | |
| | R1 | GAGTCGGCTCCTATGGTGTC | 10 | NM_001627 | activated leucocyte cell adhesion molecule |
| hCD44 | F1 | AGCCCATTGTTCATTCTTGTG | 11 | | |
| | R1 | AGAGGAAGGGTGTGCTCTGA | 12 | NM_000610 | homing function and Indian blood group system |
| hCD164 | F1 | TGAGCCATTAATTTTTGGGTTT | 13 | | |
| | R1 | AGCAGTATCTGCCTGTGCAA | 14 | NM_006016 | sialomucin |
| hDDR1 | F1 | AATGTTTCCTTGTGCCTGCT | 15 | | |
| | R1 | CCAGGTCCAGTGTTTCAGGT | 16 | NM_001954.3 NM_013993.1 NM_013994.1 | (discoidin domain receptor family, member 1 |
| hGPNMB | F1 | CAGGCATGATGCTGAGTGAC | 17 | | |
| | R1 | CAGGGACCTCATCTTTGGAA | 18 | NM_002510.1 | glycoprotein transmembrane nmb |
| hIL6ST | F1 | TCACAATCCTGTGGATCTGG | 19 | | |
| | R1 | CCCTCAGTACCTGGACCAAA | 20 | NM_002184 NM_175767 | interlukin 6 signal transducer |
| hITGA5 | F1 | CCAAGGGGAATCAGAACTCA | 21 | | |
| | R1 | TGGAGCAGGCCCAAATATAG | 22 | NM_002205 | integrin Alpha V |
| hITGB1 | F1 | TGCAACAGCTCTCACCTACG | 23 | | |
| | R1 | AAGATGGGCAACTCAAATGG | 24 | NM_002211 | integrin, beta 1 variant 1a |
| hITGB5 | F1 | ACTGAGATGCTGGGCTGTCT | 25 | | |
| | R1 | GACCCTTCCTGACAGTCGTC | 26 | NM_002213.3 | Integrin, beta 5 |
| HNIFIE14 | F1 | GAGACCTTCGTCCACCTCTG | 27 | | |
| | R1 | CATTGACAACGGCGACATAC | 28 | NM_032635.2 | seven transmembrane domain protein |
| hTM4SF1 | F1 | CCCTTTGAACTGCCTTGTGT | 29 | | |
| | R1 | TGCATTCATTTGGATTGGAA | 30 | NM_014220.1 | transmembrane 4 superfamily member 1 |

TABLE 4

Mouse Primers

| Target | Sequence | SEQ ID NO: | Product size | Accession |
|---|---|---|---|---|
| mAbcg2 | TCACTGACCCTTCCATCCTC | 31 | | |
| | GGAATACCGAGGCTGATGAA | 32 | F1R1 = 143 bp | NM_011920 |
| mCD24a | TGGAAGAAGGAGAGCTCACAG | 33 | | |
| | CATTCAGGTGTGAGGCAAGG | 34 | F1R1 = 75 bp | NM_009846 |
| Mmsi-1 | GATGCCTTCATGCTGGGTAT | 35 | | |
| | TAGGTGTAACCAGGGGCAAG | 36 | F1R1 = 101 bp | NM_008629 |

TABLE 4-continued

Mouse Primers

| Target | Sequence | SEQ ID NO: | Product size | Accession |
|---|---|---|---|---|
| mOct-4 | CCAATCAGCTTGGGCTAGAG | 37 | | |
| | CCTGGGAAAGGTGTCCTGTA | 38 | F1R1 = 129 bp | NM_013633 |
| | CAAGGCAAGGGAGGTAGACA | 39 | | |
| | GCTCCTGATCAACAGCATCA | 40 | F1R1 = 132 bp | NM_013633 |
| MSox1 | CACAACTCGGAGATCAGCAA | 41 | | |
| | TGTAATCCGGGTGTTCCTTC | 42 | F1R1 = 127 bp | NM_009233 |
| mSSEA1 | TATTCCAGGAGCGATCCAAC | 43 | | |
| | CTCGTTCCAGTTGCTCACAA | 44 | F1R1 = 99 bp | NM_010242 |

TABLE 5

| Target | Sequence | SEQ ID NO: | Size | Accession |
|---|---|---|---|---|
| AMY1 | AGGAACATGGTTGCCTTCAG | 45 | | |
| | AGTGCTTGACAAAGCCCAGT | 46 | 144 | NM_031502 |
| HNF3b (FoxA2) | GGAAACATTGGGGGAACTTT | 47 | | |
| | GTGTGGCCCAGCTATTTAGG | 48 | 99 | NM_012743 |
| GAPDH | TGCCACTCAGAAGACTGTGG | 49 | | |
| | GGATGCAGGGATGATGTTCT | 50 | 85 | NM_017008 |
| GCG | TTTTGTGCAGTGGTTGATGA | 51 | | |
| | CAGCATGCCTCTCAAATTCA | 52 | 80 | NM_12707 |
| GcK | GTGGAGCCCAGTTGTTGACT | 53 | 84 | |
| | GGCTCATCACCTTCTTCAGG | 54 | | NM_012565.1 |
| HNF1b | ACCCTCACCAGCATGTCTTC | 55 | | |
| | GTCAGGTCGCTGGACTTCTC | 56 | 150 | NM_013103 |
| HNF4a | CCTGATGCAAGAACACATGG | 57 | | |
| | TGATGGCTGTGGAGTCTCAG | 58 | 133 | NM_022180 |
| HNF6 | CTGTGAAACTCCCCCAGGTA | 59 | | |
| | TCATCCCGCATAAGTGTGAA | 60 | 195 | NM_022671 |
| INS1 | CACCTTTGTGGTCCTCACCT | 61 | | |
| | GACGGGACTTGGGTGTGTAG | 62 | 82 | NM_019129 |
| INS2 | GAAGTGGAGGACCCACAAGT | 63 | | |
| | CAGTGCCAAGGTCTGAAGGT | 64 | 78 | NM_019130 |
| Isl1 | GGGACGGGAAAACCTACTGT | 65 | 95 | |
| | CACGAAGTCGTTCTTGCTGA | 66 | | NM_017339.1 |
| NeuroD | CCCAAAGCAAACAACCACTT | 67 | | |
| | GTACCCCATCCTCCTGGAAT | 68 | 142 | NM_019218.1; NM_002500 (human) |
| NGN3 | GAGTGGGTGGGCGTACTCTA | 69 | | |
| | TTGGAACTGAGCACTTCGTG | 70 | 186 | NM_021700.1; BC074939 (human) |
| Nkx6-1 | ACTTGGCAGGACCAGAGAGA | 71 | | |
| | GGAACCAGACCTTGACCTGA | 72 | 75 | NM_006168 (human) |
| P48 | AGGCCCAGAAGGTCATCATC | 73 | 78 | |
| | GAGGAGGGAGACCGTAGTCC | 74 | | NM_178161 (human) |
| PAX4 | AGGACAAGGCTCCCAGTGTA | 75 | 117 | |
| | TAGGAAGAGCTGGAGCCAAA | 76 | | NM_031799.1; BC074761 (human) |
| PAX6 | TCCCAGGGATCTGAGAATTG | 77 | | |
| | CACAACGGTTTGAAATGACG | 78 | 104 | NM_13001; NM_001604 (an example of a human Pax6 sequence) |

TABLE 5-continued

| Target | Sequence | SEQ ID NO: | Size | Accession |
|---|---|---|---|---|
| PDX1 | TCTGCCTCTGGGACTCTTTC | 79 | | |
| | GGGACCGCTCAAGTTTGTAA | 80 | 89 | NM_022852; U35632 (human) |
| PPY | CCACCCAAGTGGATAGGAGA | 81 | | |
| | CAGCAGAAGGTAGGTGTCTGG | 82 | 102 | NM_012626.1 |
| SST | CCCAGACTCCGTCAGTTTCT | 83 | | |
| | GTTGGGCTCAGACAGCAGTT | 84 | 99 | NM_12659.1 |
| SYP | TGATCGTGTGTTGCCATTTT | 85 | | |
| | AACAATACCGAAGGGCACAG | 86 | 85 | NM_012664 |
| Glut2 | ATCCACATTCGGAACAGGAC | 87 | 80 | |
| | CAAGGTTCCGGTGATCTTGT | 88 | | NM_012879.1 |
| Flk1 | CCAAGCTCAGCACACAAAAA | 89 | | |
| | CCAACCACTCTGGGAACTGT | 90 | | |
| VWF | CCCACCGGATGGCTAGGTATT | 91 | | |
| | GAGGCGGATCTGTTTGAGGTT | 92 | | |
| VE-Cadherin | GGCCAACGAATTGGATTCTA | 93 | | |
| | GTTTACTGGCACCACGTCCT | 94 | | |

TABLE 6

| Component | 100 μL Reaction | Final conc. |
|---|---|---|
| 10x Taqman RT Buffer | 10.0 μL | 1X |
| 25 mM Magnesium Chloride | 22.0 μL | 5.5 mM |
| DeoxyNTPx Mixture | 20.0 μL | 500 μM/dNTP |
| Random Hexamers | 5.0 μL | 2.5 μM |
| RNase Inhibitor | 2.0 μL | 0.4 U/μL |
| MultiScribe Reverse Transcriptase (50 U/μL) | 2.5 μL | 1.25 U/μL |
| RNA (1 μg/100 μL reaction) | X | |
| RNase-free water | 38.5 μL – X | |
| TOTAL Volume | 100 μL | |

Following reverse transcription, Quantitative Real Time PCR (Q-RT-PCR) was performed as follows: Step 1: 50° C., 2 min (Incubation); Step 2: 95° C., 10 min (Taq activation); Step 3: 95° C., 15 sec (Denaturation) followed by 60° C., 1 min (Extension) and repeat for 40 cycles; Step 4: 95° C., 15 sec (Dissociation); Step 5: 60° C., 20 sec (Melting curve); Step 6: 95° C., 15 sec. Table 7 provides a reaction mixture for Q-RT-PCR.

TABLE 7

| Component | 12 μL Reaction | Final conc. |
|---|---|---|
| Syber Green (2x) | 6.0 μL | 1X |
| Reverse Primer (5 μM) | 0.25 μL | 200 nM |
| Forward Primer (5 μM) | 0.25 μL | 200 nM |
| cDNA (10 ng/μL) | 3.0 μL | (30 ng/reaction) |
| RNase-free water | 2.5 μL | |
| TOTAL Volume | 12 μL | |

In an initial series of studies, the effect of cell density (about $10^4$-$10^5$ cells/cm$^2$), ECM component (fibronectin, collagen, matrigel) and different concentrations (10-100 ng/mL) of bFGF (10-100 ng/mL), FGF2 (10-100 ng/mL), Activin A (e.g., about 10 ng/mL to about 100 ng/mL), BMP4 (e.g., about 10 ng/mL to about 50 ng/mL), retinoic acid (about $10^{-6}$M), EGF (e.g., about 10 to about 100 ng/mL), FGF10 (e.g., about 50 to about 150 ng/mL, including about 100 ng/mL), HGF (e.g., about 10 to about 100 ng/mL), GDF11 (e.g., about 50 to abut 150 ng/mL), cyclopamine (e.g., about 10 μM), anti-SHH antibody (Ab; e.g., about 10 μg/mL), nicotinamide (e.g., 5 μM to about 50 μM, including about 10 μM), exendin 4 (about 5 nM to about 50 nM, including about 10 nM), betacellulin (e.g., about 50 to abut 150 ng/mL) alone or in combinations of 2 or 3 and in different temporal sequences, on the induction of transcription factors, insulin, glucagon and somatostatin expression levels after 6, 12 and 18 days using Q-RT-PCR was determined.

A combination of activin-A, BMP4 and cyclopamine or anti-SHH Ab induced the highest (>100 fold) increase in Pdx-1 mRNA. The highest increase in Pdx-1 mRNA was seen when cells were plated on matrigel at about 50,000 cells/cm$^2$. However, when cells were maintained for >6 days, MAPC-derived cells appeared to die.

Figure 3A:
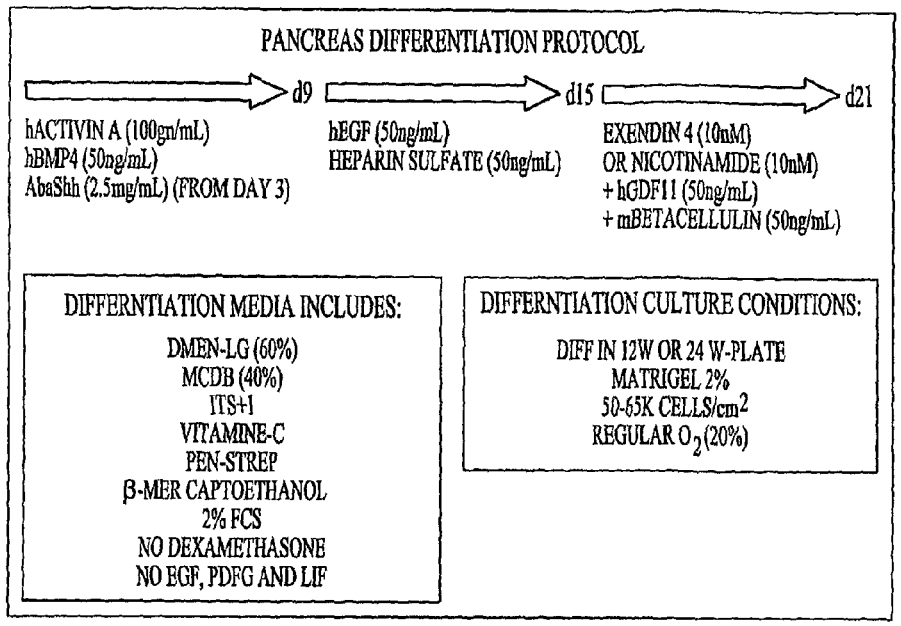
FIG. 3A depicts a pancreas differentiation protocol. 3B and 3C depict various factors for use in differentiation of MAPCs towards a pancreatic fate and various transcription factors that can be expressed during the differentiation process.
Figure 3B:
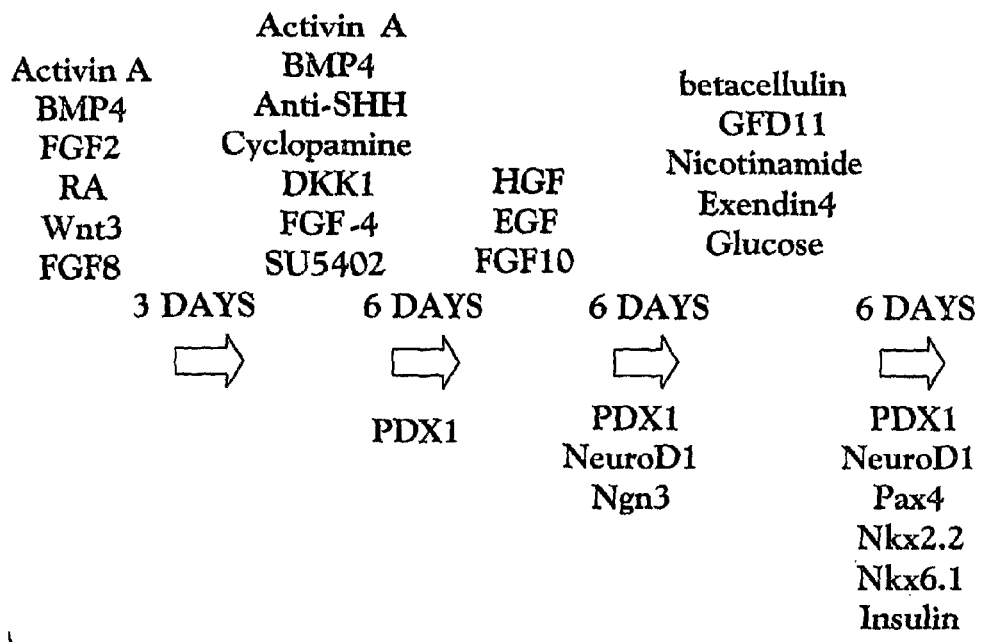
Figure 3C:
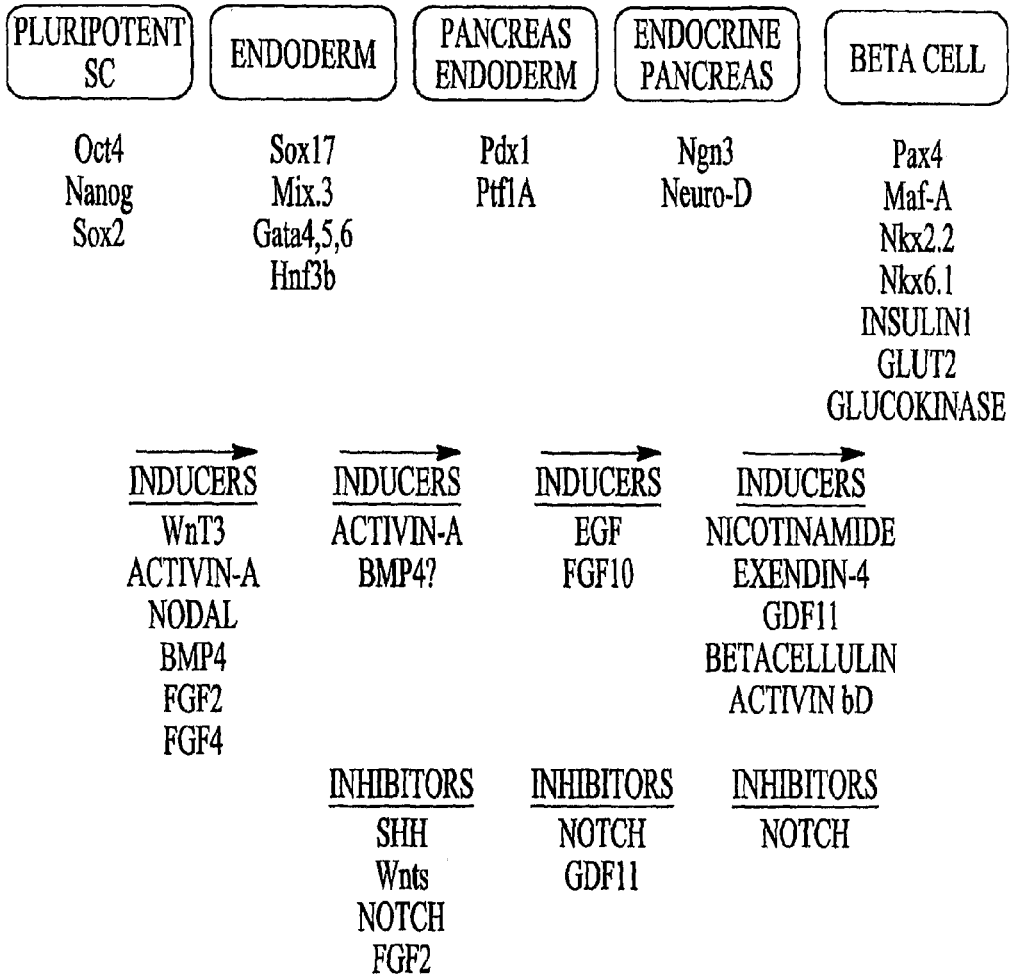

Subsequent addition of factors believed to play a role in further proliferation and differentiation from pancreas-committed cells to mature endocrine pancreas, including EGF (e.g., about 50 ng/mL), HGF (e.g., about 50 ng/mL) and FGF10 (e.g., about 100 ng/mL), either alone or in combination was tested. These studies demonstrated that cell survival was significantly better when activin-A, BMP4 and cyclopamine or anti-SHH Ab were withdrawn after d6 and cells maintained in the presence of EGF or HGF, but not FGF10. Combining EGF, HGF and/or FGF10 did not have an additive effect. However, when cultures were maintained with EGF, cells again appeared to die beyond day 12. Addition of 10 μM nicotinamide (Sigma, St. Louis, Mo.) and 10 nM Exendin4 (Sigma, St. Louis, Mo.) following day 12 supported better survival of cells and further differentiation to endocrine pancreas as levels of insulin-1 mRNA increased by an additional 2-4 fold by d18. When GDF11 was added, a further increase in Ins1 and Ins2 mRNA levels was seen. Further optimization was obtained by adjusting the duration of the different steps along the differentiation course, as well addition of β-cellulin (50 ng/mL). Differentiation in 20% $O_2$ with Exendin4 (or nicotinamide), GDF11 and betacellulin yielded Insulin 1 mRNA at levels between 1 and 3% of pancreas. The schema for differentiating MAPCs to pancreatic cells is depicted in FIG. 3.

Figure 4:
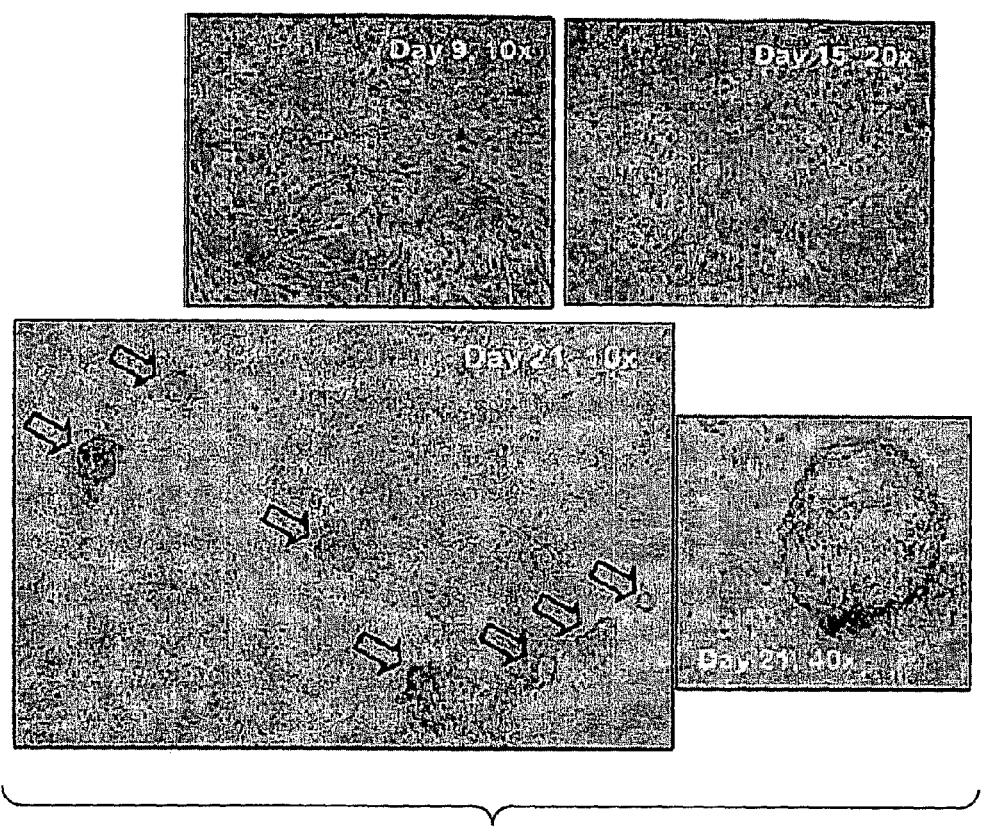
FIG. 4 depicts the morphological appearance of MAPC-beta-cell differentiation cultures. By day 15 large patches of epithelioid cells can be seen in the adherent layer, surrounded by "stromal" looking cells. By day 18 these patches start forming three dimensional very well delineated clusters which eventually bud off in the culture supernatant (day 21).
Figure 5A:
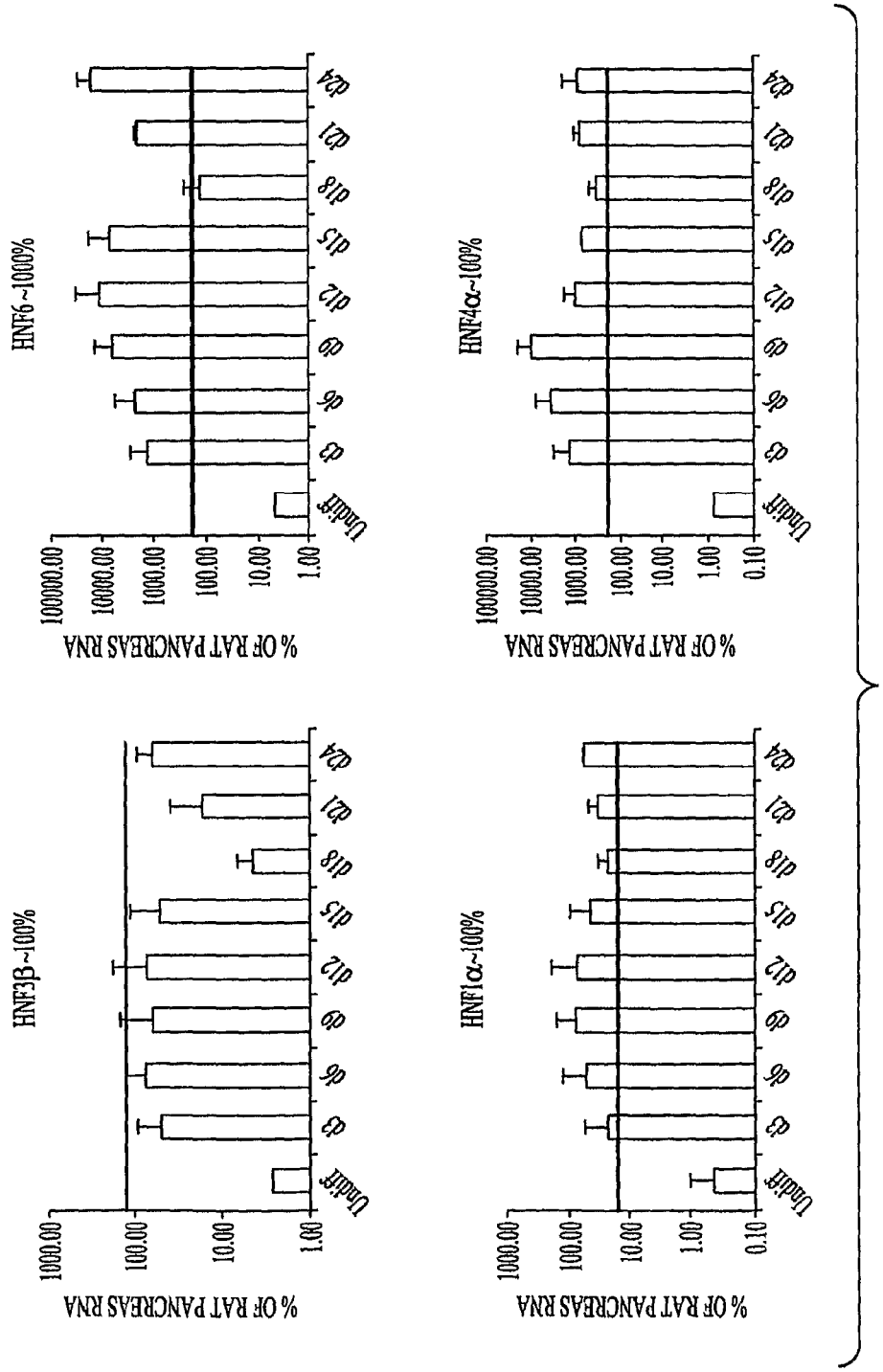
FIG. 5 depicts the results of Q-RT-PCR evaluation of rat MAPCs differentiated for 21 days towards endocrine pancreas. Rat MAPCs were plated on matrigel using the sequential protocol described in FIG. 3A. Every 3 days, cultures were harvested (data for dl 8, 21 and 24 represent data on non-attached clusters only), RNA extracted, and levels of transcription factors and hormones were measured by Q-RT-PCR compared with GAPDH as control, and compared with levels detected in primary rat pancreas, except for Ngn-3, Nkx2.2 and Neuro-D1, where levels were compared with fetal rat RNA. Results shown are mean+/−SEM for 3 experiments.
Figure 5B:
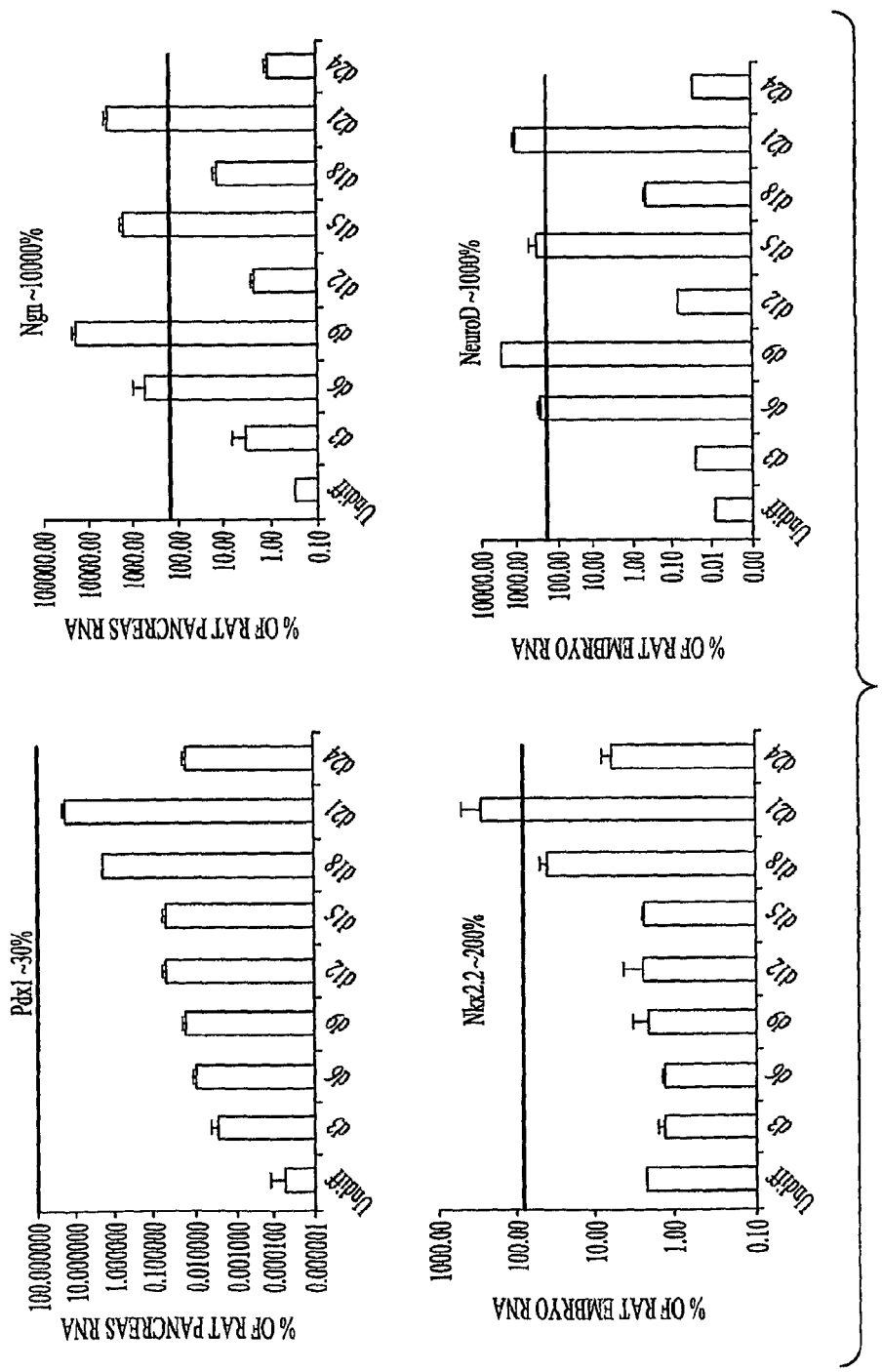
Figure 5C:
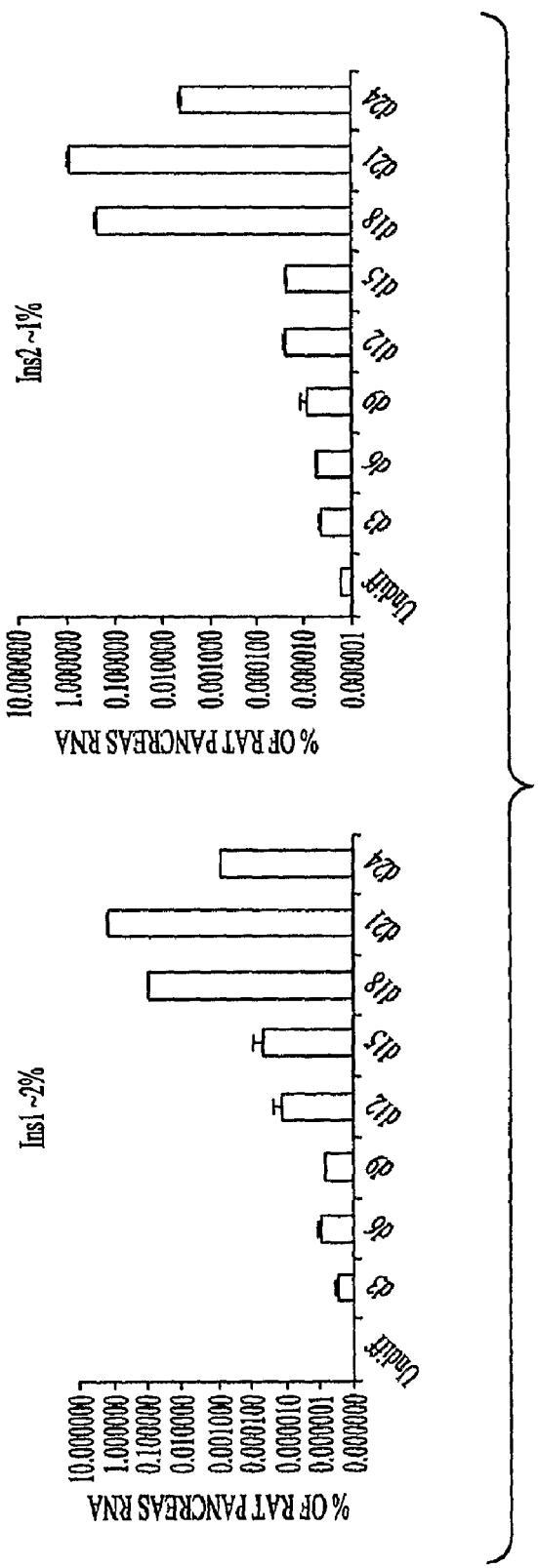

With this differentiation schema, differentiation was extended beyond dl 5-18. By day 18, clusters of cells budded off the cells attached to the bottom of the plate (FIG. 4). Expression of transcription factors and hormone mRNAs in the cultures and from dl 8 in the clusters above the "stromal feeder" are summarized in FIG. 5.

These studies demonstrate that there is a consistent early increase in expression of the Hnf3α, Hnf6, and Hnf1α mRNA from d3 on. Pdx-1 mRNA starts to increase from d3 and expression increased further till day 21. Ngn3 transcripts were detected on d3, but increased further by >10,000 fold by day 12-18. Its downstream target Neuro-D significantly increased from d6. Significant increases in Nkx2.2, Insulin-1 and -2 mRNA were seen from d15. Clusters harvested from the supernatant of the cultures on day 18 and 21 express levels of Insulin-1 mRNA of ~1% of total rat pancreas, Insulin-2 mRNA of ~1% of total rat pancreas, glucagon mRNA (not shown) of ~0.5% of total rat pancreas. High levels of Ngn-3 and Neuro-D mRNA were still detected, this suggests that the cells within the clusters are at different stages of differentiation. Unexpectedly, levels of some transcription factors (Ngn3 and Neuro-D and to a lesser extent HNF3β and HNF6) appeared to drop on day 12 and/or d18, after which levels increased again. This may be a reflection of how the culture is fed: half media changes are done d3, 6, 12, 18 and 21, whereas 100% of the medium is replaced on d9 and d15 at which time the cytokine mix is changed as well. It is therefore possible that due to the full media change, cytokines secreted in the culture system itself, or the abrupt changeover of cytokines may play a role.

On day 18, 21 and 24, the attached "stromal" layer of cells were examined for endodermal and mesodermal characteristics. Significantly levels not different from what is detectable in the clusters above the feeder, of Hnf's were detected. However, levels of Pdx1, Ngn3, Neuro-D, Ins1 and Ins2 mRNA in the adherent layer were 1,000-10,000 fold lower than those measured in the non-attached clusters. In addition, there were readily detectable transcripts for a number of endothelial genes (Flk1, Flt1, VE-Cadlierin and vWF) and smooth muscle (SM22 and αSMA) in the stromal layer. Presence of endothelium may be beneficial, as there is a significant body of evidence that development of pancreas (and liver) depends on presence of endothelium (Matsumoto et al., 2001; Lammert et al., 2001).

Aside from endocrine pancreas transcripts, low levels of exocrine pancreas transcripts, including amylase, were also detected. These levels were $10^7$-$10^8$ fold lower than those in fresh pancreatic tissue (data not shown). Moreover, other endodermal genes, specifically hepatocyte associated genes including AFP and albumin, were also expressed in cultures aimed at pancreas differentiation, indicating that the differentiation conditions are not 100% specific for pancreas.

Figure 6:
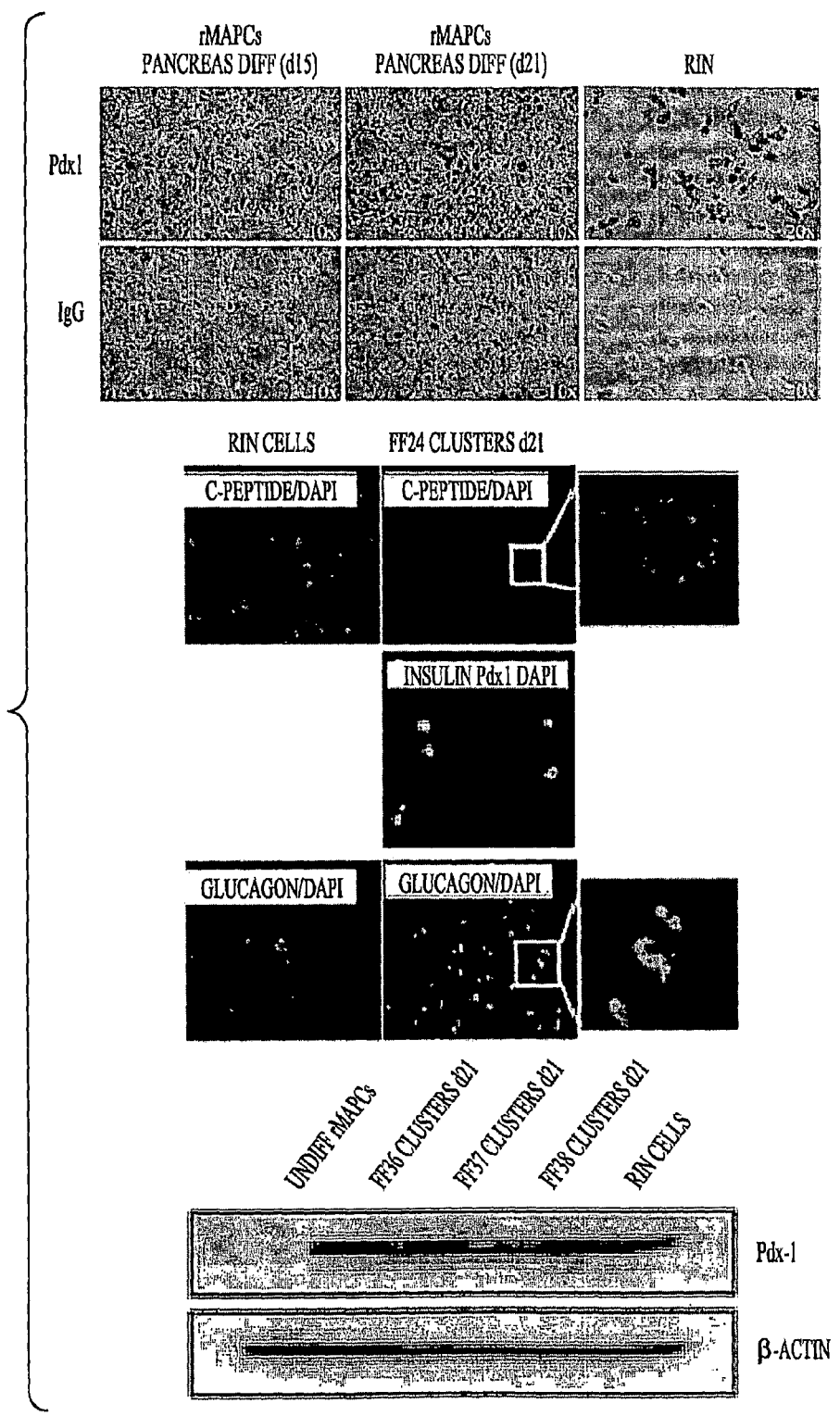
FIG. 6 depicts immunohistology of clusters. Top panels: Clusters were harvested on d15 and d21, dissociated with trypsin and stained with anti-Pdx-1, c-peptide and glucagon antibodies. Bottom panel: Clusters were harvested on d21, and western blot performed with Abs against Pdx-1 and β-actin. In both panels, RIN cells serve as control.

The expression of endocrine pancreas markers at the protein level were evaluated. Immunohistological examination of the cultured rat MAPCs at ~21 days after culture under pancreas differentiation conditions (Activin-A and BMP4 d0-9, anti-SHH d3-d9, EGF d9-15; nicotinamide, β~-cellulin, exendin4 and/or GDF11 d15-25) was performed. Staining was performed on the clusters of cells that bud off the stromal feeder for glucagon, c-peptide and Pdx-1. As shown in FIG. 6, between 10 and 20% of the cells stain positive for Pdx-1, in a typical nuclear pattern; between 1 and 2% of cells in the clusters stain positive for c-peptide, in a typical granular pattern, all of which are also Pdx-1 positive; between 5 and 10% of the cells stain positive for glucagon, only found in the cytoplasm; and as a comparison, rat insulinoma (RIN) cells stained for insulin and glucagon.

The effect of performing differentiations at 5% $O_2$ or at 20% $O_2$ was also tested. It was determined that differentiation in 20% $O_2$ yielded higher Ins1 levels.

Transcription Factor Transduction and Optionally Cytokine Mediated Differentiation Recent publications have demonstrated that exogenous expression of the pancreatic lineage transcription factor PDX-1 in ES cells (Miyazaki et al, 2004) or adult tissues (intestinal epithelioid cells; Yoshida et al., 2002) or exogenous expression of the secondary transcription factor neurogenin-3 in ES cells (Dominguez-Bendala et al., 2005) or adult tissues (pancreatic duct cells; Heremans et al., 2002) can up-regulate insulin in these cells.

Studies in which rat MAPCs induced down an endodermal pancreas pathway were transduced with adenoviral vectors expressing murine Pdx-1 and murine Ngn3 cDNA were conducted. The vectors contained the coding sequences of hemagglutinin-tagged mouse Neurogenin-3 (Ad-Ngn3) or mouse Pancreatic-and-Duodenal homeobox-1 (Ad-Pdx1) or enhanced Green Fluorescent Protein (Ad-GFP), all constitutively expressed under control of the CytoMegaloVirus (CMV) promoter (Heremans, Y., et al. 2002). In addition, the adenovirus encoding Ngn3 also contained the eGFP cDNA downstream of a separate CMV promoter (Ad-Ngn3-GFP). Recombinant, replication-deficient adenoviruses were amplified following the standard protocol as described by He T-C. et al. 1998.

Transductions were done on day0, d6 after initial treatment with activin, BMP4 and anti-SHH Ab or d12 after initial treatment with activin, BMP4 and anti-SHH Ab followed by EGF for 6 days). Adenoviral infection of cultured cells was carried in 12-well multi-well plates. The cells were washed twice with Phosphate-Buffered Saline (PBS) (Cellgro). 1 well of cultured cells was trypsinized and used to determine the cell number. For single-infection experiments, i.e., Ad-GFP, Ad-Pdx1 or Ad-Ngn3-GFP, viruses were diluted to a Multiplicity of Infection (MOI) of 2500 (2500 infectious viral particles per cell) in low glucose Dulbecco's Modified Eagle Medium (DMEM), containing 1 g/l glucose (Cellgro). For double-infection experiments, i.e., AdPdx1+AdNgn3GFP, both viruses were diluted to an MOI of 1250. Negative control consisted of DMEM without virus. After the last PBS wash, PBS was removed from the cells and 0.35 ml of the viral suspension was added per well after which the cells were cultured at 37° C., 7.5% $CO_2$ in humidified air (21% $O_2$). After 2 hours, the viral suspension was removed, the cells were washed twice with PBS and further cultured at 37° C., 7.5% $CO_2$ in humidified air (21% $O_2$) in 60% low glucose DMEM, 40% MCDB-201 (Sigma), supplemented with 2% Fetal Calf Serum (FCS). Following transduction, the cells were maintained in the absence of cytokines or with exendin, nicotinamide and/or GDF11 for 3 days.

Following transduction with the adenoviral vectors, levels of murine Pdx-1 and Ngn3 mRNA were equal to (PDX-1) or significantly higher (Ngn3) than levels detected in mature murine pancreas. When cultured cells transduced with both the adenoviruses (Ad-Pdx1 and Ad-Ngn3, each at MOI 1:1250) were stained with antibodies against Pdx-1 and NeuroD1, most cells stained positive.

Transduction on d0 did not induce any changes in transcripts thought to be downstream of Pdx-1 and Ngn3, like NeuroD1. Transduction on d6, at which time low levels of endogenous Pdx-1 were present, induced some increase in expression of NeuroD1 and Ins1. Transduction of d12 rat MAPCs with Ad-Pdx-1 alone, increased expression of NeuroD1 by <100-fold, associated with a minimal effect on Ins1 and somatostatin mRNA levels. Transduction of d12 rat MAPCs with Ad-Ngn3 alone induced a >10,000 in NeuroD1 mRNA associated with a 100.000-fold increase in somatostatin mRNA and minimal increase in insulin-1 and glucagon mRNA.

Transduction of d12 rat MAPCs with a combination of Ad-Pdx-1 and Ad-Ngn3 resulted in a 10 fold increase in rat Pdx-1 mRNA, a 50 fold increase in NeuroD1 mRNA, 100 fold increase in Pax-4 mRNA associate with a >10,000-fold increase in Ins1 and 3,000 fold increase in somatostatin mRNA and no detectable amylase mRNA. Levels of earlier endoderm TFs, such as Hnf3, and Hnf6 were not significantly affected by adenoviral transductions, and levels of other endocrine pancreas TFs such as Pax6 and Nkx6.1 were only minimally affected.

These studies demonstrate that although overexpression of Ngn3 alone increases levels of NeuroD1 and somatostatin, only minimal effects are seen on insulin-1 mRNA. However, combining Ngn3 and Pdx-1 not only induces NeuroD1 expression, but also insulin-1 expression, consistent with the notion that the insulin promoter is maximally activated when NeuroD1 and Pdx1, two insulin-1 enhancer regulatory factors, are both present at high levels.

Immunohistochemistry for Pdx-1, Neuro-D1 and insulin in cultured cells was carried out as follows. Cells were washed twice with PBS (Cellgro) and fixed for 10 minutes with 10% neutral buffered formalin (Sigma) in PBS. After two washes with PBS, cells were permeabilized for 15 minutes with PBS+0.05% Tween-20. Endogenous peroxidase was blocked by incubation for 30 minutes in 3% $H_2O_2$ (Sigma) in methanol (Sigma). After a 2-minute wash with distilled water, endogenous biotin was blocked by sequential 15 minute incubations with avidin and biotin (Biotin Blocking System, DakoCytomation), separated by a 5 minute wash in PBS+0.05% Tween-20. After incubation with biotin, cells were washed for 5 minutes with PBS+0.05% Tween-20. Non-specific binding sites were blocked by incubation for 30 minutes with 0.4% fish skin gelatin (Sigma) in PBS. Blocking buffer was removed and primary antibody, diluted in PBS+0.05% Tween-20+1% Bovine Serum Albumin (BSA) (Jackson Immunoresearch) was added to the cells and incubated overnight at 4° C. Rabbit anti-Pdx1 was a gift from C. Wright, Vanderbilt University, Nashville and used at 1:2000. Rabbit anti-NeuroD1 was from Chemicon (AB5686) and used at 0.67 µg/ml. Guinea pig anti-insulin was from DakoCytomation (A0564) and used at 21.25 µg/ml. Rabbit and guinea pig isotype controls were from Jackson Immunoresearch and used at the same final concentration as the respective primary antibodies. The following morning, cells were washed three times for 5 minutes each with PBS+0.05% Tween-20. Biotinylated anti-rabbit or anti-guinea pig F(ab')$_2$ antibody, diluted 1:1500 in PBS+0.05% Tween-20 was added to the cells and incubated for 30 minutes. Cells were washed three times for 5 minutes each with PBS+0.05% Tween-20. The Vectastain ABC peroxidase complex (Vector Laboratories), prepared according to manufacturer's instructions, was added to the cells and incubated for 30 minutes. Cells were washed three times for 5 minutes each with PBS+0.05% Tween-20. Color was developed using DAB+(DakoCytomation), according to manufacturer's instructions. Pictures were taken using a Nikon Coolpix 4500 digital camera, mounted on a Zeiss Axioskop 2.

Immunohistochemistry for C-peptide on paraffin-embedded suspension cells was carried out as follows. Cells were washed twice with PBS and fixed for 10 minutes with 10% neutral buffered formalin in PBS. After two washes with PBS, cells were entrapped in a 2% Type VII Low Gelling Temperature agarose gel (Sigma) in PBS and paraffin-embedded. 6 micron sections were cut and placed on SuperFrost Plus slides (Fisher Scientific). After standard dewaxing and rehydration, staining and talking of pictures was done as described above for immunohistochemistry for Pdx1, Neuro-D1 and insulin in cultured cells. Rabbit anti-C-peptide (ab1043) was obtained from the Beta Cell Biology Consortium and used at 1:2000.

Insulin and C-peptide were measured by ELISA with the aid of the Ultrasensitive Rat Insulin ELISA kit (Mercodia) and the Rat C-peptide ELISA kit (Wako). For example, Rat Fisher MAPCs differentiated during 6 days with Activin-A, BMP4 and Anti-Shh Ab, followed by 6 days with EGF, were infected with Ad-Pdx-1 and Ad-Ngn3 (both at MOI 1250). Three days after infection, the supernatants were collected to measure the basal levels of insulin and C-peptide. The cells were next washed twice with PBS and incubated with 750 µL of 20 mM glucose. One hour later, the level of insulin and C-peptide in the supernatants of these cells was measured. RNA samples were also collected from these cells to evaluate the expression of insulin and other pancreatic markers. Table 8 provides a summary of the results regarding C-peptide secretion. Cells generated using sequential cytokine addition and transduction with a Pdx-1 and Ngn-3 adenoviral vector secrete C-peptide in response to 20 mM glucose.

TABLE 8

C-Peptide Secretion by MAPCs Differentiated to Endocrine Pancreas

|  | 0 mM glucose | 20 mM glucose |
| --- | --- | --- |
| D15 (FCS + Ad + 3) | 0.47 +/− 0.09 | 0.39 +/− 0.04 |
| D15 (ex/Nic + Ad + 3) | 0.36 +/− 0.07 | 0.67 +/− 0.02 |
| D15 (ex/Nic/GDF + Ad + 3) | 0.48 +/− 0.008 | 0.83 +/− 0.01 |

(MAPCs were plated confluently and treated sequentially with Activin, BMP4 and anti-SHH antibody (d1-6), then with EGF (d6-12). On day 12, cells were transduced with Ad-PDX-1 and AD-Ngn3, and maintained in basal medium for 3 days (FCS 2%), or maintained with exendin and nicotinamide and with or without GDF11. Cells were then exposed to 0 mM/mL glucose or 20 mM/mL glucose for 1 hour and media collected to measure C-peptide. Values are ng/L using a rat specific c-peptide ELISA.)

The data demonstrates that cells generated using sequential cytokine addition and transduction with a Pdx-1 and Ngn-3 adenoviral vector secrete C-peptide in response to 20 mM glucose. Assuming that 1 fmol of C-peptide contains 0.003325 ng of C-peptide, about 150.97 fmols of C-peptide/well (0.6 mL of media/well) was detected. Thus, these studies demonstrate that MAPCs induced to express Ins1 mRNA and Pdx-1 mRNA can also secrete insulin in response to glucose, a salient feature of functional β-cells.

Non-viral vectors may also be used. For example, cDNAs encoding PDX1 and neurogenin-3 (e.g., human or rat) were amplified from either RNA or genomic DNAs (Invitrogen). PCR amplification was conducted using standard methods with primers designed to exclusively amplify the open reading frame sequence of the gene, introduce the Kozak sequence (ccaccATG) for enhanced translation initiation, and incorporate unique flanking restriction enzyme sites for HindIII (aagctt) and XhoI (ctcgag) to facilitate cloning of the cDNA. Table 9 provides the primers for generating these cDNAs.

TABLE 9

| Primer Name | Primer Sequence | RE Site | SEQ ID NO: | Source Material |
|---|---|---|---|---|
| hPDX.F | atacaaagcttccaccATGAACGGCGAGGAGCAGTACTA | HindIII | 95 | total RNA, human Pancreas |
| hPDX.R | atacactcgagTCATCGTGGTTCCTGCGGCCGCCGAG | XhoI | 96 | |
| rPDX.F | atacaaagcttccaccATGAATAGTGAGGAGCAGTACTA | HindIII | 97 | total RNA, rat Pancreas |
| rPDX.R | atacactcgagTCACCGGGGTTCCTGCGGTCGCAGTGGC | XhoI | 98 | |
| hNRG.F | atacaaagcttccaccATGACGCCTCAACCCTCGGGTGC | HindIII | 99 | genomic DNA, human |
| hNRG.R | atacactcgagTCACAGAAAATCTGAGAAAGCCAGACTG | XhoI | 100 | |
| rNRG.F | atacaaagcttccaccATGGCGCCTCATCCCTTGGATGC | HindIII | 101 | genomic DNA, rat |
| rNRG.R | atacactcgagTCACAAGAAGTCTGAGAACACCAGGGTG | XhoI | 102 | |

Subsequently, amplified cDNAs were digested with HindIII and XhoI and cloned into the complementary sites of the commercial expression vector pcDNA3.1/Hygro(+) (Invitrogen cat. #V870-20). Purified vectors were linearized with AhdI or BglII prior to cell transfection. Linearized cDNAs were transfected into MAPCs by chemical transfection. Cells were grown in expansion media containing hygromycin as a selective agent.

Secretion of C-Peptide In Vitro in Response to Glucose in Non-Transduced Cells

Insulin production by MAPC-progeny under the influence of high glucose was measured. It was determined that samples with high level expression of insulin-1 mRNA also secreted insulin in the media under the influence of 20 mM glucose, further indicating that MAPCs can differentiate into cells with endocrine pancreatic features.

Figure 7:
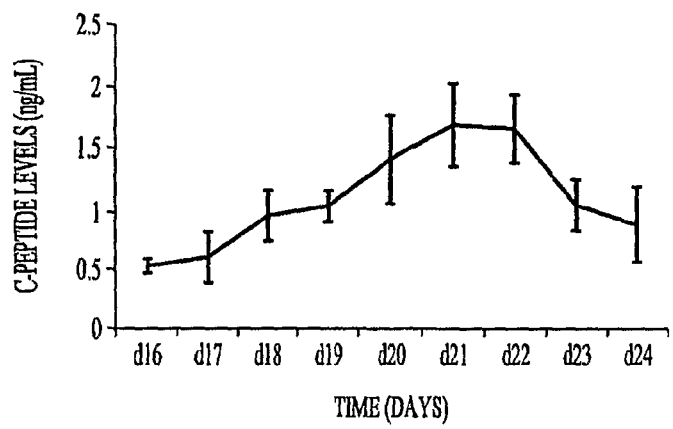
FIG. 7 depicts c-peptide secretion in vitro in response to 18 mM glucose. Cells were cultured with 3 nM glucose, and from dl 6-24, a daily pulse for 1 h of 18 nM glucose was added to the cultures, after which the supernatant was collected and c-peptide production measured by ELISA.

Additionally, C-peptide secretion was measured to assure that the insulin that was released was not insulin absorbed from the media that contains insulin (FIG. 7). In this evaluation, 4 cultures were cultured under low glucose (3 nM) and from d 16-24, a daily pulse for 1 h of 18 nM glucose was added to the cultures, after which the supernatant was collected and c-peptide production measured. These studies demonstrated that MAPCs cultured under the conditions described above, secrete c-peptide daily from d18 of culture on, with maximal secretion seen between days 20 and 22.

Insulin and C-peptide were measured by ELISA (Rajagopal et al., 2003; Hansson et al., 2004).

Calcium Imaging to Assess Channel Expression

Pancreatic β-cells secrete insulin in response to elevated glucose levels. β-cells are equipped with glucose transporters, ATP-sensitive potassium channels and voltage-activated (L-type) calcium channels that serve this function. Imaging and whole cell patch clamp studies can be used to determine if stem cell-derived pancreas β-like cells are similarly equipped to respond to elevated extracellular glucose (from 3-20 mM).

Figure 8:
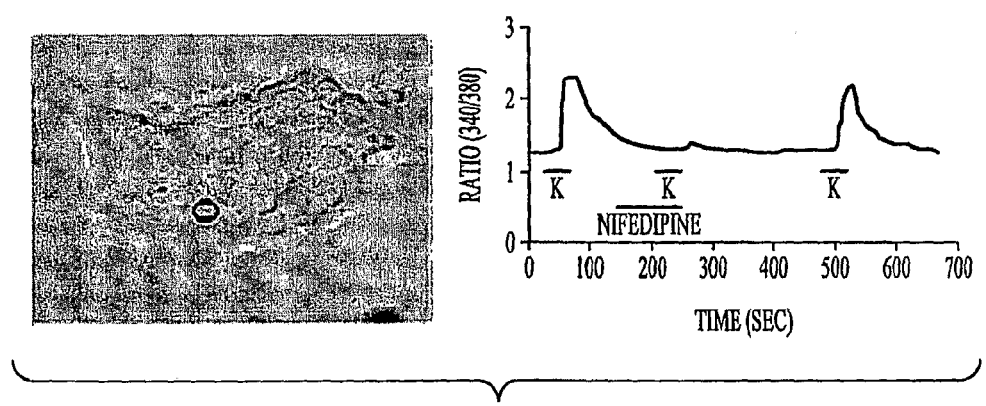
FIG. 8 depicts functional K and Ca channels on beta-like cell clusters. Left, an image of a cluster of cells that were loaded with fura-2 AM and placed on an inverted fluorescence microscope for video imaging. The plot on the right shows changes in intracellular calcium ion concentration ($[Ca^{2+}]_i$, as reflected by fura-2 ratio, in the region marked by a circle in the image. Increases in ($[Ca^{2+}]_i$ were evoked by increasing extracellular K ion concentration to 50 mM (from 3 mM), and this increase was inhibited by the L-type calcium channel blocker nifedipine (50 μM).

It was determined that MAPC-derived beta-cells express K channels and L-type voltage-activated calcium channels (calcium imaging experiments were carried out with cells loaded with the calcium indicator Fura-2 respond). FIG. 8 depicts the response of one cell. The same results were obtained in 12 other cells in the same cluster, and in two other clusters differentiated in the same manner. The data suggest that MAPC-derived beta-cells have K channels that are open under control conditions. Increasing extracellular K concentration causes a depolarization which leads to opening of voltage activated Ca channels. These channels are known to play a role in the response to glucose and resultant insulin secretion in β⁻-cells.

Functional Assessment of β-Cells In Vivo

Proof that the β-cells cells derived in vitro from MAPCs are functionally equivalent to β-cells isolated from adult mice was obtained by transplanting cells under the kidney capsule of SZO treated nude mice. Mice were rendered diabetic by a single intravenous injection of streptozotocin (200-240 mg/kg) via the tail vein. Diabetes was confirmed by two consecutive blood glucose values >400 mg/dl. Recipient mice were anesthetized using 0.015 ml/g body weight Avertin. The left or right kidney was exposed through a flank incision, a capsulotomy was performed in the upper pole of the kidney, and a pouch was created by separating the kidney capsule from the parenchyma with a fine glass probe toward the lower and anterolateral aspect of the kidney, and the MAPC-derived cells slowly advanced into the pouch. Mice that receive no cells served as negative controls, and mice grafted with 300 adult islets were used as positive controls (correction of hyperglycemia within 1 day).

As mice will not survive long term in a diabetic state, insulin pellets (LinBit, LinShin, Scarborough (Toronto), Ontario, Canada) were implanted to decrease blood glucose levels to around 300 mg/dL. Insulin pellets will progressively be removed when blood glucose levels are <200 mg/dL on 3 consecutive days. Alternatively, a renal subcapsular islet isograft in the opposite kidney from the one that received MAPC-derived β-cells will be performed. This will render the animal normoglycemic. The islet graft will then be removed about 2, 4 or 6 weeks after grafting the MAPC-derived β-cells/graft.

In one set of transplants, d21 MAPC derived progeny cells were grafted under the kidney capsule of 8 SZO treated animals. Animals had received SZO >5 days before the cell transplant. All animals had blood glucose levels of >500 mg/dL. On day −1, insulin pellets were implanted under the skin (insulin pellets were implanted according to the weight of the animal, e.g., 1 pellet for the first 20 grams and one more pellet for every 5 grams). On day 0, cells were grafted under the kidney capsule. In 4 animals, 1 million of the suspended clusters were grafted (~10-20,000 insulin positive cells). In the other 4 animals, a combination of 1 million of the suspended clusters were grafted (~10-20,000 insulin positive cells)+1 million of the attached stromal cells (enriched for cells expressing endothelial and smooth muscle markers, but low levels of endodermal transcripts and Insulin-1 transcripts). Animals were evaluated every 1-2 days for blood glucose levels. After ~4 weeks, insulin pellets were removed and animals were observed for 6-7 days. Animals that had glucoses >600 mg/dL on 2 consecutive days, were sacrificed. Animals that had blood glucoses of ≦400 mg/dL were kept for 6 days at which time the kidney with the graft was removed. Animals were then maintained for an additional 3-4 days to valuate blood glucose levels. The schema is shown in FIG. 9.

Figure 9A:
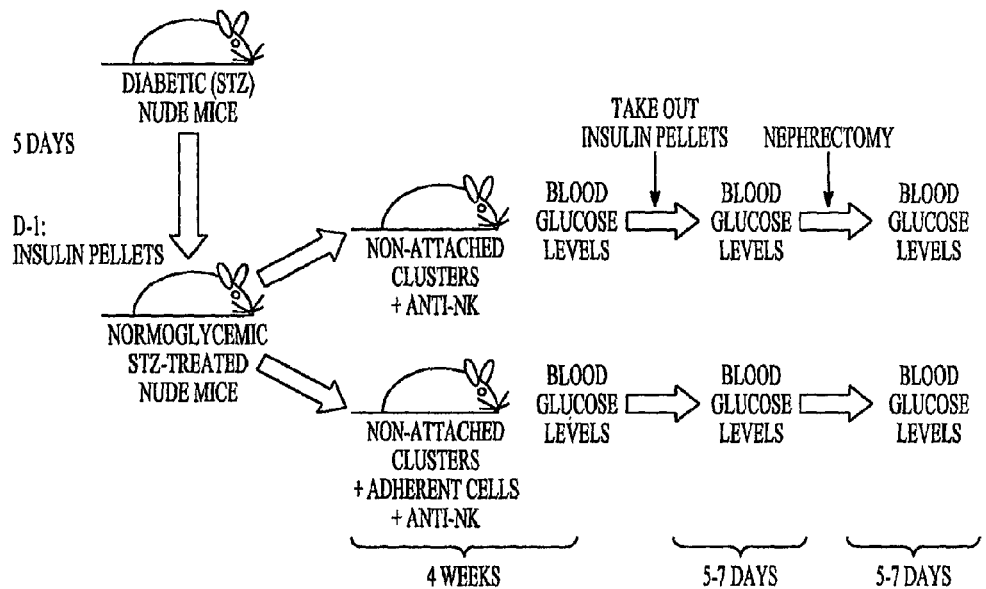
FIG. 9 depicts transplantation of endocrine pancreas differentiated rat MAPCs in SZO treated nude mice. Blood glucose levels (mg/dl) on the y axis; time in days on the x axis.
Figure 9B:
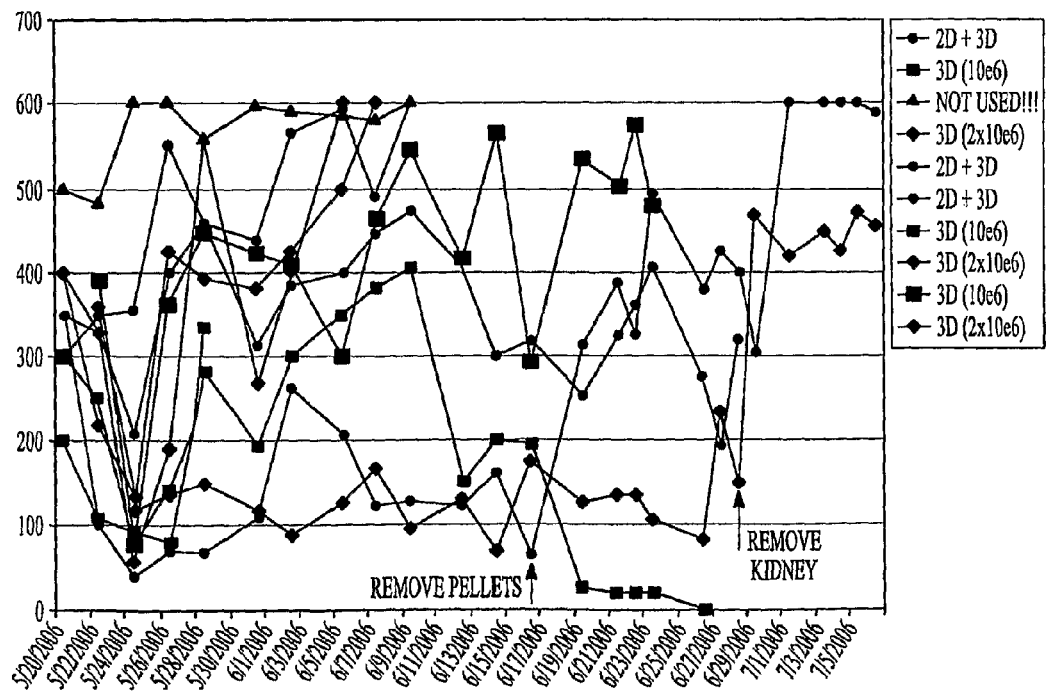

As shown in FIG. 9, 1 animal that received only supernatant cells, remained mostly normoglycemic (100-200 mg/dL) following removal of the insulin pellets. Upon removal of the kidney, a surgical problem occurred in that the diaphragm was damaged. Despite surgical correction, the animal remained ill, and did not eat, such that glucose levels post nephrectomy could not be evaluated.

2/4 animals that received a combination of supernatant cells and attached stromal cells maintained glucoses between 350 and 450 following removal of the insulin pellets and blood glucoses increased to >600 mg/dL after nephrectomy.

These studies suggest that cells grafted in the kidney of 3/8 animals contained cells that secrete insulin, which maintained blood glycemias between 150 and 450.

BIBLIOGRAPHY

Abe, A., et al., *J. Virol.* 1998; 72: 6159-6163.
Ahlgren, U., et al., *Genes Dev.* 1998; 12:1763-1768.
Akimenko, M. A., *J Neurosci* 1994; 14:3475-86.
Alter B P, *Cancer Genet Cytogenet.* 1992; 58:206-8; discussion 209.
Alvarez-Dolado M., et al. *Nature.* 2003; 425:968-973.
Ang, S. L., et al., *Development* 1993; 119:1301-1315.
Apelqvist, A., *Nature* et al., 1999; 400:877-881.
Aranguren X L, et al. *Keystone Symposium on stem cells.* 2005.
Babcook, et al., *Proc. Natl. Acad. Sci. (USA).* 1996; 93: 7843-7848.
Barker J N and Wagner J E. *Nature Reviews Cancer.* 2003; 3:526-532.
Barker J N et al., *Blood.* 2003; 102:1915-1919.
Barker J N et al., *Blood.* 2004; ePub.
Barnett M J et al., *Blood.* 1994; 84:724-732.
Basch, et. al., *J. Immunol. Methods.* 1983; 56:269.
Batinic, D., et al., *Bone Marrow Transplant.* 1990; 6(2):103-7.
Beattie, G. M., et al., *Diabetes.* 1996; 45(9):1223-8.
Beattie, G. M., et al., *Diabetes.* 1999; 48(5):1013-9.
Ben-Shushan E et al., *Mol Cell Biol.* 1998; 18:1866-1878.
Bertrand J Y et al., *Proc Natl Acad Sci USA.* 2005; 102:134-139.
Bhardwaj G et al., *Nat. Immunol.* 2001; 2:172-180.
Bhatia M et al., *Nat. Med.* 1998; 4:1038-1045.
Bhatia R et al., *Blood.* 1995; 85:3636-3645.
Bhatia R et al., *Blood.* 2003; 101:4701-4707.
Bhatia R et al., *J Clin Invest.* 1994; 94:384-391.
Bhushan A, et al. *Development.* 2001; 128:5109-5117.
Bierhuizen, M. et al., *Blood.* 1997; 90(9):3304-3315.
Bird, et al., *Science.* 1988; 242:423-426.
Bittira B, et al. *Eur J Cardiothorac Surg.* 2003; 24:393-398.
Bjorklund L M ea. *Proc Natl Acad Sci USA.* 2002; 99:2344-2349.
Bodnar, A. G., et al., *Science.* 1998; 279(5349):349-52.
Boneva, R. S, and T. M. Folks, *Ann Med.* 2004; 36(7):504-17.
Borue X, et al. *Am J Pathol.* 2004; 165:1767-1772.
Bossard, P., and Zaret, K. S. *Development* 1998; 125:4909-4917.
Bredenbeek, P. J., et al. *J. Virol.* 1993; 67:6439-6446.
Brice, G. T., et al., *J. Acquir Imm. Defic Syndr Hum Retrovirol* 1998; 19:210-220.
Brownlee, M., *Nature.* 2001; 414(6865):813-20.
Buckley S et al., *Stem Cells.* 2004.
Cai Z. H., et al., *Artif Organs.* 1988; 12(5):388-93.
Camargo F D et al., *J Clin Invest.* 2004; 113:1266-1270.
Cardona, K., et al., *Nat. Med.* 2006; 12(3):304-6.
Carella A M et al., *Blood Rev.* 1997; 11:154-159.
Cefalu, W. T., *Am J. Med.* 2002; 113 Suppl 6A:23S-35S.
Cerdan C et al., *Blood.* 2004; 103:2504-2512.
Chambers I et al., *Cell.* 2003; 113:643-655.
Chang, *Blood Purif.* 2000; 18:91-96.
Chang, P., et al., *Trends in Biotech.* 1999; 17:78-83.
Chang, T. M., *Artif Organs.* 1992; 16(1):71-4.
Choi K et al., *Biochem Cell Biol.* 1998; 76:947-956.
Choi K et al., *Development.* 1998; 125:725-732.
Clackson et al. *Nature.* 1991; 352:624-628.
Clarke, *Science.* 2000; 288:1660-3.
Clavel C, et al., Keystone Symposium on stem cells. 2005.
Clothia et al., *J. Mol. Biol.* 11985; 186:651-66, 1985.
Coligan, et al., *Current Protocols in Immunology*, (1991 and 1992).
Cras-Meneur, C., et al., *Diabetes* 2001; 50:1571-1579.
Csernus, V. J., et al., *Cell Mol Life Sci* 1998; 54:733-743.
D'Amour K A, et al., *Nat. Biotech.* 2005; 23:1432-1441.
Dao M A and Nolta J A. *Int J Mol. Med.* 1998; 1:257-264.
Davidson, B. L., et al., *Nature Genetics.* 1993; 3:219-223.
Deisseroth A B et al., *Blood.* 1994; 83:3068-3076.
Desai, T. A., *Exp. Opin. Biol. Ther.* 2002; 2:633-646.
Dominguez-Bendala, J., et al., *Diabetes* 2005; 54:720-726.
Dor, Y., et al., *Nature.* 2004; 429(6987):41-6.
Douglas, J. et al., *Hum. Gene Ther.* 1999; 10(6):935-945.
Douglas, J., et al. *Nature Biotech.* 1999; 17:470-475.
Drukker M, et al. *Proc Natl Acad Sci USA.* 2002; 99:9864-9869.
Dull, T., et al., *J. Virol.* 1998; 72:8463-8471.
Dyer M A et al., *Development.* 2001; 128:1717-1730.
Eckfeldt C E et al., *PLoS Biology.* 2004.
Edlund, H., *Nat Rev Genet.* 2002; 3(7):524-32.
Efrat, S., *Ann NY Acad Sci.* 1999; 875:286-93.
Efrat, S., *Ann NY Acad Sci.* 2004; 1014:88-96.
Efrat, S., *Diabetes.* 2001; 50 Suppl 1:S189-90.
Efrat, S., et al., *Proc Natl Acad Sci USA.* 1995; 92(8):3576-80.
Embury, J., et al., *Diabetes* 2001; 50:1706-1713.
Faloon P et al., *Development.* 2000; 127:1931-1941.
Ferrari, *Science.* 1998; 279:528-30.
Fleischer, N., et al., *Diabetes.* 1998; 47(9):1419-25.
Foerst-Potts, L. *Dev Dyn* 1997; 209:70-84.
Froguel, P. and G. Velho, *Trends Enidocrinol Metab.* 1999; 10(4):142-146.
Frolov, I., et al. (*Proc. Natl. Acad. Sci. USA.* 1996; 93:11371-11377.
Gambacorti-Passerini C B et al., *Lancet Oncol.* 2003; 4:75-85.
Gerberding, J. L., Diabetes: Disabling, Deadly, and on the Rise, in CDC At A Glance. 2006, Centers for Disease Control and Prevention.
Gittes, G. K., et al., *Development* 1996; 122:439-447.
Gluckman E. *Stem Cells* 1993; 11 Suppl 2:180-3.
Good, A. H., et al., *Transplant Proc.,* 1992; 24(2):559-62.

Gradwohl, G., et al., *Proc Natl Acad Sci USA.* 2000; 97:1607-1611.
Grant M B et al., *Nat. Med.* 2002; 8:607-612.
Guardiola P, et al., *Blood.* 2000; 95:422-9.
Guinan E C et al., *J Pediatr* 1994; 124:144-50.
Gunsilius E et al., *Lancet.* 2000; 355:1688-1691.
Gupta P et al., *Blood.* 1996; 87:3229.
Gupta P et al., *Blood.* 1998; 92:4641-4651.
Gussoni, *Nature.* 1999; 401:390-4.
Gyukhandanyan A V, et al., *J Biol. Chem.* 2006; 281:9361-9372.
Habener, J. F., ed. Molecular Basis of Pancreas Development and Function. 2001, Kluwer Academic Publishers.
Hansson, M., et al., *Diabetes* 2004; 53:2603-2609.
Hardikar, A. A., et al., *Proc Natl Acad Sci U.S.A.* 2003; 100:7117-7122.
Harmon, E. B., et al., *Development* 2004; 131:6163-6174.
Harraz M et al., *Stem Cells.* 2001; 19:304-312.
Harris R G et al., *Science.* 2004; 305:90-93.
Hart, A., et al. *Dev Dyn.* 2003; 228:185-193.
Harvey K and Dzierzak E. *Stem Cells.* 2004; 22:253-258.
Hayek, A., et al., *Diabetes.* 1995; 44(12):1458-60.
He T-C et al., *Proc. Natl. Acad. Sci. USA.* 1998; 95:2509.
Hebrok, M., et al., *Development* 2000; 127:4905-4913.
Heller, R. S., *Dev Dyn.* 2002; 225:260-270.
Heller, R. S., et al., *Dev Biol.* 2005; 286(1):217-24.
Hematti P et al., *PLOS Biology.* 2004; 2:e243.
Hemmati-Brivanlou A et al., *Dev Genet.* 1995; 17:78-89.
Henry G L, et al., *Science.* 1998; 281:91-96.
Hentsch, B., et al., *Genes Dev.* 1996; 10:70-79.
Heremans Y et al., *J. Cell Biol.* 2002; 159:303-12.
Hering, B. J., et al., *Nat. Med.* 2006; 12(3):301-3.
Hofmann, C., et al. *J. Virol.* 1999; 73:6930-6936.
Hogan C J et al., *Blood.* 1997; 90:85-96.
Hollinger et al., *Proc. Natl. Acad. Sci. USA.* 1993; 906444-6448 (1993).
Holmes, et al., *J. Immunol.* 1997; 158:2192-2201.
Holyoake T L et al., *Exp Hematol.* 1999; 27:1418-1427.
Hori and Kim, *PLos Biology* 2005.
Hori, Y., et al., *Proc Natl Acad Sci U.S.A.* 2002; 99:16105-16110.
Howe C W S, Radde-Stepanick T. Hematopoietic Cell Donor Registries. In: Thomas E D, Blume, Karl G. and Forman, Stephan J., ed. Hematopoictic Cell Transplantation. Vol. 2. Maiden, Mass.: Blackwell Sciences; 1999:503-512.
Huotari, M. A., et al., *Endocrinology* 2002; 143:4437-4446.
Hurley R W et al., *J Clin Invest.* 1995; 96:511-521.
Ianus A, et al., *J Clin Invest.* 2003; 111:843-850.
Jackson, *PNAS USA.* 1999; 96:14482-6.
Jahagirdar, B. N., et al. *Exp Hematol.* 2001; 29(5):543-56.
Jensen, J., et al., *Diabetes* 2000; 49:163-176.
Jiang Y et al., *Blood.* 2000; 95:846-854.
Jiang Y et al., *Proc Natl Acad Sci USA.* 2000; 97:10538-10543.
Jiang Y, et al., *Exp Hematol.* 2002; 30:896-904.
Jiang Y, et al., *Nature.* 2002; 418:41-49.
Jiang Y, et al., *Proc Natl Acad Sci USA.* 2003; 100 Suppl 1:11854-11860.
Johnston, S. A., et al. *Genet. Eng.* (NY) 1993; 15: 225-236.
Jones et al., *Nature.* 1986; 321:522-525.
Jung, J., et al., *Science* 1999; 284:1998-2003.
Kafri, T., et al., *J. Virol.* 1999; 73:576-584.
Kahan, B. W., *Diabetes* et al., 2003; 52:2016-2024.
Kanai-Azuma, M., et al., *Development* 2002; 129:2367-2379.
Kannagi, R. *EMBO J* 1983; 2:2355-61.
Kantarjian H M et al., *Blood.* 2003; 101:97-100.
Kataoka, K., et al., *J Biol. Chem.* 2002; 277:49903-49910.
Kaufman D S et al., *Proc Natl Acad Sci USA.* 2001; 98:10716-10721.
Kaufman D S, and Thomson J A. *J Anat.* 2002; 200:243-248.
Kawada H, et al. *Blood.* 2004; 104:3581-3587.
Kawaguchi, Y., et al., *Nat. Genet.* 2002; 32:128-134.
Keene, C. D., et al., *J Cell Science* 2003; 12:210-213.
Kemahli S et al., *Br J Haematol* 1994; 87:871-2.
Kogler G et al., *J Exp Med.* 2004; 200:123-135.
Kohler & Milstein, *Nature.* 1975; 256:495.
Kohli-Kuniar M et al., *Blood.* 84:2050-4, 1994.
Kojima, H., et al., *Nat. Med.* 2003; 9:504-505.
Korytkowski, M., et al., *Clin Ther.* 2005; 27 Suppl B:S89-100.
Krause D S, et al. *Cell.* 2001; 105:369-377.
Ku, H. T., et al., *Stem Cells* 2004; 22:1205-1217.
Kubo, A., et al. *Development* 2004; 131:1651-1662.
Kusadasi N et al., *Leukemia.* 2002; 16:1782-1790.
Kyba M et al., *Cell.* 2002; 109:29-37.
Kyba M et al., *Proc Natl Acad Sci USA.* 2003; 100, Suppl 1:11904-11910.
Lagasse E, et al. *Nat. Med.* 2000; 6:1229-1234.
Lammert, E., et al., *Science* 2001; 294:264-267.
Lanier L L. "NK Cell Recognition." *Annu Rev Immunol.* 2004.
Laquerre, S., et al. *J. Virol.* 1998; 72:9683-9697.
Larrick, et al., *Methods: A Companion to Methods in Enzymology.* (1991).
Lawrence, H. *Blood* 1997; 89:1922.
Lechner A, et al., *Diabetes.* 2004; 53:616-623.
Lechner, A. and J. F. Habener, *Am J Physiol Endocrinol Metab.* 2003; 284(2):E259-66.
Ledermann, H. M., *Diabetologia.* 1995; 38(12): 1482.
Lee, S. H., et al., *Nat. Biotechnol.* 2000; 18:675-679.
Lefebvre V. *Matrix Biol* 1998; 16:529-40.
Leslie, R. D., et al., *J Clin Endocrinol Metab.* 2006; 91(5): 1654-9.
Leung A Y H et al., *Dev Biol.* 2004.
Lewis I D et al., *Blood.* 2001; 97:3441-3449.
Li Z, et al. *Dev Biol.* 2004; 269:252-263.
Lim, J. W. and Bodnar, A., *Proteomics.* 2002; 2(9): 1187-1203 (2002).
Liu H J, Lamming C, C. M. V. Characterization of Human Bone Marrow and Umbilical Cord Blood Self-Renewing Multi-lineage Hematopoietic Stem Cells. 2003.
Liu J M: Fanconi's anemia, in Young NS (ed): Bone marrow failure syndromes. Philadelphia, W.B. Saunders company, 2000, p 47-68.
Liu, P., et al., *Nat. Genet.* 1999; 22:361-366.
Loeffler, J. and Behr, J., *Methods in Enzymology.* 1993; 217: 599-618.
Lumelsky, N., et al., *Science* 2001; 292:1389-1394.
Maldonado, T. S., et al., *J Gastrointest Surg.* 2000; 4:269-275.
Marks et al., J. Mol. Biol. 1991; 222:581-597.
Martin, F., et al., *J. Virol.* 1999; 73:6923-6929.
Mathews V, et al., *Diabetes.* 2004; 53:91-98.
Matsumoto, K., et al., *Science* 2001; 294:559-563.
Matsuoka, T. A., et al., *Proc Natl Acad Sci* (USA) 2004; 101:2930-2933.
Matthew, H. W., et al., *ASAIO Trans.* 1991; 37(3):M328-30.
Matzuk, M. M., et al., *Nature* 1995; 374:356-360.
McDowell, N., et al., *Curr Biol.* 1997; 7:671-681.
McEntyre, L. D. a. J. R., *The Genetic Landscape of Diabetes.* 2004: NLM/NCBI.
McEvoy R C, et al., *J Clin Invest.* 1984; 74:715-722.
Medvinsky A et al., *Cell.* 1996; 86:897.
Meivar-Levy and Ferber, *Trends Endocrinol Metab.* 2003; 14(10):460-6.

Mikkola H K et al., *Blood.* 2003; 101:508-516.
Miller, A. D., and C. Buttimore, *Mol. Cell. Biol.* 1986; 6:2895-2902.
Miralles F, et al., *Dev Dyn.* 1999; 214:116-126.
Miyazaki et al., *Diabetes.* 2004; 53:1030-7.
Mochizuki, H., et al., *J. Virol.* 1998; 72:8873-8883.
Molin, M., et al. *J. Virol.* 1998; 72:8358-8361.
Montague, W., and Cook, J. R. *Biochem J.* 1971; 122:115-120.
Morrison et al. *Proc. Natl. Acad. Sci.* 1984; 81, 6851-6855.
Movassat, J., et al., *J Clin Endocrinol Metab.* 2002; 87:87.
Muguruma, Y., et al., *Exp Hematol.* 2003; 31:1323-1330.
Murtaugh, L. C., et al., *Proc Natl Acad Sci U.S.A.* 2003; 100: 14920-14925.
Muschler, G. F., et al. *J. Bone Joint Surg. Am.* 1997; 79(11): 1699-709.
Najarian, J. S., et al., *Transplant Proc.* 1977; 9(1):233-6.
Nakano T et al., *Science.* 1994; 265:1098-1101.
Narushima, M., et al., *Nat. Biotechnol.* 2005; 23(10):1274-82.
Nichols J et al., *Cell.* 1998; 95:379-391.
Norgaard, G. A., et al., *Dev Biol* 2003; 264:323-338.
Novotny and Haber, *Proc. Natl. Acad. Sci. USA.* 1985; 82; 4592-4596.
Nusse, R. *Nature* 2001; 411:255-256.
Nyqvist, D., et al., *Diabetes.* 2005; 54(8):2287-93.
Offield, M. F., et al., *Development* 1996; 122:983-995.
Ohara-Imaizumi, M., et al., *J Biol Chem.* 2002; 277:50805-50811.
Oostendorp R A et al., *Blood.* 2002; 99:1183-1189.
Oostendorp R A et al., *J Cell Sci.* 2002; 115:2099-2108.
Otonkoski, T., et al., *J Clin Invest.* 1993; 92:1459-1466.
Pack, et al., *Bio/Technology.* 1993; 11: 1271-77.
Packer, A. I., *Dev Dyn* 2000; 17:62-74.
Pelengaris S, et al., *Cell.* 2002; 109:321-334.
Persons, D., et al., *Nature Medicine.* 1998; 4:1201-1205.
Petersen, H. V., et al., *Mol Cell Biol Res Commun.* 2000; 3:249-254.
Petersen, *Science.* 1999; 284:1168-1170.
Pipeleers, D. and Z. Ling, *Diabetes Metab Rev.* 1992; 8(3): 209-27.
Pittenger, *Science* 1999; 284:143-147.
Potocnik A J et al., *Proc Natl Acad Sci USA.* 1997; 94: 10295-10300.
Presta, *Curr. Op. Struct. Biol.* 1992; 2:593-596.
Punzel M et al., *Blood.* 1999; 93:3750-3756.
Rackoff W R et al., *Blood.* 1996; 88:1588-93.
Rajagopal, J., et al. *Science* 2003; 299:363.
Rayat, G. R., et al., *J Endocrinol.* 2003; 177(1):127-35.
Rebel V I et al., *Blood.* 1996; 87:3500-3507.
Reichmann et al., *Nature.* 1988; 332:323-329.
Rescan, C., et al., *Lab Invest.* 2005; 85:65-74.
Reya T et al., *Nature.* 2003; 423:409-414.
Reyes M et al., *Ann NY Acad Sci.* 2001; 938:231-233; discussion 233-235.
Reyes, M., et al., *Blood* 2001; 98:2615-2625.
Reyes, M., et al., *J Clin Invest.* 2002; 109:337-346.
Reyes and Verfaillie, *Ann NY Acad Sci.* 2001; 938:231-233; discussion 233-235.
Rideout W Mr et al. *Cell.* 2002; 109:17-27.
Robbins, et al. *J. Virol.* 1997; 71(12):9466-9474.
Rojas, E., et al., *FEBS Lett.* 1990; 261:265-270.
Rood, P.P. and D. K. Cooper, *Am J. Transplant.* 2006; 6(6): 1269-74.
Rosario, L. M., et al., *Adv Exp Med Biol.* 1986; 211:413-425.
Rosenfeld, L., *Clin Chem.* 2002; 48(12):2270-88.
Rosfjord E, Rizzino A. *Biochem Biophys Res Commun.* 1997; 203:1795-802.
Rowley J. *Cancer.* 1990; 65:2178-2184.
Salmons, B. and Gunzburg, W. H., 1993; 4:129-141.
Saltiel, A. R. and C. R. Kahn, *Nature.* 2001; 414(6865):799-806.
Sander, M., et al., *Development* 2000; 127:5533-5540.
Sander, M., et al., *Genes Dev.* 1997; 11:1662-1673.
Sanvito, F., et al., *Development* 1994; 1994:3451-3462.
Sawai, K., et al., *Mol Genet Metab.* 1998; 64:44-51.
Scagni P et al., *Haematologica* 1988; 83:432-7.
Schuh A C, et al., *Proc Natl Acad Sci USA.* 1999; 96:2159-2164.
Schwartz R E, et al. *J Clin Invest.* 2002; 109:1291-1302.
Schwartz R E, et al. *J Clin Invest.* 2002; 96:1291-1302.
Schwarzenberger, P., et al., *J. Virol.* 1997; 71:8563-8571.
Sebestyen, et al. *Nature Biotech.* 1998; 16:80-85.
Shapiro, A. M., et al., *N Engl J. Med.* 2000; 343(4):230-8.
Shen, C. N., et al., *Nat Cell Biol.* 2000; 2:879-887.
Shimozaki et al. *Development.* 2003; 130:2505-12.
Sipione, S., et al. *Diabetologia* 2004; 47:499-508.
Smith, S. B., et al., *Mol Cell Biol.* 1999; 19:8272-8280.
Soria, B., et al., *Diabetes* 2000; 49:157-162.
Sosa-Pineda, B., et al., *Nature* 1997; 386:399-402.
Spangrude G et al., *Science.* 1988; 241:58.
Sreenan S, et al., *Diabetes.* 1999; 48:989-996.
Stock, P. G. and J. A. Bluestone, *Annu Rev Med.* 2004; 55:133-56.
Sussel, L., et al., *Development* 1998; 125:2213-2221.
Sutherland, D. E., et al., *Surg Clin North Am.* 1978; 58(2): 365-82.
Sutton, R., et al., *J. Virol.* 1998; 72:5781-5788.
Takahashi, *J Clin Invest.* 2000; 105:71-7.
Takahashi, *Nat. Med.* 1999; 5:434-8.
Theise, *Hepatology.* 2000a; 31:235-40.
Theise, *Hepatology.* 2000b; 32: 11-6.
Theunissen K and Verfaillie C M. *Exp Hematol.* 2004.
Thomas E et al., *Ann Int Med.* 1986; 104:155-163.
Thomas ED. *Semin Hematol.* 1999; 36:95-103.
Thomson J A et al., *Science.* 1998; 282:1145-1147.
Tian X et al., *Exp Hematol.* 2004; 32:1000-1009.
Tolar J et al., *Blood.* 2003; ASH Abstract.
Traggiai E et al., *Science.* 2004; 304:104-107.
Trube, G., et al., *Pflugers Arch.* 1986; 407: 493-499.
Tsuchida, K., et al., *Mol Cell Endocrinol.* 2004; 220:59-65.
Uwanogho D. et al., *Mech Dev* 1995; 49:23-36.
Vaca P, et al., *Stem Cells.* 2005; [Epub ahead of print].
Van Tendeloo, et al., *Blood* 2001 et al., 98:49-56.
Van Tendeloo, et al., *Gene Ther.* 2000; 7:1431-1437.
Vaswani, et al., Annals Allergy, Asthma & Immunol. 1998; 81:105-115.
Verfaillie C et al., *Blood.* 1992; 79:1003-1010.
Verfaillie C et al., *Blood.* 1998; 92:1820-1831.
Verfaillie C et al., *J Exp Med.* 1991; 174:693-703.
Verfaillie C. *Blood.* 1992; 79:2821-2826.
Verfaillie C M et al., *J Clin Invest.* 1992; 90:1232.
Verfaillie C M, et al., *Blood.* 1996; 87:4770-4779.
Verfaillie, C. M. *Trends Cell Biol.* 2002; 12(11):502-8.
Vodyanik M A et al., *Blood.* 2005; 105:617-626.
Wagers A J, et al. *Science.* 2002; 297:2256-2259.
Wagner, E., et al., *Proc. Natl. Acad. Sci. USA.* 1992; 89:6099-6103.
Wang L et al., *Immunity.* 2004; 21:31-41.
Wang X et al., *Nature.* 2003; 422:897-901.
Weber, H., et al., *Development* 2000; 127:4345-4360.
Wells, J. M., and Melton, D. A. *Development* 2000; 127:1563-1572.

Whitlow, et al., *Methods: A Companion to Methods in Enzymology* (1991).
Willert K, and Nusse R. *Curr Opin Genet Dev.* 1998; 8:95.
Williams, R. S., et al., *Proc. Natl. Acad. Sci. USA.* 1991; 88:2726-2730.
Winnier, G., et al., *Genes Dev.* 1995; 9:2105-2116.
Wold, W., Adenovirus Methods and Protocols, Humana Methods in Molecular Medicine (1998), Blackwell Science, Ltd.
Wu G D, et al. *Transplantation.* 2003; 75:679-685.
Wysocki and Sato, *Proc. Natl. Acad. Sci. (USA).* 1978; 75:2844.
Xiong, C., et al., *Science.* 1989; 243:1188-1191.
Yahata T et al., *J Immunol.* 2002; 69:204-209.
Yanagi, K., et al., *ASAIO Trans.* 1989; 35(3):570-2.
Yang, N. S., et al., *Proc. Natl. Acad. Sci. USA.* 1990; 87:9568-9572.
Yoder M et al., *Proc Natl Acad Sci USA.* 1997; 94:6776.
Yoshida et al., *Diabetes.* 2002; 51:2505-13.
Zambanini, A., et al., *Diabetes Res Clin Pract.* 1999; 46(3):239-46.
Zaret, K. S. *Mech Dev.* 2000; 15:83-88.
Zeng, L., et al., *Blood ASH Abstract* 2004.
Zhang, G. et al., *Biochem. Biophys. Res. Commun.* 1996; 227(3):707-711.
Zhao L R, et al. *Exp Neurol.* 2002; 174:11-20.
Zhao R et al., *Blood.* 1997; 90:4687-4698.
Zhao R C H et al., *Blood.* 2001; 97:2406-2412.
Zhao, L., et al., *J Biol Chem.* 2005; 280:11887-11894.
Zhou, X., et al., *Nature* 1993; 361:543-547.
Zimmet, P., et al., *Nature.* 2001; 414(6865):782-7.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An in vitro method comprising contacting non-embryonic stem, non-germ, non-embryonic germ cells that can differentiate into at least two of ectodermal, endodermal and mesodermal cell types with agents consisting essentially of Activin A and an agent that inhibits sonic hedgehog (SHH) activity to yield cells having increased expression of Pdx-1.

2. The method of claim 1 further comprising contacting the non-embryonic stem, non-germ, non-embryonic germ cells with factors consisting essentially of BMP4.

3. The method of claim 1 further comprising contacting the cells having increased Pdx-1 expression with factors consisting essentially of EGF or HGF to yield cells having increased expression of Ngn3.

4. An in vitro method to differentiate non-embryonic stem, non-germ, non-embryonic germ cells that can differentiate into at least two of ectodermal, endodermal and mesodermal cell types comprising the steps of:
   a) contacting the non-embryonic stem, non-germ and non-embryonic germ cells with factors consisting essentially of Activin A and an agent that inhibits sonic hedgehog activity, to produce cells with increased expression of Pdx-1;
   b) contacting the cells obtained from step a) with factors consisting essentially of EGF or HGF, to produce cells expressing Ngn3; and
   c) contacting the cells obtained from step b) with factors consisting essentially of one or both of nicotinamide or exendin4, to produce cells expressing insulin.

5. The method of claim 4 wherein step a), step b) or both further comprise contacting the cells with factors consisting essentially of BMP4.

6. The method of claim 4 wherein step d) further comprises contacting the cells with factors consisting essentially of one or both of GDF11 or betacellulin.

7. A composition comprising (1) factors consisting essentially of Activin A and an agent that inhibits sonic hedgehog and (2) non-embryonic stem, non-germ, non-embryonic germ cells that differentiate into at least two of ectodermal, endodermal and mesodermal cell types.

8. The composition of claim 7 further comprising factors consisting essentially of BMP4.

9. The composition of claim 7, wherein the composition further comprises cell culture medium or a pharmaceutically acceptable carrier.

10. The composition of claim 7 wherein the sonic hedgehog inhibitor is cyclopamine or an anti-SHH antibody.

11. The composition of claim 8, wherein the composition further comprises cell culture medium or a pharmaceutically acceptable carrier.

* * * * *

UNITED STATES PATENT AND TRADEMARK OFFICE
CERTIFICATE OF CORRECTION

PATENT NO. : 8,409,859 B2  Page 1 of 1
APPLICATION NO. : 12/089868
DATED : April 2, 2013
INVENTOR(S) : Verfaillie et al.

It is certified that error appears in the above-identified patent and that said Letters Patent is hereby corrected as shown below:

In the Specification

In column 1, lines 12-15, please delete the two (2) sentences

"This invention was made with the assistance of government support under United States Grant No. U19 DK 61244 from the National Institutes of Health. The government may have certain rights to the invention."

and insert

--This invention was made with government support under U19-DK061244 awarded by the National Institutes of Health. The government has certain rights in the invention.--

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,409,859 B2                              Page 1 of 1
APPLICATION NO. : 12/089868
DATED            : April 2, 2013
INVENTOR(S)      : Verfaillie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1276 days.

Signed and Sealed this
First Day of September, 2015

Michelle K. Lee
*Director of the United States Patent and Trademark Office*